US010842797B2

(12) United States Patent
Zaworotko et al.

(10) Patent No.: US 10,842,797 B2
(45) Date of Patent: *Nov. 24, 2020

(54) NUTRACEUTICAL CO-CRYSTAL COMPOSITIONS

(71) Applicant: UNIVERSITY OF SOUTH FLORIDA, Tampa, FL (US)

(72) Inventors: Michael John Zaworotko, Parteen (IE); Heather Clarke, Tampa, FL (US); Arora Kapildev, Niantic, CT (US); Padmini Kavuru, Fitchburg, MA (US); Roland Douglas Shytle, Largo, FL (US); Twarita Pujari, Tampa, FL (US); Lissette Marshall, Tampa, FL (US); Tien Teng Ong, Singapore (SG)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,317

(22) Filed: May 24, 2019

(65) Prior Publication Data

US 2019/0275056 A1 Sep. 12, 2019

Related U.S. Application Data

(63) Continuation of application No. 14/533,255, filed on Nov. 5, 2014, now Pat. No. 10,376,521, which is a continuation of application No. 12/663,212, filed as application No. PCT/US2008/007129 on Jun. 6, 2008, now abandoned.

(60) Provisional application No. 60/982,619, filed on Oct. 25, 2007, provisional application No. 60/942,355, filed on Jun. 6, 2007.

(51) Int. Cl.
| | | |
|---|---|---|
| *A61K 31/55* | (2006.01) | |
| *A61K 31/20* | (2006.01) | |
| *C07D 401/14* | (2006.01) | |
| *A23L 33/10* | (2016.01) | |
| *A61K 31/197* | (2006.01) | |
| *A61K 31/375* | (2006.01) | |
| *A61K 31/455* | (2006.01) | |
| *A61K 31/522* | (2006.01) | |

(52) U.S. Cl.
CPC .............. *A61K 31/55* (2013.01); *A23L 33/10* (2016.08); *A61K 31/197* (2013.01); *A61K 31/20* (2013.01); *A61K 31/375* (2013.01); *A61K 31/455* (2013.01); *A61K 31/522* (2013.01); *C07D 401/14* (2013.01)

(58) Field of Classification Search
CPC ...... A61K 31/522; A61K 31/52; A61K 31/35; A61K 31/37
USPC .................. 424/464; 514/220, 221, 406, 574
See application file for complete search history.

(56) References Cited

U.S. PATENT DOCUMENTS

| | | | |
|---|---|---|---|
| 10,376,521 B2 * | 8/2019 | Zaworotko | .......... A61K 31/522 |
| 2003/0224006 A1 | 12/2003 | Zaworotko et al. | |
| 2007/0026078 A1 | 2/2007 | Almarsson et al. | |
| 2007/0059356 A1 | 3/2007 | Almarsson et al. | |
| 2007/0299033 A1 | 12/2007 | McMahon et al. | |
| 2008/0146772 A1 | 6/2008 | Zaworotko et al. | |
| 2010/0173984 A1 | 7/2010 | Zaworotko et al. | |
| 2010/0204204 A1 | 8/2010 | Zaworotko et al. | |
| 2010/0311701 A1 | 12/2010 | Almarsson et al. | |
| 2012/0172423 A1 | 7/2012 | Hsu | |

FOREIGN PATENT DOCUMENTS

| | | |
|---|---|---|
| CN | 1470510 | 1/2004 |
| EP | 0528604 | 2/1993 |
| WO | 9607331 | 3/1996 |
| WO | 03074474 | 9/2003 |
| WO | 2004078163 | 9/2004 |
| WO | 2007041891 | 4/2007 |

OTHER PUBLICATIONS

Yao, et al., Epigallocatechin Gallate Protects Against Oxidative Stress-Induced Mitochondria-Dependent Apoptosis in Human Lens Epithelial Cells, Molecular Vision 2008: 217-23.
Potenza, et al., EGCG, a Green Tea Polyphenol, Improves Endothelial Function and Insulin Sensitivity, Reduces Blood Pressure, and Protects Against Myocardial I/R Injury in SHR, Am. J Physiol Endocrinol Metab 2007: 1378-1387.
Katiyar et al., Green Tea Polyphenol (-)Epigallocatechin-3-Gallate Treatment of Human Skin Inhibits Ultraviolet Radiation-Induced Oxidative Stress, Carcinogenesis 2001; vol. 22: 287-294.
Rezai-Zedeh et al., Green Tea Epigallocatechin-3-Gallate (EGCG) Modulates Amyloid Precursor Protein Cleavage and Reduces Cerebral Amyloidosis in Alzheimer Transgenic Mice, Journal of Neuroscience, 2005; 8807-8814.
Collins et al., Epigallocatechin-3-Gallate (EGCG), a Green Tea Polyphenol, Suppresses Hepatic Gluconeogenesis hrough 5'-AMP-activated Protein Kinase, Journ. Biological Chemistry, 2007; vol. 282, 30143-30149.
International Search Report dated Dec. 12, 2010 on PCT/US2008/007117.
Almarsson et al., Crystal engineering of the composition of pharmaceutical phases. Do pharmaceutical co-crystals represent a new path to improved medicines?, Chemical Communications, 2004, 1889-1896.
Anastas et al., Green Chemistry Theory and Practice, Chapter 4 Principles of green chemistry, 2000, 29-55, Oxford University Press, USA.

(Continued)

*Primary Examiner* — Kevin E Weddington
(74) *Attorney, Agent, or Firm* — Thomas | Horstemeyer, LLP

(57) ABSTRACT

Co-crystals comprising at least one nutraceutical compound and at least one co-crystal former with or without impurities. These co-crystals may be included in compositions (optionally also including other components such as pharmaceutically acceptable excipients, other nutritional supplements, etc.) having utility as pharmaceuticals, nutraceuticals, nutritional supplements, and foodstuffs.

18 Claims, 64 Drawing Sheets

(56) References Cited

OTHER PUBLICATIONS

Borah et al., Microwave-induced one-pot synthesis of N-carboxyalkyl maleimides and phthalimides, Journal of Chemical Research, 1998, 272-273.

Chandrasekhar et al., Sovent free N-alkyl and N-arylimides preparation for anhydrides catalyzed by TaCl5-Silica gel, Tetrahedron Letters, 1997, 38(46), 8089-8092.

Childs et al., Crystal engineering approach to forming cocrystals of amine hydrocholorides with organic acids. Molecular complexes of fluoxetine hydrochloride with benzoic, succinic, and fumaric acids, Journal of American Chemical Society, 2004, 8 pages.

Dressman et al., Dissolution testing as a prognostic tool for oral drug absorption: Immediate release dosage forms, Pharmaceutical Research, 1998, 15(1), 11-22.

Etter et al., Solid-state nucleophilic aromatic substitution reaction of a carboxylic acid cocrystal, Tetrahedron Letters, 1989, 30(28), 3617-3620.

Fowler et al., A rational design of molecular materials, Journal of Physical Organic Chemistry, 2000, 13, 850-857.

Kaupp, Organic solid-state reactions with 100% yield, Top. Curr. Chem, 2005, 254, 95-183.

Kaupp et al., Waste-free and facile solid-state protection of diamines, anthranilic acid, diols, and polyols and phenylboronic acid, Chem. Eur. J., 2003, 4156-4160.

Li et al,, Solid-state acid-base interactions in complexes of heterycyclic bases with bicarboxylic acids: Crystallography, hydrogen bond analysis, and 15N NMR Spectroscopy, Journal of American Chemistry Society, 2006, 128, 8199-8210.

MacGillivray et al., Supramolecular control of reactivity in the solid state using linear molecular templates, Journal of American Chemistry Society, 2000, 122, 7817-7818.

Remenar et al., Crystal engineering of novel cocrystals of triazole drug with 1,4-dicarboxylic acids, Journal of American Chemistry Society, 2003, 125, 8456-8457.

Shan et al., Mechanochemistry and co-crystal formation: effect of solvent on reaction kinetics, ChemComm, 2002, 2372-2373.

Tanaka et al., Solvent-free organic synthesis, Chemical Review, 2000, 100, 1025-1074.

Vidal et al., Re-examination of microwave-induced synthesis of phthalimides, Tetrahedron 56, 2000, 5473-5478.

Vishweshwar et al., Pharmaceutical co-crystals, Journal of Pharmaceutical Sciences, 2006, 95(3), 499-516.

Patent Cooperation Treaty, International Search Report issued for PCT/US2008/007129, dated Dec. 22, 2008, 4 pages.

European Patent Office, Supplemental European Search Report for EP 08768204, dated Mar. 25, 2013, 2 pages.

\* cited by examiner

NUTRACEUTICAL CO-CRYSTAL COMPOSITIONS

CROSS-REFERENCE TO RELATED APPLICATIONS

This application is a continuation of U.S. patent application Ser. No. 14/533,255, entitled "NUTRACEUTICAL CO-CRYSTAL COMPOSITIONS", filed on Nov. 5, 2014, which is a continuation of U.S. patent application Ser. No. 12/663,212, entitled "NUTRACEUTICAL CO-CRYSTAL COMPOSITIONS", filed on Apr. 15, 2010, which is the U.S. national stage entry under 35 U.S.C. § 371 of International Patent Application Serial No. PCT/US08/07129, filed on Jun. 6, 2008, which claims the benefit of U.S. Provisional Patent Application Ser. No. 60/942,355 filed Jun. 6, 2007, and the benefit of U.S. Provisional Patent Application Ser. No. 60/982,619, filed Oct. 25, 2007, the contents of all of these prior patent applications being incorporated herein by reference in their entireties.

FIELD OF THE INVENTION

The present invention is generally related to co-crystal compositions containing nutraceuticals. Such compositions may be used in the preparation of (or even as) pharmaceuticals, nutraceuticals, nutritional supplements, food compositions and the like.

BACKGROUND ART

Nutraceuticals are a class of natural product that is attracting increasing attention. Nutraccuticals refer to a food or food component claimed to human health benefits. Nutraccuticals more specifically relate to individual chemicals present in foods and are commonly marketed as dietary supplements. Examples of nutraceuticals include amino acids and amino acid derivatives such as sarcosine, nicotinic acid, pantothenic acid, and gamma-linoleic acid; and purine derivatives, such as xanthines.

Dietary polyphenols are one category of nutraceuticals and represent a wide variety of compounds that occur in fruits, vegetables, wine, tea, extra virgin olive oil, chocolate and other cocoa products. They are mostly derivatives and/or isomers of flavones, isoflavones, flavanols, catechins, and phenolic acids, and exhibit many biologically significant functions, such as protection against oxidative stress, and degenerative diseases. Experimental data indicate that most of these biological actions can be attributed to their intrinsic antioxidant capabilities, and dietary polyphenols are the most abundant antioxidants in human diets. Dietary polyphenols may offer an indirect protection by activating endogenous defense systems and by modulating cellular signaling processes such as nuclear factor-kappa B (NF-κB) activation, activator protein-1 (AP-1) DNA binding, glutathione biosynthesis, phosphoinositide 3 (PI3)-kinase/protein kinase B (Akt) pathway, mitogen-activated protein kinase (MAPK) proteins [extracellular signal-regulated protein kinase (ERK), c-jun N-terminal kinase (JNK) and P38] activation, and the translocation into the nucleus of nuclear factor erythroid 2 related factor 2 (Nrf2) (Han et al. 2007).

Additionally, certain nutraceuticals, namely EGCG and caffeine, have been shown to reduce beta-amyloid levels and plaque formation in transgenic mouse models of Alzheimer's disease (AD). AD is a devastating neurodegenerative disease that currently affects an estimated 4.5 million Americans, costing the United States more than $100 billion annually. Finding a treatment that could delay onset by five years could reduce the number of individuals with AD by nearly 50 percent after 50 years. The nutraceutical quercetin has been reported to have therapeutic effects against neurodegenerative disease in various animal models.

The widespread distribution of flavonoid and other nutraceuticals means that they are ingested in significant quantities by animals. Furthermore, their variety, their relatively low toxicity compared to, for example, alkaloids, and their biological activity means that consumers, food manufacturers, nutraceutical manufacturers, and pharmaceutical companies have become interested in flavonoids for their medicinal properties.

Nutraceuticals can be prepared so as to have a variety of different chemical forms including chemical derivatives or salts. Such nutraceuticals can also be prepared to have different physical forms. For example, the nutraceuticals may be amorphous, may have different crystalline polymorphs, or may exist in different solvation or hydration states. By varying the form of a nutraceutical, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, colour, and compressibility. Accordingly, variation of the crystalline state of a nutraceutical is one of many ways in which to modulate the physical properties thereof.

A co-crystal is a multiple component crystal containing two or more non-identical molecules in which all components are solid under ambient conditions (i.e. 22° Celsius, 1 atmosphere of pressure) when in their pure form. The components comprise a target molecule (i.e., a nutraceutical) and a molecular co-crystal former that coexist in the co-crystal at the molecular level within a single crystal.

Co-crystals that comprise two or more molecules (co-crystal formers) (Almarsson et al., 2004) that are solids under ambient conditions represent a long-known class of compounds (see Wöhler, 1844). However, co-crystals remain relatively unexplored. A Cambridge Structural Database (CSD) (Allen et al., 1993) survey reveals that co-crystals represent less than 0.5% of published crystal structures. Nevertheless, their potential impact upon pharmaceutical (e.g., nutraceutical) formulation (Vishweshwar et al., 2006; Li et al., 2006; Remenar et al., 2003; and Childs et al., 2004) and green chemistry (Anastas et al., 1998) is of topical and growing interest. In particular, the fact that all co-crystal components are solids under ambient conditions has important practical considerations because synthesis of co-crystals can be achieved via solid-state techniques (mochanochemistry)(Shan et al., 2002), and chemists can execute a degree of control over the composition of a co-crystal since they can invoke molecular recognition, especially hydrogen bonding, during the selection of co-crystal formation. Those features distinguish co-crystals from solvates which are another broad and well-known group of multiple component compounds. Solvates are much more widely characterized than co-crystals (e.g., 1652 co-crystals are reported in the CSD versus 10,575 solvates; version 5.27 (May 2006) 3D coordinates, R<0.075, no ions, organics only).

Whereas solid-state organic synthesis represents a well-established area of research (Tanaka et al., 2003; Tanaka et al., 2000; Kaupp et al., 2005), co-crystal controlled solid-state synthesis has been limited to photodimerizations or photopolymerizations (MacGillivray et al., 2000; Fowler et al., 2000) and nucleophilic substitution (Etter et al., 1989). In the case of photodimerizations or photopolymerizations, one co-crystal former typically serves to align or "template" the reactant, which is the other co-crystal former. In the case of the nucleophilic substitution, both co-crystal formers are reactants; although there are examples of solid-state reactions in which the reactive moieties are in the same molecule and therefore generate polymeric structures (Foxman et al., 2000).

It would be advantageous to have new forms of nutraceuticals that have improved properties, in particular, as oral formulations. Specifically, it is desirable to identify improved forms of nutraceuticals that exhibit significantly improved properties including increased aqueous solubility and stability. Further, it is desirable to improve the processability, or preparation of pharmaceutical formulations. For example, needle-like crystal forms or habits of nutraceuticals can cause aggregation, even in compositions where the nutraceutical is mixed with other substances, such that a non-uniform mixture is obtained. It is also desirable to increase or decrease the dissolution rate of nutraceutical-containing pharmaceutical compositions in water, increase or decrease the bioavailability of orally-administered compositions, and provide a more rapid or more delayed onset to therapeutic effect. It is also desirable to have a form of the nutraceutical which, when administered to a subject, reaches a peak plasma level faster or slower, has a longer lasting therapeutic plasma concentration, and higher or lower overall exposure when compared to equivalent amounts of the nutraceutical in its presently-known form. The improved properties discussed above can be altered in a way which is most beneficial to a specific nutraceutical for a specific therapeutic effect.

SUMMARY OF THE INVENTION

Among the various aspects of the invention is the provision of nutraceutical co-crystals, a process for the preparation of such co-crystals, and methods for improving animal health or nutrition by administering such co-crystals (alone or in combination with other compositions or as a component thereof) to a human or other animal. Advantageously, the nutraceutical co-crystals provide improved properties, in particular, as oral formulations. Such properties may include one or more of increased aqueous solubility and stability, improved processability, improved biological activity, improved biological availability, improved dissolution, and improved plasma profile. In addition, the properties may be altered in a way which is most beneficial to a specific nutraceutical for a specific therapeutic effect. These crystalline forms possess a range of desirable properties and may be used as a nutraceutical, as part of a pharmaceutical composition, nutritional supplements, foodstuffs, and the like.

Briefly, therefore, one aspect of the present invention is a composition comprising a co-crystal of a nutraceutical and a co-crystal former wherein the nutraceutical and the co-crystal former are hydrogen bonded to each other. In this embodiment, the nutraceutical is selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hesperitin, and protocatechuic acid, and co-crystal former is selected from the group consisting of pharmaceutically acceptable carbohydrates, amines, amides, sulfonamides, carboxylic acids, sulfonic acids, phenols, polyphenols, aromatic heterocycles, xanthines and alcohols. The co-crystal may or may not contain impurities.

The present invention is further directed to a nutraceutical co-crystal comprising at least one nutraceutical compound and L-ascorbic acid wherein the nutraceutical compound and L-ascorbic acid are hydrogen bonded.

The present invention is further directed to a nutraceutical co-crystal comprising a nutraceutical and a co-crystal former, wherein the nutraceutical is a flavonoid and the co-crystal former is a xanthine.

The present invention is further directed to a nutraceutical co-crystal comprising a nutraceutical and a co-crystal former, wherein the nutraceutical is epigallocatechin-3-gallate, quercetin, or hesperitin, and the co-crystal former is caffeine, theobromine, or theophylline.

The present invention is further directed to a nutraceutical co-crystal comprising combining at least one nutraceutical and at least one co-crystal former and inducing the nutraceutical(s) and the co-crystal former(s) to hydrogen bond with each other.

The present invention is further directed to a pharmaceutical composition comprising a nutraceutical co-crystal and a pharmaceutically acceptable excipient.

The present invention is further directed to a foodstuff or nutritional supplement comprising a nutraceutical co-crystal and another component safe for human consumption.

The present invention is further directed to a method for improving health or nutrition comprising administering a composition comprising a nutraceutical co-crystal.

Other aspects and objects of the invention will be in part apparent and in part pointed out hereinafter.

DETAILED DESCRIPTION OF THE PREFERRED EMBODIMENTS

Figure 1:
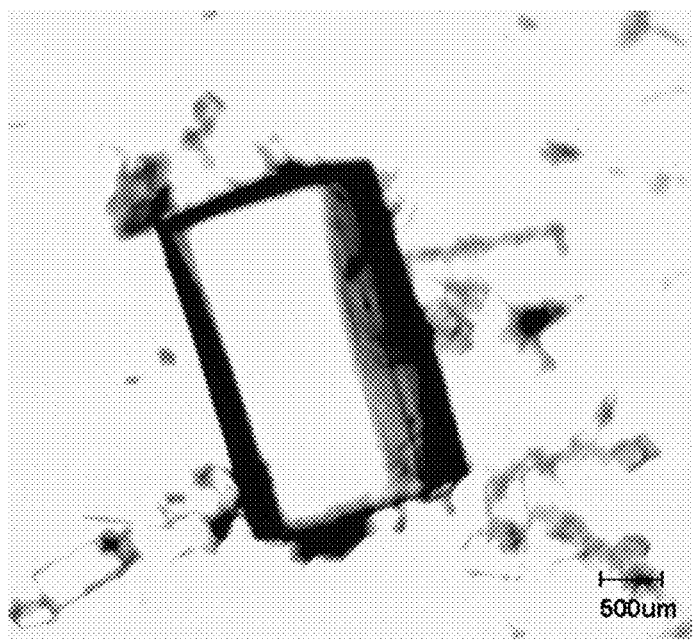
FIG. 1 shows a digital microscopic image of KP05 as described more fully in Example 1.

The present invention is generally directed to co-crystals comprising at least one nutraceutical compound and at least one co-crystal former. These co-crystals may be included in compositions (optionally also including other components such as pharmaceutically acceptable excipients, other nutritional supplements, etc.) having utility as pharmaceuticals, nutraceuticals, nutritional supplements, and foodstuffs. The co-crystals of the present invention, referred to herein as nutraceutical co-crystals, are co-crystals that are formed between a molecular or ionic nutraceutical and a stoichiometric amount of a second molecule (the co-crystal former) that is a solid under ambient conditions (i.e. 22° C., 1 atmosphere of pressure). Although a number of nutraceutical co-crystals are within the ambit of this invention, an example of such nutraceutical co-crystals are co-crystals of flavonoids and xanthines (wherein the flavonoid is the nutraceutical and the xanthine is the co-crystal former).

The nutraceutical co-crystals of the present invention are crystalline material comprised of two or more unique (non-identical) solids at room temperature (i.e. 22° C.) in generally about a stoichiometric ratio, each co-existing in the co-crystal at the molecular level within the single crystal and each containing distinctive physical characteristics, such as structure, melting point and heats of fusion. The co-crystal can be constructed through several modes of molecular recognition including hydrogen-bonding, π(pi)-stacking, guest-host complexation and Van-der-Waals interactions. The co-crystals may include one or more solvate or water molecules in the crystalline lattice. That is, solvates or hydrates of co-crystals, or a co-crystal further comprising a solvent, or water or compound that is a liquid at room temperature, is included in the present invention, but crystalline material comprised of only one solid and one or more liquids (at room temperature) are not included in the present invention. The co-crystals may also be a co-crystal between a co-crystal former (such as L-ascorbic acid) and a salt of a nutraceutical, but the nutraceutical and the co-crystal former (such as L-ascorbic acid) of the present invention are constructed or bonded together through hydrogen bonds. Of the interactions listed above, hydrogen-bonding is believed to be the dominant interaction in the formation of the co-crystal, whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

Accordingly, in a first aspect, the present invention provides a nutraceutical composition comprising a co-crystal of a nutraceutical and a co-crystal former, such that the nutraceutical and co-crystal former are capable of co-crystallizing from a solution phase under crystallization conditions or from the solid-state, for example, through grinding, heating, or through vapor transfer (e.g., co-sublimation). Thus, the nutraceutical co-crystals of the present invention are formed where the nutraceutical and co-crystal former are bonded together through hydrogen bonds. Other non-covalent interactions, including pi-stacking and van der Waals interactions, may also be present.

In an embodiment, non-aqueous, non-solvent impurities may be present in the co-crystal composition. In general, it is preferred that the co-crystal composition contains less than 1% by weight impurities but impurities can represent up to 25% by weight. In certain embodiments, greater degree of purity may be desired; in such instances, it may be preferred that the crystalline material contain less than 0.5% by weight impurities; less than 0.1% by weight impurities; or even less than 0.01% by weight impurities.

In one embodiment, the present invention provides a pharmaceutical co-crystal composition, comprising: a nutraceutical and a co-crystal former, wherein the nutraceutical is a liquid or a solid at room temperature and the co-crystal former is a solid at room temperature, and wherein the nutraceutical and co-crystal former are hydrogen bonded to each other.

It has surprisingly been found that when a nutraceutical and a selected co-crystal former are allowed to form co-crystals, the resulting co-crystals often give rise to improved properties of the nutraceutical, as compared to the nutraceutical in a free form (including free acids, free bases, and zwitterions, hydrates, solvates, etc.), or an acid or base salt thereof particularly with respect to: solubility, dissolution, bioavailability, stability, $C_{max}$, $T_{max}$, processability (including compressibility), longer lasting therapeutic plasma concentration, hygroscopicity, crystallization of amorphous compounds, decrease in form diversity (including polymorphism and crystal habit), change in morphology or crystal habit, etc. For example, a co-crystal form of a nutraceutical is particularly advantageous where the original nutraceutical is practically insoluble or of low solubility in water. Additionally, the co-crystal properties conferred upon the nutraceutical are also useful because the bioavailability of the nutraceutical can be improved and the plasma concentration and/or serum concentration of the nutraceutical can be improved. This is particularly advantageous for orally-administrable formulations. Moreover, the dose response of the nutraceutical can be improved, for example by increasing the maximum attainable response and/or increasing the potency of the nutraceutical by increasing the biological activity per dosing equivalent.

In one embodiment, co-crystal forms comprising nutraceuticals and the co-crystal former L-ascorbic acid (Vitamin C) are prepared and isolated. Particularly, it has been discovered that the hydrogen bonding capabilities of L-ascorbic acid can be used for the crystal engineering of co-crystals with compounds that are zwitterionic and/or have one or more carboxyl (or carboxylate) groups.

Nutraceuticals

In one embodiment, nutraceuticals comprised by the co-crystals of the present invention are zwitterions and/or contain at least one carboxylate (carboxyl) group and include, but are not limited to, vitamins, amino acids and derivative thereof, alkaloids, peptides, flavonoids, steroidals, terpenoids, pharmaceuticals, and hormones or prohormones. The nutraceutical may be provided as a salt or an anion of a salt. In one embodiment, for example, the nutraceutical is nicotinic acid or sarcosine.

Flavonoids are a long and well-known class of natural product that is attracting increasing attention as nutraceuticals and pharmaceuticals. Flavonoids are based upon a group of compounds called chalcones and typically contain a 3-ring structure called flavone. The metabolic pathway in plants affords many derivatives including flavonols, flavan-3-ols, tannins and other polyphenolics. Flavonoids are synthesized and widely distributed in plants and fulfill many functions including pigmentation in flowers, and protection from attack by microbes and insects. The widespread distribution of flavonoids means that they are ingested in significant quantities by animals. Furthermore, their variety, their relatively low toxicity compared to, for example, alkaloids, and their biological activity (they can be anti-allergic, anti-inflammatory, anti-microbial, anti-cancer and they can improve cognitive functions) means that consumers, food manufacturers and pharmaceutical companies have become interested in flavonoids for their medicinal properties. Indeed, the beneficial effects of fruit, vegetables, and tea or even red wine have been attributed to flavonoid compounds. Although many flavonoids are abundant and commercially available they can be hard to purify and crystallize and their solubility can be low.

In one preferred embodiment, therefore, the present invention is directed to nutraceutical co-crystals comprising a flavonoid as the nutraceutical. In this embodiment, for example, the nutraceutical co-crystal may comprise a flavonoid selected from the group consisting of resveratrol, epigallocatechin-3-gallate (EGCG), quercetin, ferulic acid, ellagic acid, hesperitin, and protocatechuic acid. By way of further example, the nutraceutical may be a flavonoid selected from the group consisting of EGCG, ferulic acid, ellagic acid, hesperitin, and protocatechuic acid.

In another preferred embodiment, the nutraceutical may be one of the previously mentioned flavonoid or a nutraceutical selected from a group of nutraceuticals currently believed to possess biological activity. For example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hesperitin, and protocatechuic acid. By way of further example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistin, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hesperitin, and protocatechuic acid.

In general, the co-crystals can include an acid addition salt or base addition salt of a nutraceutical. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g. isopropylamine, trimethyl amine, diethyl amine, tri(isopropyl)amine, tri(n-propyl)amine, ethanolamine, 2-dimethylaminoethanol, tromethamine, lysine, arginine, histidine, procaine, hydrabamine, choline, betaine, ethylenediamine, glucosamine, N-alkylglucamines, theobromine, purines, piperazine, piperidine, morpholine, and N-ethylpiperidine).

Co-Crystal Formers

In general, the co-crystal former is any co-crystal former that may be safely administered to humans. Such compositions may be identified on the GRAS list (also known as the "Generally Recognized As Safe" list) or the EAFUS list (also known as the "Everything Added to Food in the United States" list) maintained by the U.S. Food and Drug Administration or excipients approved for pharmaceutical use. More typically, however, the co-crystal former will be a pharmaceutically acceptable carbohydrate, amine, amide, sulfonamide, carboxylic acid, sulfonic acid, phenolic, polyphonic, aromatic heterocycle, xanthine (or a derivative thereof), or alcohol. By way of example, in one embodiment, the co-crystal former is L-ascorbic acid (also known as vitamin C). In this embodiment, the nutraceutical co-crystal comprises at least one nutraceutical compound and L-ascorbic acid wherein the nutraceutical compound and L-ascorbic acid are hydrogen bonded. By way of further example, in one embodiment, the co-crystal former is xanthine or a derivative thereof (such as caffeine, paraxanthine, theophylline or theobromine), collectively referred to as xanthines. In this embodiment, the nutraceutical co-crystal comprises at least one nutraceutical compound and a xanthine (i.e., xanthine or a derivative thereof such as caffeine) wherein the nutraceutical compound and the xanthine are hydrogen bonded.

In one preferred embodiment, the co-crystal former will be selected from a more narrow group of compositions. In this embodiment, for example, the co-crystal former will be selected from the group consisting of 1,5-napthalene-disulfonic acid, 1-hydroxy-2-naphthoic acid, 4-aminobenzoic acid, 4-aminopyridine, 4-chlorobenzene-sulfonic acid, 4-ethoxyphenyl urea, 7-oxo-DHEA, acesulfame, acetohydroxamic acid, adenine, adipic acid, alanine, allopurinaol, arginine, ascorbic acid, asparagine, aspartic acid, benzenesulfonic acid, benzoic acid, caffeine, camphoric acid, capric acid, chrysin, cinnamic acid, citric acid, clemizole, cyclamic acid, cysteine, dimethylglycine, D-ribose, fumaric acid, galactaric acid, genistein, gentisic acid, glucamine N-methyl, gluconic acid, glucosamine, glucuronic acid, glutamic acid, glutamine, glutaric acid, glycine, glycolic acid, hippuric acid, histidine, hydroquinone, imidazole, ipriflavone, isoleucine, lactobionic acid, lauric acid, leucine, lysine, maleic acid, malic acid, malonic acid, mandelic acid, methionine, nicotinamide, nicotinic acid, orotic acid, oxalic acid, palmitic acid, pamoic acid, phenylalanine, piperazine, procaine, proline, p-toluenesulfonic acid, pyridoxamine, pyridoxine (4-pyridoxic acid), pyroglutamic acid, quercetin, resveratrol, saccharin, salicylic acid, salicylic acid 4-amino, sebacic acid, serine, stearic acid, succinic acid, tartaric acid, threonine, TRIS, tryptophan, tyrosine, urea, valine, Vitamin K5, xylitol, L-ascorbic acid (Vitamin C), gallic acid, maleic acid, iso-nicotinamide, nicotinic acid, iso-nicotinic acid, theobromine, theophylline, caprolactam, lactose, glucose, and sucrose.

In another preferred embodiment, the co-crystal former may be selected from the group consisting of 1,5-napthalene-disulfonic acid, l-hydroxy-2-naphthoic acid, 4-aminobenzoic acid, 4-aminopyridine, 4-chlorobenzene-sulfonic acid, 4-ethoxyphenyl urea, 7-oxo-DHEA, acesulfame, acetohydroxamic acid, adenine, adipic acid, alanine, allopurinaol, arginine, ascorbic acid, asparagine, aspartic acid, benzenesulfonic acid, benzoic acid, caffeine, camphoric acid, capric acid, chrysin, cinnamic acid, citric acid, clemizole, cyclamic acid, cysteine, dimethylglycine, D-ribose, fumaric acid, galactaric acid, genistein, gentisic acid, glucamine N-methyl, gluconic acid, glucosamine, glucuronic acid, glutamic acid, glutamine, glutaric acid, glycine, glycolic acid, hippuric acid, histidine, hydroquinone, imidazole, ipriflavone, isoleucine, lactobionic acid, lauric acid, leucine, lysine, maleic acid, malic acid, malonic acid, mandelic acid, methionine, nicotinamide, nicotinic acid, orotic acid, oxalic acid, palmitic acid, pamoic acid, phenylalanine, piperazine, procaine, proline, p-toluenesulfonic acid, pyridoxamine, pyridoxine (4-pyridoxic acid), pyroglutamic acid, quercetin, resveratrol, saccharin, salicylic acid, salicylic acid 4-amino, sebacic acid, serine, stearic acid, succinic acid, tartaric acid, threonine, TRIS, tryptophan, tyrosine, urea, valine, Vitamin K5, xylitol, caffeine, paraxanthine, theobromine, theophylline, caprolactam, lactose, glucose and sucrose.

In yet another preferred embodiment, the co-crystal former is selected from the group consisting of L-ascorbic acid (vitamin C), salicylic acid, citric acid, gallic acid, maleic acid, malic acid, tartaric acid, nicotinamide, iso-nicotinamide, nicotinic acid, iso-nicotinic acid, caffeine, theobromine, theophylline, caprolactam, lactose, glucose and sucrose.

Nutraceutical Co-Crystals and Compositions

The nutraceutical co-crystals of the present invention may comprise at least one of the previously identified nutraceuticals and at least one of the previously identified co-crystal formers.

In one preferred embodiment, the nutraceutical co-crystal comprises a flavonoid as the nutraceutical and a xanthine as the co-crystal former. By way of example, the nutraceutical co-crystal may comprise a flavonoid selected from the group consisting of resveratrol, epigallocatechin-3-gallate (EGCG), quercetin, ferulic acid, ellagic acid, hesperitin, and protocatechuic acid, and a xanthine as the co-crystal fomer. By way of further example, the nutraceutical co-crystal may comprise a flavonoid selected from the group consisting of EGCG, ferulic acid, ellagic acid, hesperitin, and protocatechuic acid, and a xanthine. By way of further example, in each of these embodiments in which the nutraceutical is a flavonoid, generally, or a flavonoid selected from either of these specified groups, the xanthine co-crystal former may be caffeine, paraxanthine, theophylline or theobromine. By way of further example, in each of these embodiments in which the nutraceutical is a flavonoid, generally, or a flavonoid selected from one of these specified groups, the xanthine co-crystal former may be caffeine, theophylline or theobromine. By way of further example, in each of these embodiments in which the nutraceutical is a flavonoid, generally, or a flavonoid selected from one of these specified groups, the xanthine co-crystal former may be caffeine.

In another preferred embodiment, the nutraceutical co-crystal comprises L-ascorbic acid as the co-crystal former and at least one of the previously identified nutraceuticals. By way of example, the nutraceutical co-crystal may comprise L-ascorbic acid as a co-crystal former and a nutraceutical comprising a carboxylate (carboxyl) group. More specifically, the nutraceutical co-crystal may comprise L-ascorbic acid as a co-crystal former and a nutraceutical selected from the group consisting of vitamins, amino acids and derivative thereof, alkaloids, peptides, flavonoids, steroidals, terpenoids, hormones and prohormones. In one embodiment, for example, the co-crystal former is L-ascorbic acid and the nutraceutical is nicotinic acid or sarcosine. By way of further example, the nutraceutical co-crystal may comprise L-ascorbic acid as a co-crystal former and a flavonoid as the nutraceutical. By way of further example, the nutraceutical co-crystal may comprise L-ascorbic acid as a co-crystal former and a flavonoid selected from the group consisting of resveratrol, EGCG, quercetin, ferulic acid, ellagic acid, hesperitin, and protocatechuic acid as the nutraceutical. By way of further example, the nutraceutical co-crystal may comprise L-ascorbic acid as a co-crystal former and a flavonoid selected from the group consisting of EGCG, ferulic acid, ellagic acid, hesperitin, and protocatechuic acid as the nutraceutical.

In further embodiments, the combination of the nutraceutical and co-crystal former is, in combination, selected from the combinations represented by each individual row, in the following Table:

| Nutraceutical | Co-crystal Former |
| --- | --- |
| Resveratrol | L-ascorbic acid (vitamin C) |
| Resveratrol | salicylic acid |
| Resveratrol | citric acid |
| Resveratrol | gallic acid |
| Resveratrol | maleic acid |
| Resveratrol | malic acid |
| Resveratrol | tartaric acid |
| Resveratrol | Nicotinamide |
| Resveratrol | iso-nicotinamide |
| Resveratrol | nicotinic acid |
| Resveratrol | iso-nicotinic acid |
| Resveratrol | Caffeine |
| Resveratrol | Theobromine |
| Resveratrol | Theophylline |
| Resveratrol | Caprolactam |
| Resveratrol | Lactose |
| Resveratrol | Glucose |
| Resveratrol | Sucrose |

-continued

| Nutraceutical | Co-crystal Former |
|---|---|
| EGCG | L-ascorbic acid (vitamin C) |
| EGCG | salicylic acid |
| EGCG | citric acid |
| EGCG | gallic acid |
| EGCG | maleic acid |
| EGCG | malic acid |
| EGCG | tartaric acid |
| EGCG | Nicotinamide |
| EGCG | iso-nicotinamide |
| EGCG | nicotinic acid |
| EGCG | iso-nicotinic acid |
| EGCG | Caffeine |
| EGCG | Theobromine |
| EGCG | Theophylline |
| EGCG | Caprolactam |
| EGCG | Lactose |
| EGCG | Glucose |
| EGCG | Sucrose |
| Quercetin | L-ascorbic acid (vitamin C) |
| Quercetin | salicylic acid |
| Quercetin | citric acid |
| Quercetin | gallic acid |
| Quercetin | maleic acid |
| Quercetin | malic acid |
| Quercetin | tartaric acid |
| Quercetin | Nicotinamide |
| Quercetin | iso-nicotinamide |
| Quercetin | nicotinic acid |
| Quercetin | iso-nicotinic acid |
| Quercetin | Caffeine |
| Quercetin | Theobromine |
| Quercetin | Theophylline |
| Quercetin | Caprolactam |
| Quercetin | Lactose |
| Quercetin | Glucose |
| Quercetin | Sucrose |
| ferulic acid | L-ascorbic acid (vitamin C) |
| ferulic acid | salicylic acid |
| ferulic acid | citric acid |
| ferulic acid | gallic acid |
| ferulic acid | maleic acid |
| ferulic acid | malic acid |
| ferulic acid | tartaric acid |
| ferulic acid | Nicotinamide |
| ferulic acid | iso-nicotinamide |
| ferulic acid | nicotinic acid |
| ferulic acid | iso-nicotinic acid |
| ferulic acid | Caffeine |
| ferulic acid | Theobromine |
| ferulic acid | Theophylline |
| ferulic acid | Caprolactam |
| ferulic acid | Lactose |
| ferulic acid | Glucose |
| ferulic acid | Sucrose |
| ellagic acid | L-ascorbic acid (vitamin C) |
| ellagic acid | salicylic acid |
| ellagic acid | citric acid |
| ellagic acid | gallic acid |
| ellagic acid | maleic acid |
| ellagic acid | malic acid |
| ellagic acid | tartaric acid |
| ellagic acid | Nicotinamide |
| ellagic acid | iso-nicotinamide |
| ellagic acid | nicotinic acid |
| ellagic acid | iso-nicotinic acid |
| ellagic acid | Caffeine |
| ellagic acid | Theobromine |
| ellagic acid | Theophylline |
| ellagic acid | Caprolactam |
| ellagic acid | Lactose |
| ellagic acid | Glucose |
| ellagic acid | Sucrose |
| Hesperitin | L-ascorbic acid (vitamin C) |
| Hesperitin | salicylic acid |
| Hesperitin | citric acid |
| Hesperitin | gallic acid |
| Hesperitin | maleic acid |
| Hesperitin | malic acid |
| Hesperitin | tartaric acid |
| Hesperitin | Nicotinamide |
| Hesperitin | iso-nicotinamide |
| Hesperitin | nicotinic acid |
| Hesperitin | iso-nicotinic acid |
| Hesperitin | Caffeine |
| Hesperitin | Theobromine |
| Hesperitin | Theophylline |
| Hesperitin | Caprolactam |
| Hesperitin | Lactose |
| Hesperitin | Glucose |
| Hesperitin | Sucrose |
| protocatechuic acid | L-ascorbic acid (vitamin C) |
| protocatechuic acid | salicylic acid |
| protocatechuic acid | citric acid |
| protocatechuic acid | gallic acid |
| protocatechuic acid | maleic acid |
| protocatechuic acid | malic acid |
| protocatechuic acid | tartaric acid |
| protocatechuic acid | Nicotinamide |
| protocatechuic acid | iso-nicotinamide |
| protocatechuic acid | nicotinic acid |
| protocatechuic acid | iso-nicotinic acid |
| protocatechuic acid | Caffeine |
| protocatechuic acid | Theobromine |
| protocatechuic acid | Theophylline |
| protocatechuic acid | Caprolactam |
| protocatechuic acid | Lactose |
| protocatechuic acid | Glucose |
| protocatechuic acid | Sucrose |

In addition to those specific combinations identified in the table, in one embodiment the nutraceutical co-crystal comprises sarcosine and L-ascorbic acid. In another embodiment, the nutraceutical co-crystal comprises L-ascorbic acid and nicotinic acid. In another embodiment, the nutraceutical co-crystal is a hemihydrate of a co-crystal comprising ferulic acid and baclofen. In another embodiment, the nutraceutical co-crystal is a hemihydrate of a co-crystal comprising gallic acid and caffeine. In another embodiment, the nutraceutical co-crystal is a co-crystal comprising gallic acid and caffeine. In another embodiment, the nutraceutical co-crystal is a trihydrate of a co-crystal comprising gallic acid and nicotinic acid. In another embodiment, the nutraceutical co-crystal is a hydrate of a co-crystal comprising gallic acid and theobromine. In another embodiment, the present invention provides a co-crystal of L-ascorbic acid and nicotinamide. In another embodiment, the nutraceutical co-crystal is a co-crystal of L-ascorbic acid and iso-nicotinamide. In another embodiment, the nutraceutical co-crystal is an ethanol solvate of a co-crystal of L-ascorbic acid and nicotinamide. In another embodiment, the nutraceutical co-crystal is a hydrate of a co-crystal comprising EGCG and iso-nicotinamide. In another embodiment, the nutraceutical co-crystal is a hydrate of a co-crystal comprising ellagic acid and theophylline. In another embodiment, the nutraceutical co-crystal is a co-crystal comprising citric acid and iso-nicotinamide. In another embodiment, the nutraceutical co-crystal is a co-crystal of protocatechuic acid and ε-caprolactam. In another embodiment, the nutraceutical co-crystal is a co-crystal of protocatechuic acid and iso-nicotinamide.

Although it is generally preferred that the nutraceutical co-crystal comprise a single nutraceutical and a single co-crystal former, the nutraceutical co-crystals may comprise more than one nutraceutical and/or more than one co-crystal former. For example, two, three, four, five, or more co-crystal formers can be incorporated in a co-crystal with a single nutraceutical. Alternatively, two or more nutraceuticals can be incorporated in a co-crystal with a single co-crystal former. Alternatively, two or more co-crystal formers can be incorporated into a co-crystal with two or more nutraceuticals. In each such instance, however, the nutraceutical(s) and the co-crystal former(s) are bound together via hydrogen bonds.

Some of the nutraceuticals and co-crystal formers of the present invention have one or more chiral centers and may exist in a variety of stereoisomeric configurations. As a consequence of these chiral centers, several nutraceuticals and co-crystal formers of the present invention occur as racemates, mixtures of enantiomers and as individual enantiomers, as well as diastereomers and mixtures of diastereomers. All such racemates, enantiomers, and diastereomers are within the scope of the present invention including, for example, cis- and trans-isomers, R- and S-enantiomers, and (D)- and (L)-isomers. Co-crystals of the present invention can include isomeric forms of either the nutraceutical or the co-crystal former or both. Isomeric forms of nutraceuticals and co-crystal formers include, but are not limited to, stereoisomers such as enantiomers and diastereomers. In one embodiment, a co-crystal can comprise a racemic nutraceutical and/or co-crystal former. In another embodiment, a co-crystal can comprise an enantiomerically pure nutraceutical and/or co-crystal former. In another embodiment, a co-crystal can comprise a nutraceutical or a co-crystal former with an enantiomeric excess of about 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value. Several non-limiting examples of stereoisomeric co-crystal formers include tartaric acid and malic acid.

Co-crystals, solvates, and polymorphs comprising enantiomerically pure components (e.g., nutraceutical or co-crystal former) can give rise to chemical and/or physical properties which are modulated with respect to those of the corresponding co-crystal comprising a racemic component. A co-crystal comprising an enantiomerically pure component can give rise to a modulation of, for example, activity, bioavailability, or solubility, with respect to the corresponding co-crystal comprising a racemic component.

In one embodiment, a composition of the present invention comprises a nutraceutical co-crystal in combination with one or more additional components selected from the EAFUS list, the GRAS list, a pharmaceutically active ingredient, and/or a pharmaceutically acceptable excipient. Thus, for example, the composition may comprise an enantiomerically pure nutraceutical and/or co-crystal former wherein the bioavailability is modulated with respect to the racemic co-crystal. In another embodiment, the composition comprises an enantiomerically pure nutraceutical and/or co-crystal former wherein the activity is modulated with respect to the racemic co-crystal. In another embodiment, the composition comprises an enantiomerically pure nutraceutical and/or co-crystal former wherein the solubility is modulated with respect to the racemic co-crystal.

In another embodiment, a composition can be formulated to contain the nutraceutical in co-crystal form as micronized or nano-sized particles. More specifically, another embodiment couples the processing of the nutraceutical, e.g., resveratrol, quercetin, EGCG ferulic acid, ellagic acid, hesperitin, or protocatechuic acid to a co-crystal form with the process of making a controlled particle size for manipulation into a pharmaceutical dosage form. This embodiment combines two processing steps into a single step via techniques such as, but not limited to, grinding, alloying, or sintering (i.e., heating a powder mix). The coupling of these processes overcomes a serious limitation of having to isolate and store the bulk nutraceutical that is required for a formulation, which in some cases can be difficult to isolate (e.g., amorphous, chemically or physically unstable).

In addition, the present invention provides a pharmaceutical, foodstuff, and nutraceutical compositions comprising the nutraceutical co-crystals, as described above, as an active ingredient. Such compositions can be used for prevention or therapy of various diseases. For example, such compositions containing EGCG may be based on its antioxidant effects. It is useful for treatment or prevention of diseases including, but not limited to: a neurodegenerative disease or condition such as Alzheimer's disease; an upper respiratory disease, such as one caused by an infection; a dementia, such as AIDS-dementia; an oncological disorder, such as cancer; inflammatory or auto-immune diseases, such as rheumatoid arthritis or diabetic neuropathies; or a disease or condition caused by an infection by virus or bacteria.

The active agent prepared according to the present invention may thus be formulated into any suitable composition form for administration to a human or non-human animal patient.

The composition may consist of the active agent alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier must be acceptable in the sense of being compatible with the other ingredients of the formulation and not injurious to the patient.

Excipients employed in the compositions of the present invention can be solids, semi-solids, liquids or combinations thereof. Preferably, the excipients are solids. Compositions of the invention containing excipients can be prepared by any known technique that comprises, for example, admixing an excipient with the nutraceutical co-crystal. A pharmaceutical, foodstuff or nutraceutical composition of the invention contains a desired amount of the nutraceutical co-crystal and, optionally, an active pharmaceutical ingredient ("API") per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the nutraceutical co-crystal, such as tablets or capsules.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Coloreon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crystal of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents as excipients. Such wetting agents are preferably selected to maintain the crystal in close association with water, a condition that is believed to improve bioavailability of the composition. Such wetting agents can also be useful in solubilizing or increasing the solubility of crystals.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

The composition may, for example, be a pharmaceutical composition (medicament), a foodstuff, food supplement or beverage. The terms "foodstuff", "food supplement", and "beverage" used herein have the normal meanings for those terms, and are not restricted to pharmaceutical preparations. The appropriate pharmaceutical or edible grade of ingredients will be used, according to the desired composition form.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier, and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent. Formulations preferably comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose scaled containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

In one embodiment, the pharmaceutical compositions of the invention can be administered locally to the area in need of treatment; such local administration can be achieved, for example, by local infusion during surgery, by injection, or by means of a catheter. In another embodiment, a compound or composition of the invention is administered in a manner so as to achieve peak concentrations of the active compound at sites of the disease. Peak concentrations at disease sites can be achieved, for example, by intravenously injecting of the agent, optionally in saline, or orally administering, for example, a tablet, capsule or syrup containing the active ingredient.

Pharmaceutical formulations of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the pathology being treated, the subject being treated, and the efficacy and toxicity of the agent. Similarly, suitable dosage formulations and methods of administering the agents can be readily determined by those of ordinary skill in the art.

Nutraceutical Co-Crystal Preparation

In general, the nutraceutical co-crystal is formed by intimate contact of the nutraceutical and the co-crystal former. This may involve grinding or milling the two solids together or melting one or both components and allowing them to recrystallize. The use of a granulating liquid may improve or may impede co-crystal formation. Non-limiting examples of tools useful for the formation of co-crystals may include, for example, an extruder or a mortar and pestle. Further, contacting the nutraceutical with the co-crystal former may also involve either solubilizing the nutraceutical and adding the co-crystal former, or solubilizing the co-crystal former and adding the nutraceutical. Crystallization conditions are applied to the nutraceutical and co-crystal former. This may entail altering a property of the solution, such as pH or temperature and may require concentration of the solute, usually by removal of the solvent, typically by drying the solution. Solvent removal results in the concentration of both nutraceutical and co-crystal former increasing over time so as to facilitate crystallization. For example, evaporation, cooling, co-sublimation, or the addition of an antisolvent may be used to crystallize co-crystals. In another embodiment, a slurry comprising a nutraceutical and a co-crystal former is used to form co-crystals. Once the solid phase comprising any crystals is formed, this may be tested as described herein.

In one embodiment, the use of an excess (more than 1 molar equivalent for a 1:1 co-crystal) of a co-crystal former has been shown to drive the formation of stoichiometric co-crystals. For example, co-crystals with stoichiometries of 1:1, 2:1, or 1:2 can be produced by adding co-crystal former in an amount that is 2, 3, 4, 5, 6, 7, 8, 9, 10, 15, 20, 25, 50, 75, 100 times or more than the stoichiometric amount for a given co-crystal. Such an excessive use of a co-crystal former to form a co-crystal can be employed in solution or when grinding a nutraceutical and a co-crystal former to drive co-crystal formation.

In another alternative embodiment, an ionic liquid may be employed as a medium to form the co-crystal, and to crystallize other forms in addition to co-crystals (e.g., salts, solvates, free acid, free base, zwitterions, etc.). This medium is useful, for example, where the above methods do not work or are difficult or impossible to control. Several non-limiting examples of ionic liquids useful in co-crystal formation are: 1-butyl-3-methylimidazolium lactate, l-ethyl-3-methylimidazolium lactate, and 1-butylpyridinium hexafluorophosphate.

In another embodiment, the nucleation and crystallization behavior of the nutraceutical, the co-crystal former (e.g. L-ascorbic acid), or both, may be affected by the solvent. One factor that may affect nucleation and crystallization includes the ability of the solvent to accept or donate hydrogen bonds. Another factor involved in selecting a solvent is the temperature at which dissolution occurs. High temperature dissolution can cause nutraceutical and/or co-crystal former degradation, can release toxic fumes, and is energy intensive. It is generally preferred for dissolution to occur at a temperature less than about 200° C., 150° C., 100° C., 50° C., 40° C., or even 30° C. Other factors to consider when selecting a solvent is the ability of the nutraceutical and/or co-crystal former to nucleate in that solvent, nutraceutical stability in the solvent, the co-crystal growth rate in the solvent, and the quality of co-crystals that grow in the solvent. Thus, in one embodiment, a number of solvents may be tested in a co-crystal screening procedure in order to determine solvents that promote the preferred crystallization behavior, purity, and yield of the co-crystals.

In general, any solvent into which the nutraceutical and co-crystal former (e.g. L-ascorbic acid) are soluble and stable are suitable for use in the present invention. Typical solvents and cosolvents include water, alcohols, and mixtures thereof. Preferred alcohols have between about 1 and about 10 carbon atoms, may be cyclic or aliphatic, may be saturated or unsaturated, and may be branched or straight-chained. Typical alcohols suitable for use in the present invention include methanol, ethanol, propanol, isopropanol, n-butanol, sec-butanol, tert-butanol, n-pentanol, 2-pentanol, 1-hepten-3-ol and 1-octen-3-ol. Examples of other solvents include methylene chloride, acetonitrile, acetone, cyclohexane, toluene, iso-octane, and mixtures thereof optionally in combination with water and/or alcohol.

In one embodiment, a single solvent system is used for nutraceutical and L-ascorbic acid dissolution. Such a system facilitates solvent recovery and reuse because a recovered solvent purification step is typically not required. In a second embodiment a miscible mixed solvent system could be used with the solvents selected to maximize crystallization rate, yield and purity. For example, L-ascorbic acid could be dissolved in water into which it is freely soluble. Nicotinic acid could be dissolved in ethanol into which it is freely soluble, but L-ascorbic acid has limited solubility in ethanol. L-ascorbic acid solubility in the combined ethanol-water solvent should be reduced thereby promoting crystallization. In another embodiment, an immiscible mixed solvent system could be used. For example, a nutraceutical solvent could be selected that is immiscible with the L-ascorbic acid solvent. Upon combining, the boundaries of the two solutions would come in contact with one another at the interface region between the two solutions. Mixing would occur in the interface region but not outside of it. Thus, on the nutraceutical side of the interface, there would be substantially no L-ascorbic acid beyond the interface and, likewise, on the L-ascorbic acid side of the interface, there would be substantially no nutraceutical beyond the interface. Where the solutions mix in the interface region, there would be a gradient of concentrations ranging from pure nutraceutical in solution to pure L-ascorbic acid in solution with a range of concentrations in between. It is believed that high purity co-crystals could be prepared with this embodiment.

The prepared co-crystals can be isolated by solid-liquid separation means known in the art including filtration and centrifugation. In one embodiment, the crystals can be optionally purified by washing with a solvent. The collected co-crystals can further be dried by means known in the art such as fluidized bed dryers and tray dryers. The crystals can be further subjected to size reduction operations (such as milling) and/or size classification operations (such as sieving) to yield co-crystals having a desired particle size profile and distribution.

It is further believed that the dissolution rate of a co-crystal as measured in simulated gastric fluid (SGF) or simulated intestinal fluid (SIF) (see Dressman J B, et al., Pharm Res. (1998) January; 15(1): 11-22) would be increased by as much as 10, 50, or even 100%, or by an even greater amount, e.g. 2, 5, 10, 50, or even 200 fold greater as compared to the free form or salt form in the same solution.

It is still further believed that the co-crystals of the present invention would be stable such that when evaluated using standard stability or accelerated stability protocols at temperatures of up to about 40° C. for up to 2 years or at about 60° C. for 4 weeks, nutraceutical purity is 99.8%, 99.9% or greater.

The nutraceutical co-crystals obtained as a result of one or more of the above processes or techniques may be readily incorporated into a pharmaceutical composition by conventional means. Pharmaceutical compositions in general are discussed in further detail elsewhere in this application and may further comprise a pharmaceutically-acceptable diluent, excipient or carrier.

Assaying the solid phase for the presence of co-crystals of the nutraceutical and the co-crystal former may be carried out by conventional methods known in the art. For example, it is convenient and routine to use powder X-ray diffraction techniques to assess the presence of co-crystals. This may be effected by comparing the diffractograms of the nutraceutical, the crystal former and putative co-crystals in order to establish whether or not true co-crystals have been formed. Other techniques, used in an analogous fashion, include differential scanning calorimetry (DSC), Fourier Transform infrared spectrophotometry analysis (FT-IR), thermogravimetric analysis (TGA), and Raman spectroscopy. Single crystal X-ray diffraction is especially useful in identifying co-crystal structures.

Definitions

The term "co-crystal" as used herein means a crystalline material comprised of two or more unique solids at room temperature (22° C.), each containing distinctive physical characteristics, such as structure, melting point and heats of fusion, with the exception that, if specifically stated, the nutraceutical may be a liquid at room temperature. The co-crystals of the present invention comprise a co-crystal former hydrogen-bonded (H-bonded) to a nutraceutical. The co-crystal former may be H-bonded directly to the nutraceutical or may be H-bonded to an additional molecule which is bound to the nutraceutical. The additional molecule may be H-bonded to the nutraceutical or bound ionically or covalently to the nutraceutical. The additional molecule could also be a different nutraceutical. Solvates or hydrates of nutraceutical compounds that do not further comprise a co-crystal former are not co-crystals according to the present invention. The co-crystals may however, include one or more solvate or water molecules in the crystalline lattice. That is, a solvate or hydrate of a co-crystal, or a co-crystal further comprising a solvent or water or compound that is a liquid at room temperature, is a co-crystal according to the present invention, but crystalline material comprised of only one solid and one or more liquids (at room temperature) are not co-crystals for purposes of the present invention, with the previously noted exception of specifically stated liquid nutraceuticals. The co-crystals may also be a co-crystal between a co-crystal former and a salt of a nutraceutical, but the nutraceutical and the co-crystal former of the present invention are constructed or bonded together through hydrogen bonds. Other modes of molecular recognition may also be present including, pi-stacking, guest-host complexation and van der Waals interactions. Of the interactions listed above, hydrogen bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

The term "nutraceutical co-crystal" as used herein means a multiple component crystalline solid in which all components are solid under ambient conditions (i.e. 22° Celsius, 1 atmosphere of pressure) when in their pure form. These components co-exist as a stoichiometric ratio of a molecule or ion (the co-crystal former) and a nutraceutical, and the co-crystal former and the nutraceutical are bonded together through supramolecular synthons such as a hydrogen bond.

For purposes of the present invention, the chemical and physical properties of a nutraceutical in the form of a co-crystal may be compared to a reference compound that is the same nutraceutical in a different form. The reference compound may be specified as a free form, or more specifically, a free acid, free base, or zwitterion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, propionic, pyruvic, malanic, succinic, malic, maleic acid, fumaric, tartaric, citric, benzoic, methanesulfonic, ethanesulfonic, stearic or lactic acid addition salt; an anhydrate or hydrate of a free form or salt, or more specifically, for example, a hemihydrate, monohydrate, dihydrate, trihydrate, quadrahydrate, pentahydrate, sesquihydrate; or a solvate of a free form or salt. For example, the reference compound for a nutraceutical in salt form co-crystallized with a co-crystal former can be the nutraceutical salt form. Similarly, the reference compound for a free acid nutraceutical co-crystallized with a co-crystal former can be the free acid nutraceutical. The reference compound may also be specified as crystalline or amorphous. The reference compound may also be specified as the most stable polymorph known of the specified form of the reference compound.

As used herein and unless otherwise noted, the term "racemic co-crystal" refers to a co-crystal which is comprised of an equimolar mixture of two enantiomers of the nutraceutical, the co-crystal former, or both. For example, a co-crystal comprising a stereoisomeric nutraceutical and a non-stereoisomeric co-crystal former is a "racemic co-crystal" when there is present an equimolar mixture of the nutraceutical enantiomers. Similarly, a co-crystal comprising a non-stereoisomeric nutraceutical and a stereoisomeric co-crystal former is a "racemic co-crystal" when there is present an equimolar mixture of the co-crystal former enantiomers. In addition, a co-crystal comprising a stereoisomeric nutraceutical and a stereoisomeric co-crystal former is a "racemic co-crystal" when there is present an equimolar mixture of the nutraceutical enantiomers and of the co-crystal former enantiomers.

As used herein and unless otherwise noted, the term "enantiomerically pure co-crystal" refers to a co-crystal which is comprised of a stereoisomeric nutraceutical or a stereoisomeric co-crystal former or both where the enantiomeric excess of the stereoisomeric species is greater than or equal to about 90 percent.

EXAMPLES

A. General Methods for the Preparation of Co-Crystals
a) High Throughput Crystallization High throughput crystallization may be used, comprising a sequence of automated, integrated high throughput robotic stations capable of rapid generation, identification and characterization of polymorphs, salts, and co-crystals of nutraceuticals and nutraceutical candidates. Worksheet generation and combinatorial mixture design is carried out using proprietary design software. Typically, a nutraceutical or a nutraceutical candidate is dispensed from an organic solvent into tubes and dried under a stream of nitrogen. Salts and/or co-crystal formers may also be dispensed and dried in the same fashion. Water and organic solvents may be combinatorially dispensed into the tubes using a multi-channel dispenser. Each tube in a 96-tube array is then sealed within 15 seconds of combinatorial dispensing to avoid solvent evaporation. The mixtures are then rendered supersaturated by heating to 70° C. for 2 hours followed by a 1° C./minute cooling ramp to 5° C. Optical checks are then conducted to detect crystals and/or solid material. Once a solid has been identified in a tube, it is isolated through aspiration and drying. Raman spectra are then obtained on the solids and cluster classification of the spectral patterns is performed using proprietary software (QForm™).

b) Crystallization from Solution

Co-crystals may be obtained by dissolving the separate components in a solvent and adding one to the other. The co-crystal may then precipitate or crystallize as the solvent mixture is evaporated slowly or if the solution is cooled. The co-crystal may also be obtained by dissolving the two components in the same solvent or a mixture of solvents. The ratio of the co-crystal formers in solution will not necessarily correspond to the ratio of the co-crystal formers in the resulting co-crystal.

c) Crystallization from the Melt

A co-crystal may be obtained by melting the two components together and allowing recrystallization to occur. In some cases, an anti-solvent may be added to facilitate crystallization.

d) Thermal Microscopy

A co-crystal may be obtained by melting the higher melting component on a glass slide and allowing it to recrystallize. The second component is then melted and is also allowed to recrystallize. The co-crystal may form as a separated phase/band in between the eutectic bands of the two original components.

e) Mixing and/or Grinding

A co-crystal may be obtained by mixing or grinding two components together in the solid state with our without the presence of a liquid or solvent.

B. Analytical Methods

A. X-ray Powder Diffraction

A powder X-ray diffraction pattern for the samples was obtained using a Bruker AXS D8 diffractometer. For the PXRD analysis, the acquisition parameters were as follows: source was Cu with a K line at 1.5406.ANG.; x-y stage was manual; collimator size was 0.3 or 0.8 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 or 0.8 mm collimator, the collection time was 60 minutes; the temperature was room temperature; and the heater was not used. The sample was presented to the X-ray source on a rotating disc.

In addition, the analysis parameters were as follows: the integration 2-theta range was 2-40 or 60 degrees; the integration chi range was 0-360 degrees; the number of chi segments was 1; the step size used was 0.02; the integration utility was cylint; normalization was used; dark counts were 8; omega offset was 180; and chi and phi offsets were 0.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator.

For PXRD data herein, each composition of the present invention may be characterized by any one, any two, any three, any four, any five, any six, any seven, or any eight or more of the 2θ angle peaks.

B. DSC Analysis

DSC analysis of the samples was performed using a 2920 Differential Scanning Calorimeter (TA Instruments, New Castle, Del., U.S.A.), which uses Advantage for QW-Series, version 1.0.0.78, Thermal Advantage Release 2.0 ([8]2001 T A Instruments-Water LLC). In addition, the analysis software used was Universal Analysis 2000 for Windows 95/95/2000/NT, version 3.1 E; Build 3.1.0.40 ([8]2001 T A Instruments-Water LLC).

For the DSC analysis, the purge gas used was dry nitrogen, the reference material was an empty aluminum pan that was crimped, and the sample purge was 50 mL/minute.

SC analysis of the sample was performed by placing ≤5 mg of sample in an aluminum pan with a crimped pan closure. The starting temperature was typically 20° C. with a heating rate of 10° C./minute, and the ending temperature was 300° C. Unless otherwise indicated, all reported transitions are as stated +/−10 degrees C.

For DSC data herein, each composition of the present invention may be characterized by any one, any two, or any three DSC transitions. The different combinations of the PXRD peaks and the DSC transitions can also be used to characterize the compositions.

C. TGA Analysis

TGA analysis of samples was performed using a High Resolution Thermogravimetric Analyzer 2950 (TA Instruments, New Castle, Del., U.S.A.), which uses Advantage for QW-Series, version 1.0.0.78, Thermal Advantage Release 2.0 (82001 T A Instruments-Water LLC). In addition, the analysis software used was Universal Analysis 2000 for Windows 95/95/2000/NT, version 3.1 E; Build 3.1.0.40 ([8]2001 T A Instruments-Water LLC).

For all of the TGA experiments, the purge gas used was dry nitrogen, the balance purge was 40 mL/minute $N_2$, and the sample purge was 60 mL/minute $N_2$.

TGA of the sample was performed by placing 5 mg to 20 mg of sample in a platinum pan. The starting temperature was typically 20° C. with a heating rate of 10° C./minute, and the ending temperature was 400° C.

D. Single Crystal X-Ray Diffraction

Single crystal x-ray data were collected on a Bruker AXS SMART-APEX CCD diffractometer (M. J. Zawarotko, Department of Chemistry, University of South Florida). Lattice parameters were determined from least squares analysis. Reflection data was integrated using the program SAINT. The structure was solved by direct methods and refined by full matrix least squares using the program SHELXTL (Sheldrick, G. M. SHELXTL, Release 5.03; Siemans Analytical X-ray Instruments Inc.: Madison, Wis.).

Procedure for Determining Dissolution Profiles

Solubility profiles for co-crystals were determined by UV-vis spectroscopy (Perkin Elmer-Lambda 25 UV-vis spectrometer, 400 nm).

Dissolution profiles of co-crystals of the present invention may be compared to the corresponding nutraceutical reference forms to find the increase in the solubility of the co-crystal form when compared to the reference form of the nutraceutical.

Conclusion

The co-crystals of the present invention can be characterized by any one, any two, any three, any four, any five, any six, any seven, any eight, any nine, any ten, or any single integer number of PXRD 2-theta angle peaks listed herein or disclosed in a figure, or by single crystal x-ray diffraction data.

Example 1

Methanol Solvate of Co-Crystal of Quercetin and Caffeine—KP05

34.0 mg (0.101 mmol) of quercetin dehydrate (98% pure, Sigma Aldrich) and 19 mg (0.100 mmol) of caffeine (Sigma Aldrich) were dissolved in approximately 6 mL methanol by heating. Slow evaporation of the solvent yielded golden yellow crystals of quercetin:caffeine (1:1) co-crystal (hereinafter, "KP05"). A digital microscopic image of KP05 is shown in FIG. 1 of the accompanying drawings. The reaction scheme is shown below:

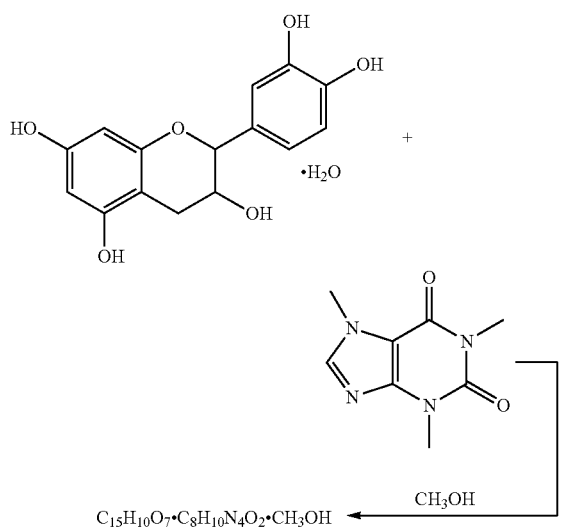

Figure 2:
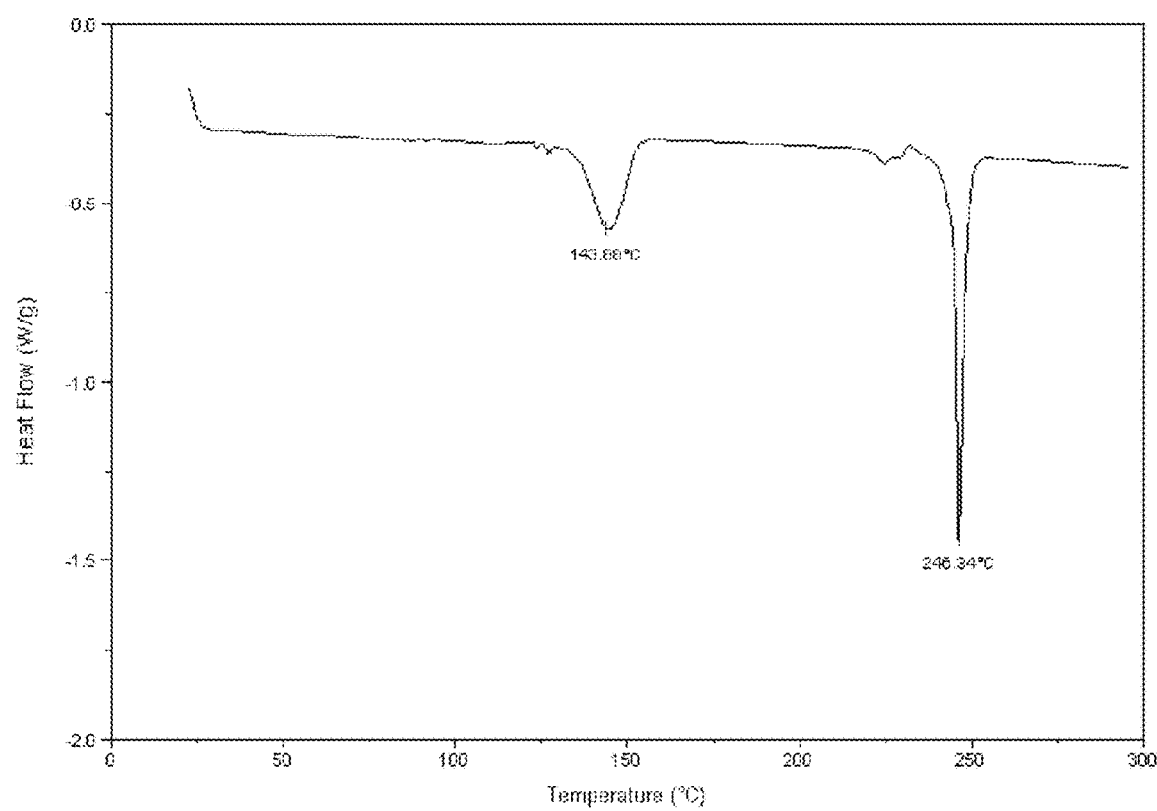
FIG. 2 shows a DSC graph for KP05 as described more fully in Example 1.

KP05 was characterized by DSC analysis, which showed phase changes at about 144° C. and about 246° C. The DSC graph is shown in FIG. 2 of the accompanying drawings.

Figure 3:
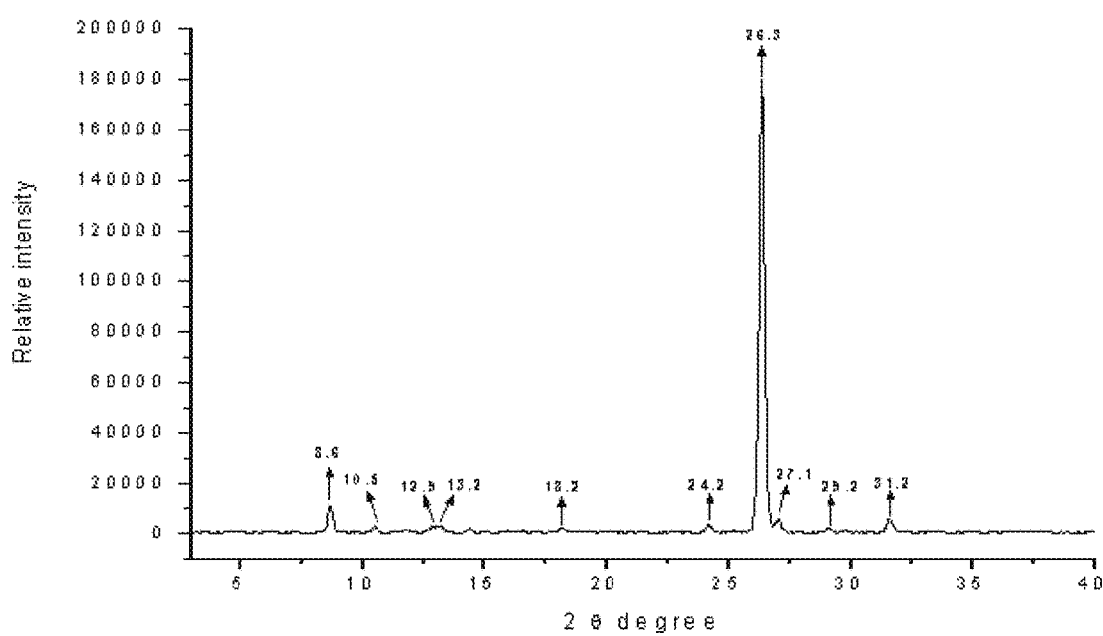
FIG. 3 shows an experimental XRPD pattern of KP05 as described more fully in Example 1, exhibiting major peaks at about the following positions: 8.6, 10.5, 18.2, 24.2, 26.3, 29.2, and 31.2.
Figure 4:
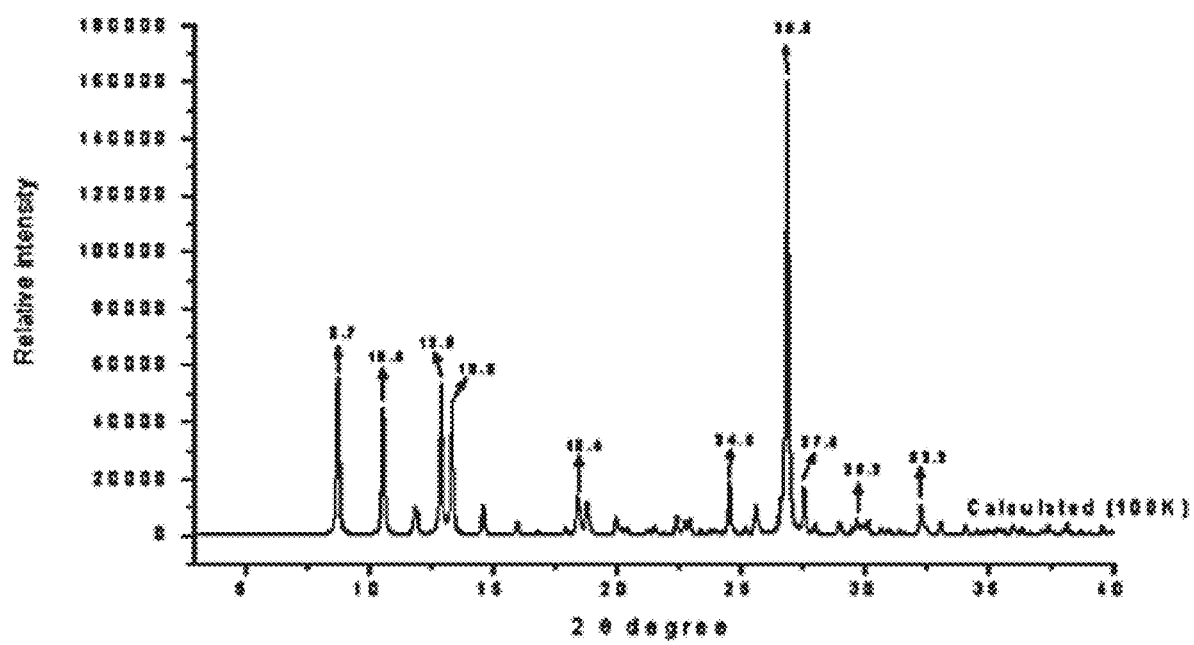
FIG. 4 shows a calculated XRPD pattern for KP05 as described more fully in Example 1.
Figure 5:
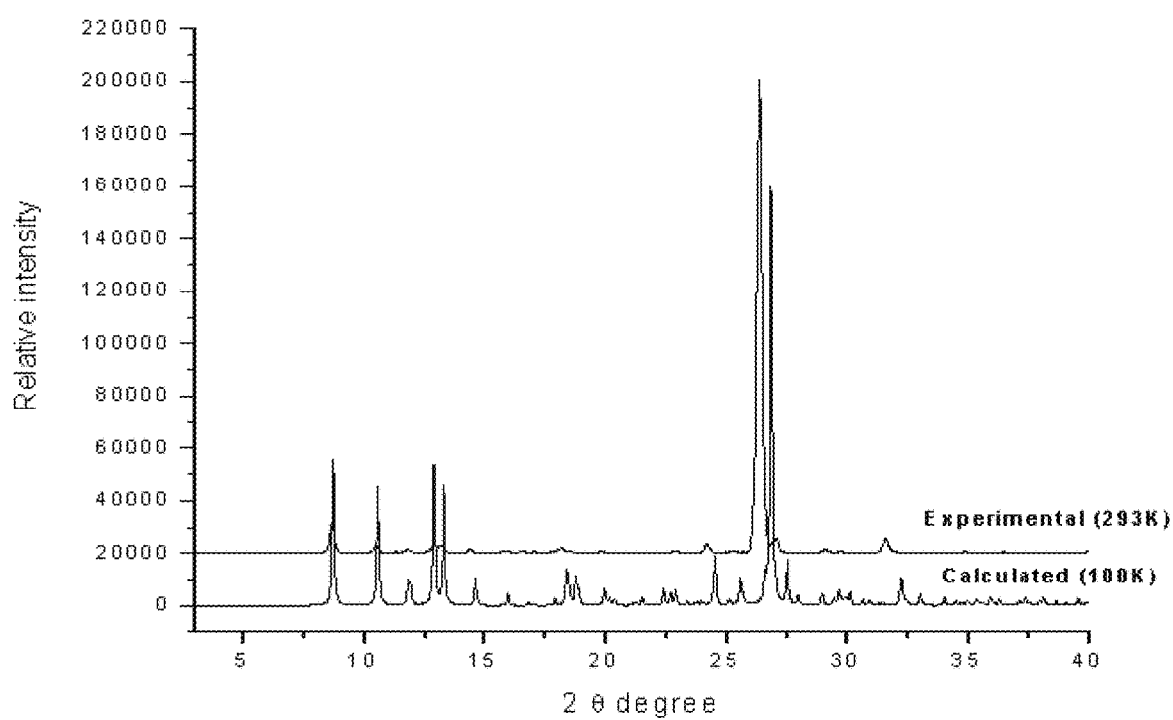
FIG. 5 shows the comparison of the experimental and calculated XRPD graphs for KP05 as described more fully in Example 1.

KP05 can be characterized using XRPD, and exhibited major peaks at about the following positions: 8.6, 10.5, 18.2, 24.2, 26.3, 29.2, and 31.2 degrees. The experimental XRPD graph for KP05 is shown in FIG. 3 of the accompanying drawings. The calculated XRPD graph for KP05 is shown in FIG. 4 of the accompanying drawings, and a comparison of the experimental and calculated XRPD graphs is shown in FIG. 5 of the accompanying drawings.

Single crystal x-ray diffraction analysis was also performed on KP05 to determine the crystal structure and physical properties thereof. The crystallographic details are shown in the following table:

| KP05 Crystallographic Data | |
|---|---|
| Molecular formula | $C_{24}H_{24}N_4O_{10}$ |
| Formula weight | 528.47 |
| Crystal system | Monoclinic |
| Space group | P2(1)/c |
| Unit cell dimensions | a = 10.315(2) Å |
| | b = 14.853(4) Å |
| | c = 15.229(4) Å |
| | α = 90° |
| | β = 100.667(4)° |
| | γ = 90° |
| Volume | 2292.9(9) Å$^3$ |
| Z | 4 |
| Temperature | 100(2) K |
| Density (calculated) | 1.531 mg/m$^3$ |
| (Mo—K) | 0.71073 Å |
| Reflections measured | 7075 |
| Independent reflections | 4517 [R(int) = 0.0303] |
| Final R indices[I > 2sigma(I)] | R1 = 0.0637, wR2 = 0.1611 |
| R indices (all data) | R1 = 0.0890, wR2 = 0.1751 |

Figure 6:
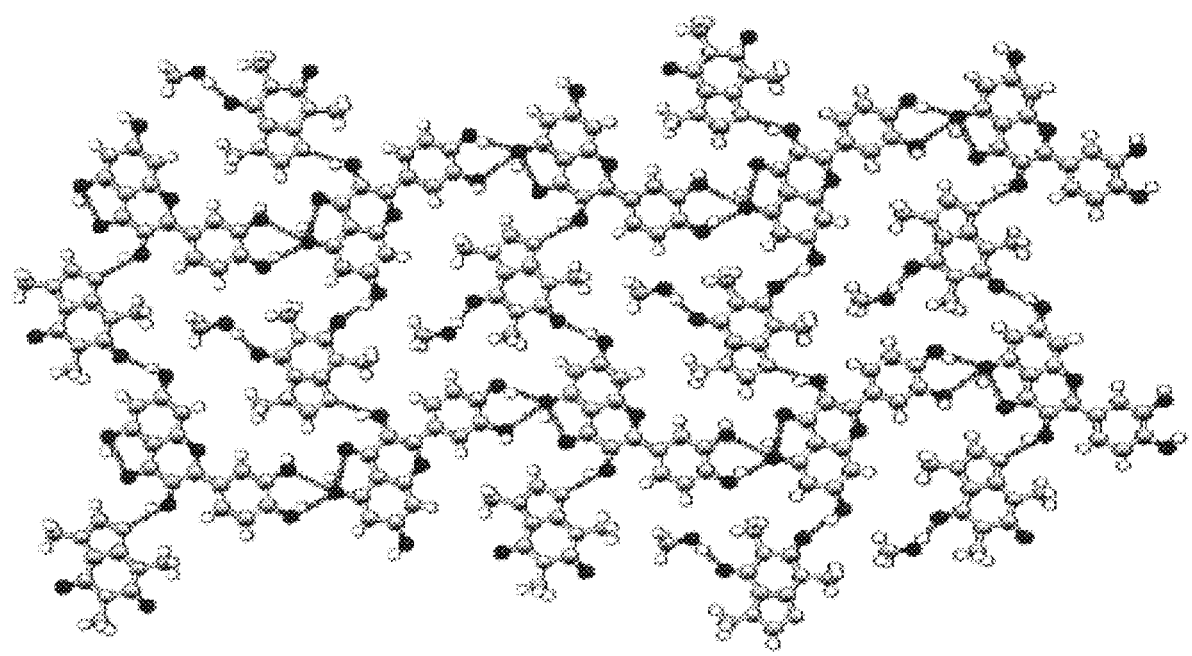
FIG. 6 shows intermolecular interactions in KP05 as described more fully in Example 1.
Figure 7:
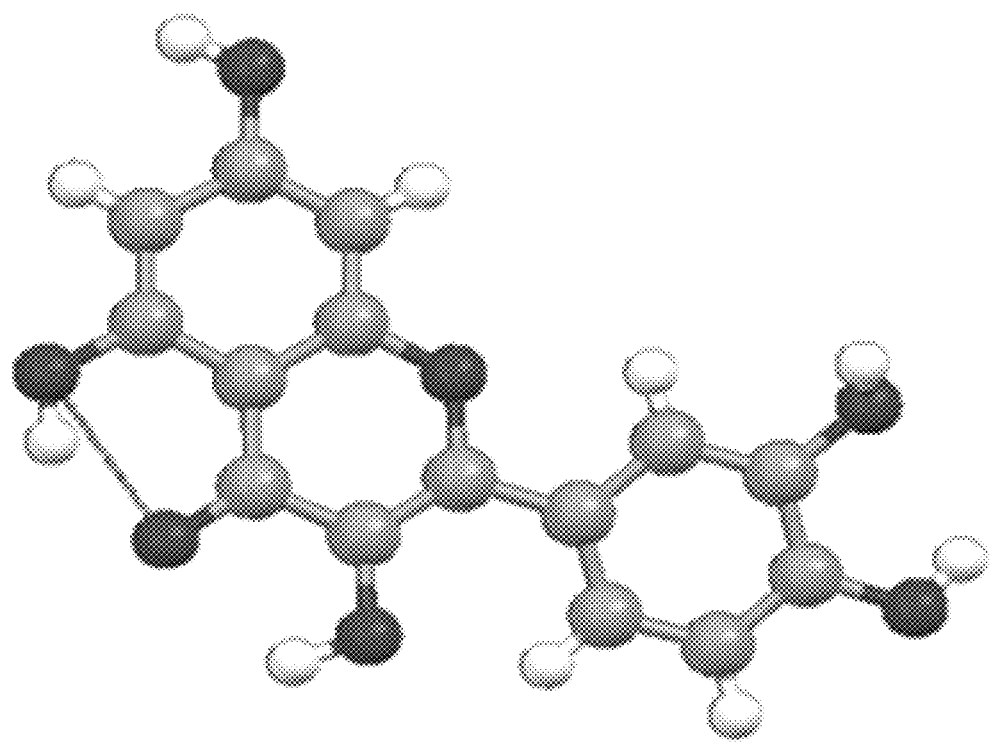
FIG. 7 shows a quercetin molecule as it exists in KP05 as described more fully in Example 1.

The crystal structure indicates that molecules of caffeine form hydrogen bonds with molecules of quercetin and molecules of methanol in a 1:1:1 ratio. The hydrogen bond interactions afford supramolecular sheets. Intermolecular interactions are shown in FIG. 6 of the accompanying drawings. A quercetin molecule as it exists in KP05 is shown in FIG. 7 of the accompanying drawings.

Figure 8:
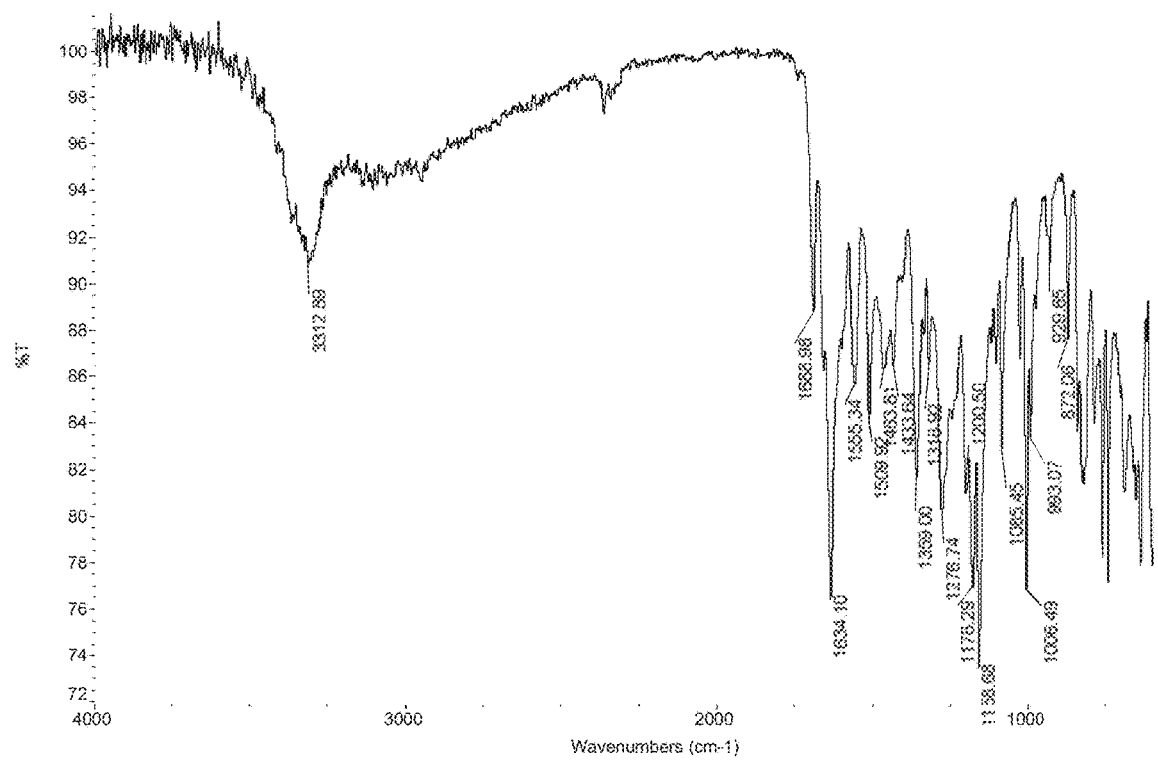
FIG. 8 shows the FT-IR spectra for KP05 as described more fully in Example 1.

KP05 was further characterized by FT-IR. The FT-IR spectra for KP05 is shown in FIG. 8 of the accompanying drawings.

Figure 9:
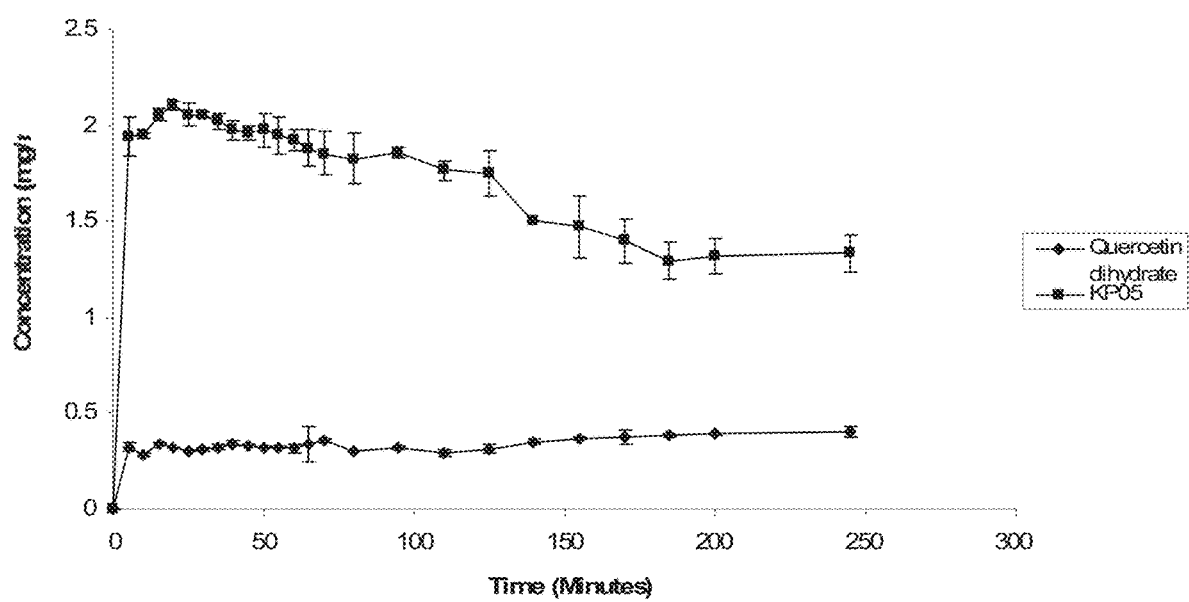
FIG. 9 shows a comparison of dissolution profiles of quercetin dehydrate and KP05, as more fully described in Example 1, in 3:2 methanol/water (V/V %)

The solubility of KP05 in 3:2 methanol/water (V/V %) was determined by UV-vis spectroscopy. The comparison of dissolution profiles of quercetin dehydrate and KP05 in 3:2 methanol/water (V/V %) is shown in FIG. 9 of the accompanying drawings.

Example 2

Co-Crystal of Quercetin and Iso-Nicotinamide—KP10

Figure 10:
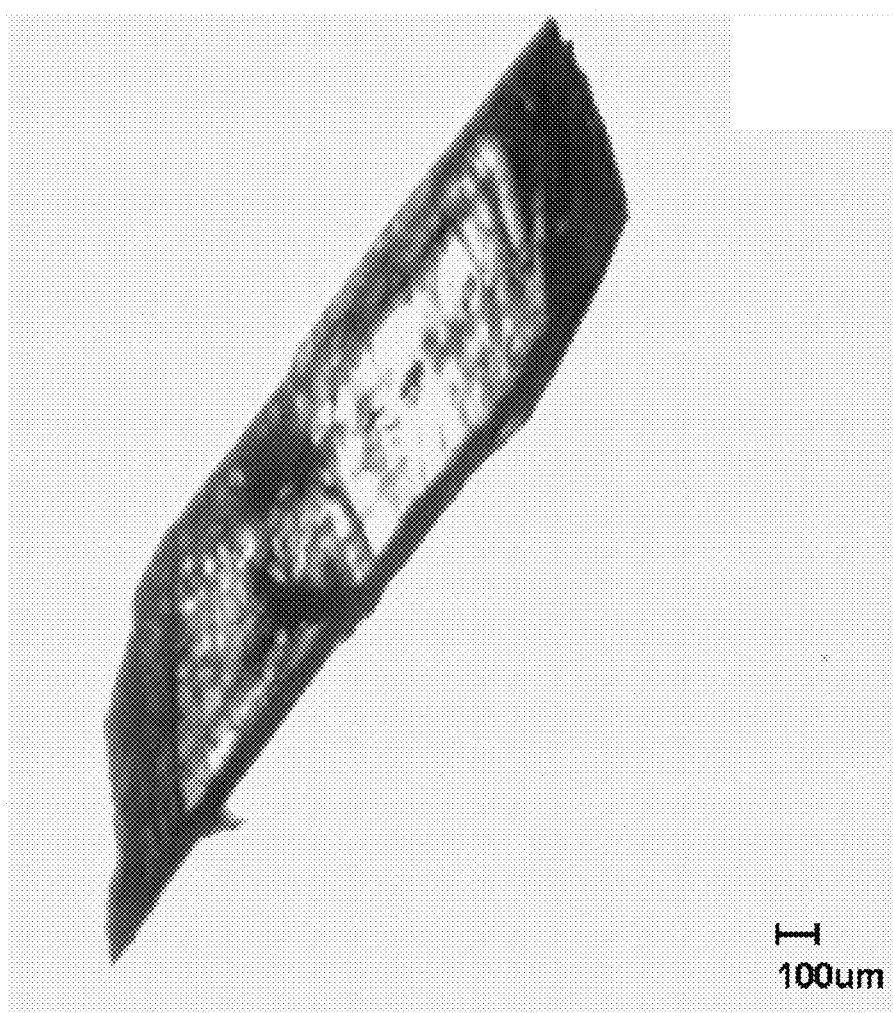
FIG. 10 shows a digital microscopic image of KP10 as described more fully in Example 2.

34.0 mg (0.101 mmole) of quercetin dehydrate (98% pure, Sigma Adrich) and 12.3 mg (0.100 mmol) iso-nicotinamide (Sigma Aldrich) were dissolved in approximately 6 mL of methanol by heating. The resulting solution was cooled in a refrigerator and allowed to stand for two days. Slow evaporation yielded golden yellow crystals of 1:1 quercetin:iso-nicotinamide co-crystal (hereinafter "KP0"). A digital microscopic image of KP10 is shown in FIG. 10 of the accompanying drawings. KP10 can also be prepared by slurrying in methanol overnight. The reaction scheme is shown below:

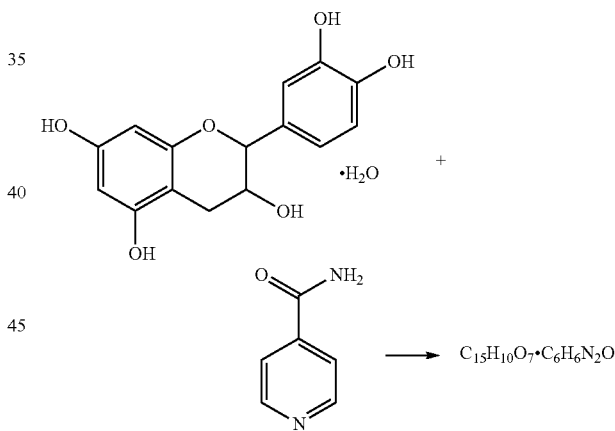

Figure 11:
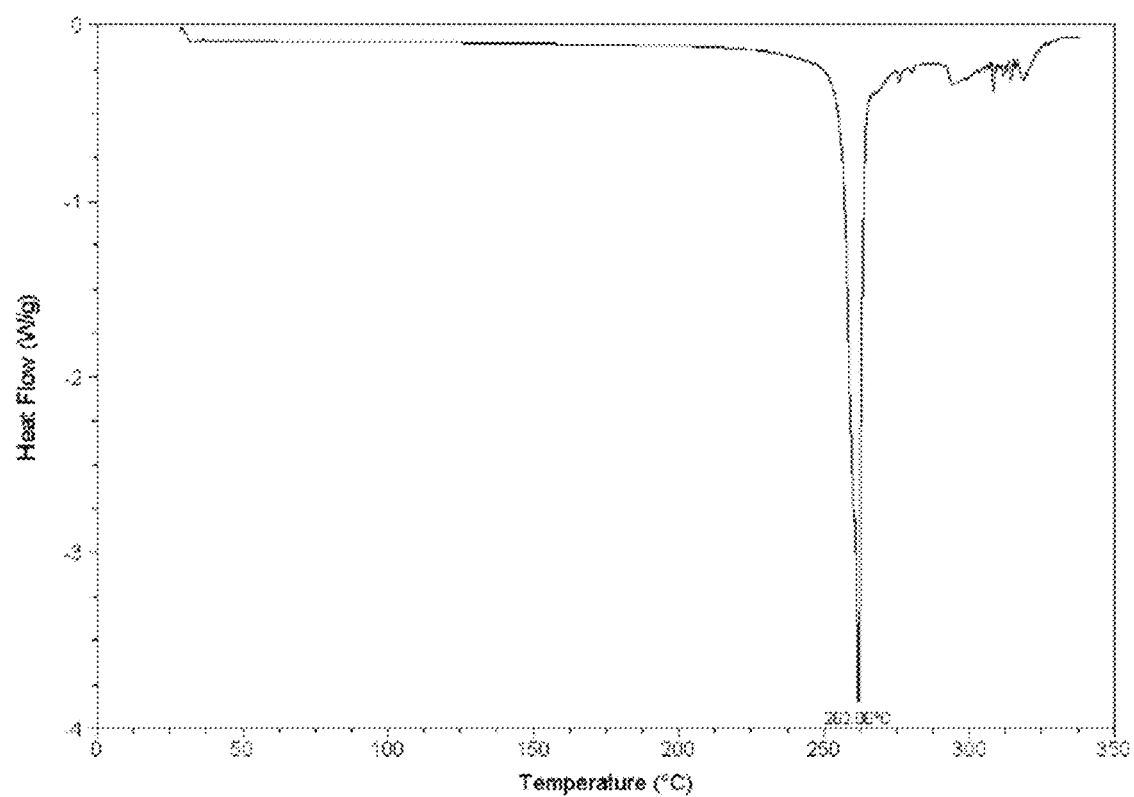
FIG. 11 shows a DSC graph for KP10 as described more fully in Example 2.

DSC analysis was performed on KP10 and showed a phase change at about 262° C. The DSC graph is shown in FIG. 11 of the accompanying drawings.

Figure 12:
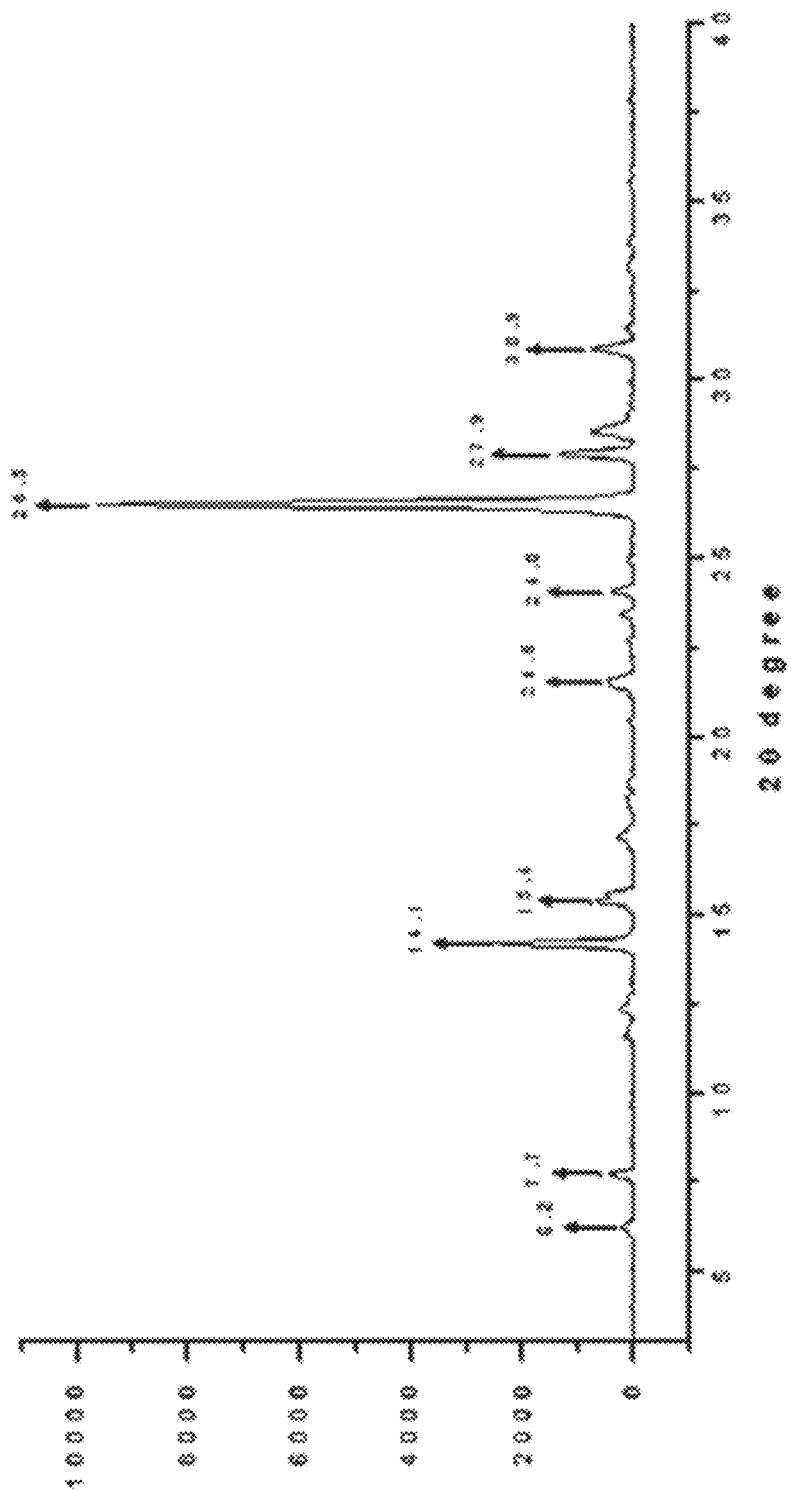
FIG. 12 shows an experimental XRPD pattern of KP10, as described more fully in Example 2, exhibiting major peaks at about the following positions: 6.2, 7.7, 14.1, 15.4, 21.5, 24.0, 26.5, 27.9, and 30.9.
Figure 13:
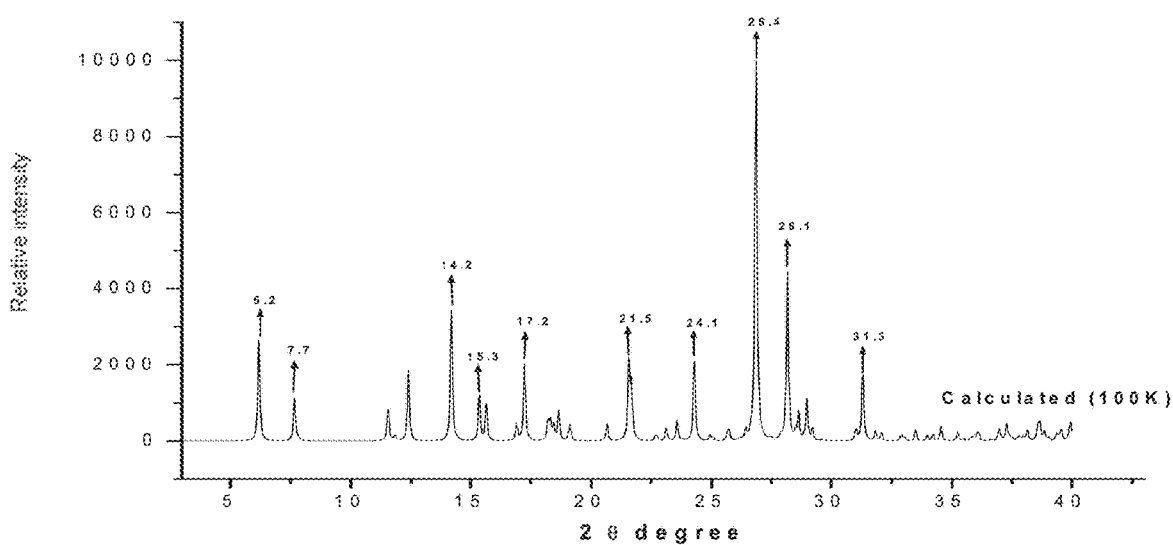
FIG. 13 shows a calculated XRPD pattern for KP10 as described more fully in Example 2.
Figure 14:
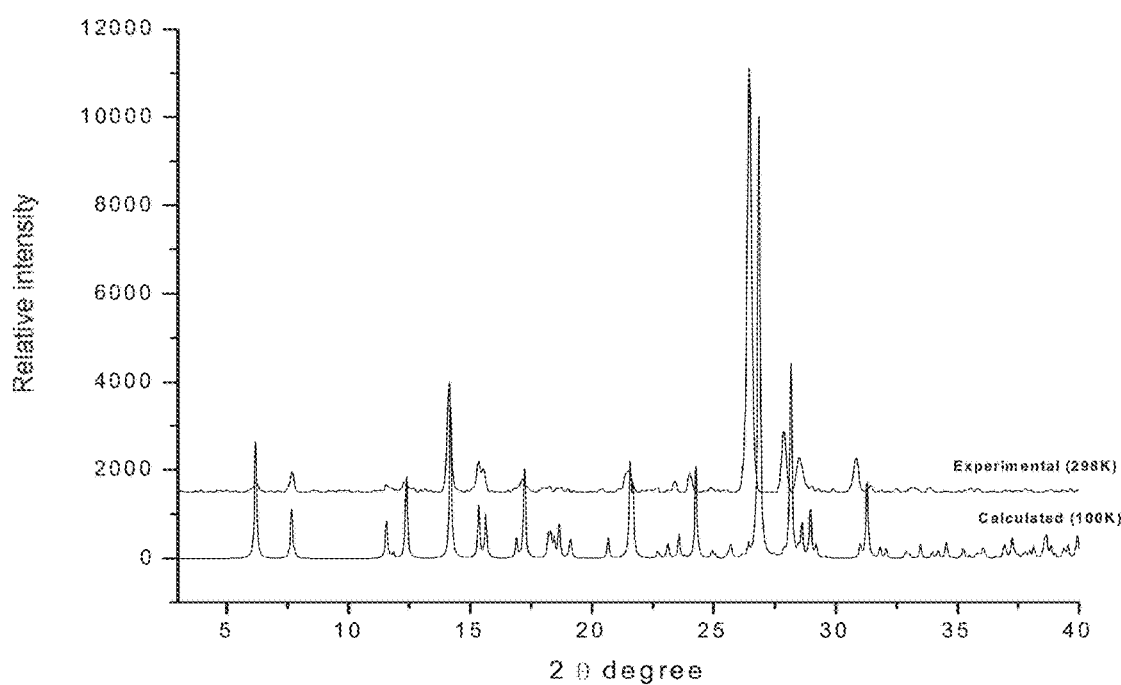
FIG. 14 shows a comparison of the experimental and calculated XRPD data for KP10 as described more fully in Example 2.

KP10 can be characterized using XRPD, and exhibited major peaks at about the following positions: 6.2, 7.7, 14.1, 15.4, 21.5, 24.0, 26.5, 27.9, and 30.9 degrees. The experimental XRPD graph for KP0 is shown in FIG. 12 of the accompanying drawings. The calculated XRPD graph for KP10 is shown in FIG. 13 of the accompanying drawings. A comparison of the experimental and the calculated XRPD data for KP10 is shown in FIG. 14 of the accompanying drawings.

Single crystal x-ray diffraction analysis was also performed on KP100 to determine the crystal structure and physical properties thereof. The crystallographic details are shown in the following table:

| KP10 Crystallographic Data | |
| --- | --- |
| Molecular formula | $C_{10}H_{16}N_2O_8$ |
| Formula weight | 424.36 |
| Crystal system | Triclinic |
| Space group | P-1 |
| Unit cell dimensions | a = 4.978(10) Å |
| | b = 12.636(3) Å |
| | c = 15.571(3) Å |
| | $\alpha$ = 110.53(3)° |
| | $\beta$ = 97.63(3)° |
| | $\gamma$ = 99.39(3)° |
| Volume | 885.7(3) Å$^3$ |
| Z | 2 |
| Temperature | 100(2) K |
| Density (calculated) | 1.591 mg/m$^3$ |
| (Mo—K) | 0.71073 Å |
| Reflections measured | 4941 |
| Independent reflections | 3745 [R(int) = 0.0399] |
| Final R indices[I > 2sigma(I)] | R1 = 0.0624, wR2 = 0.1395 |
| R indices (all data) | R1 = 0.1006, wR2 = 0.1643 |

Figure 15:
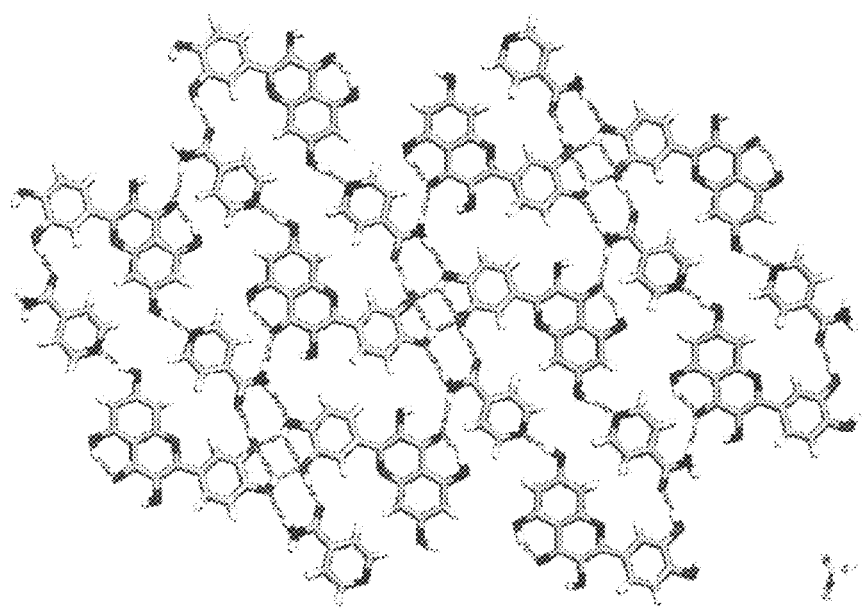
FIG. 15 shows the intermolecular interactions in KP10, as described more fully in Example 2.
Figure 16:
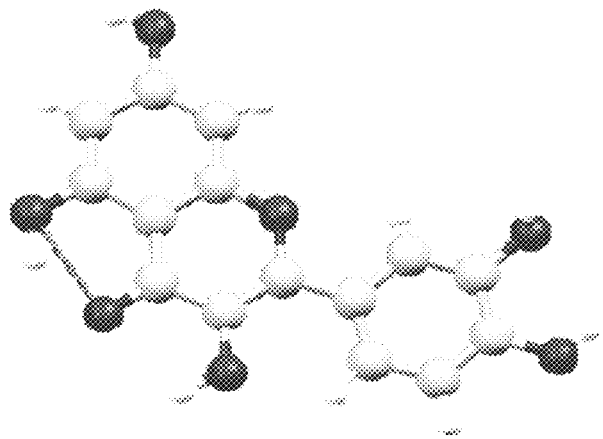
FIG. 16 shows a quercetin molecule as it exists in KP10, as described more fully in Example 2.

The crystal structure indicates that molecules of quercetin form hydrogen bonds with molecules of iso-nicotinamide and that KP10 contains a 1:1 ratio of quercetin and iso-nicotinamide. The quercetin molecules form hydrogen bonded dimmers whose peripheral hydrogen bonding moieties form hydrogen bonds with the N—H moieties of iso-nicotinamide molecules. The overall hydrogen bonding results in sheets. The hydrogen bonding in KP10 is shown in FIG. 15 of the accompanying drawings. A quercetin molecule, as it exists in KP10 is shown in FIG. 16 of the accompanying drawings.

Figure 17:
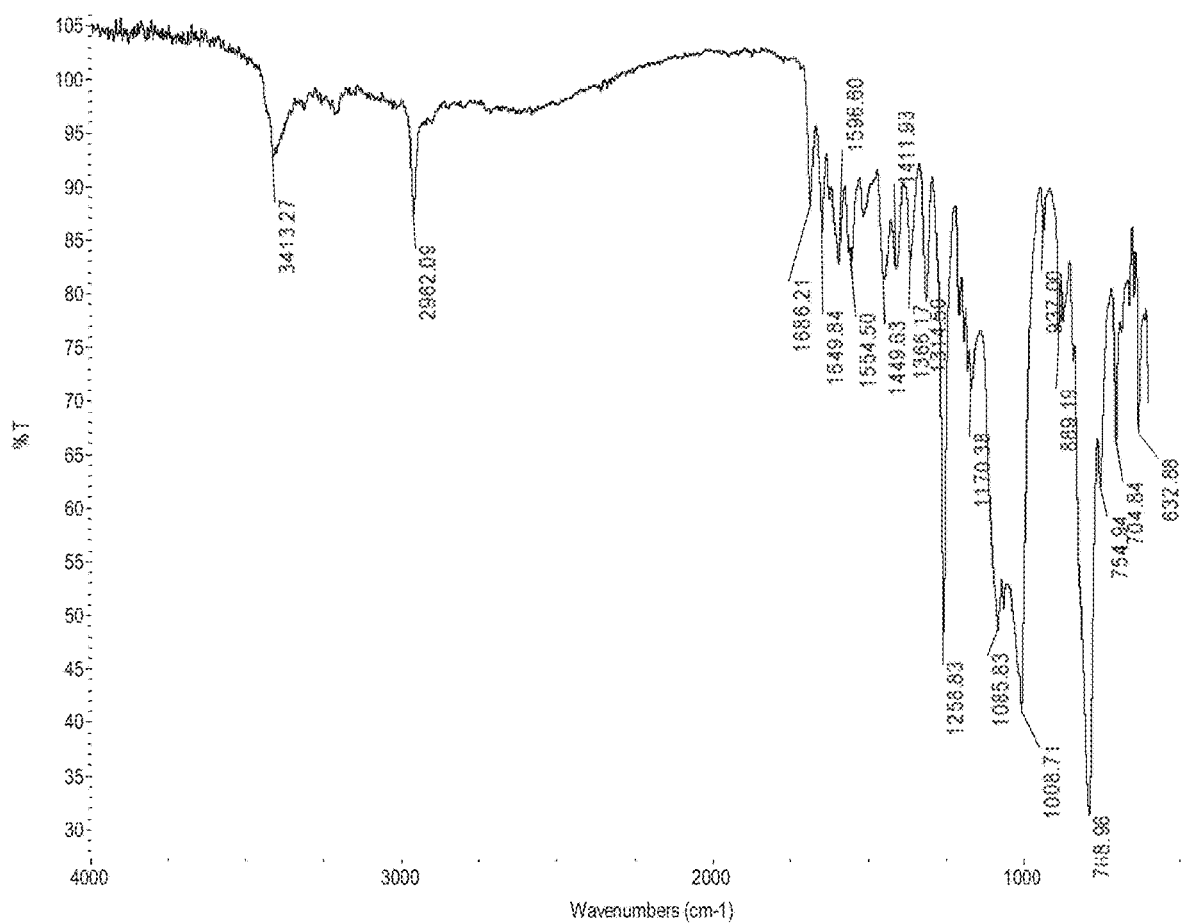
FIG. 17 shows the FT-IR spectra for KP10 as described more fully in Example 2.

KP10 was further characterized by FT-IR. The FT-IR spectra for KP10 is shown in FIG. 17 of the accompanying drawings.

Figure 18:
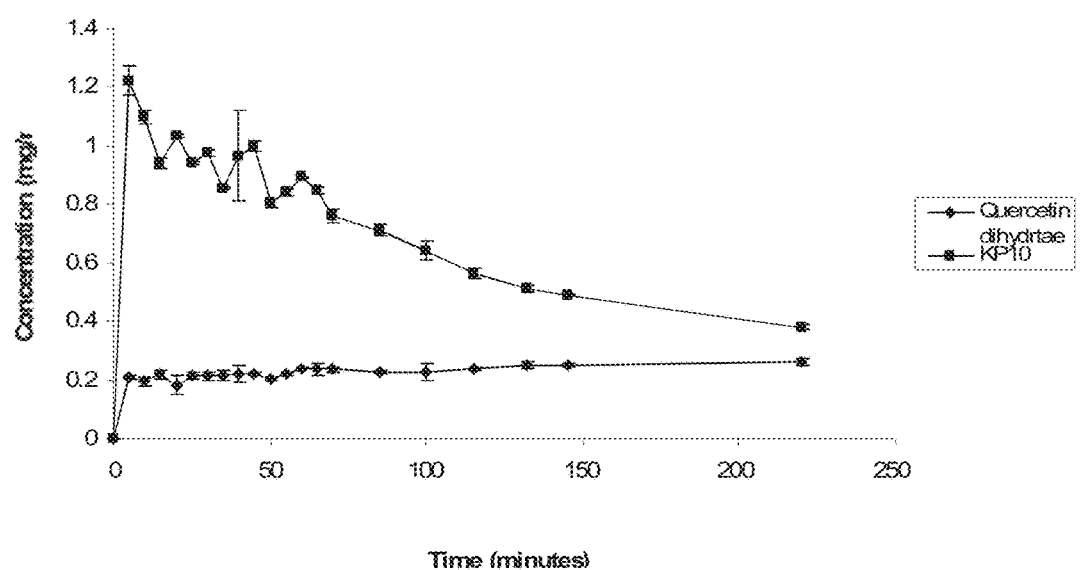
FIG. 18 shows a comparison of dissolution profiles of quercetin dehydrate and KP10, as more fully described in Example 2, in 1:1 ethanol/water (V/V %)

The solubility of KP10 in 1:1 ethanol/water (V/V %) was determined by UV-vis spectroscopy, with a wavelength of 360 nm. The dissolution study indicates that there is an approximate 6-fold increase in the solubility of quercetin in KP10 when compared to quercetin dehydrate. A comparison of dissolution profiles of quercetin dehydrate and KP10 is shown in FIG. 18 of the accompanying drawings.

Example 3

Co-Crystal of Hesperetin and Iso-Nicotinamide—KP15

30.2 mg (0.0100 mmol) hesperetin (95% pure, Sigma Aldrich) and 12.2 mg (0.0100 mmol) iso-nicotinamide (99% pure, Sigma Aldrich) were dissolved in approximately 8 mL of methanol by heating. The resulting solution was cooled in a refrigerator and allowed to stand for one week. This slow evaporation yielded colorless crystals of 1:1 hesperetin:iso-nicotinamide co-crystal (hereinafter "KP15"). DSC analysis showed a phase change at about 180° C.

Figure 19:
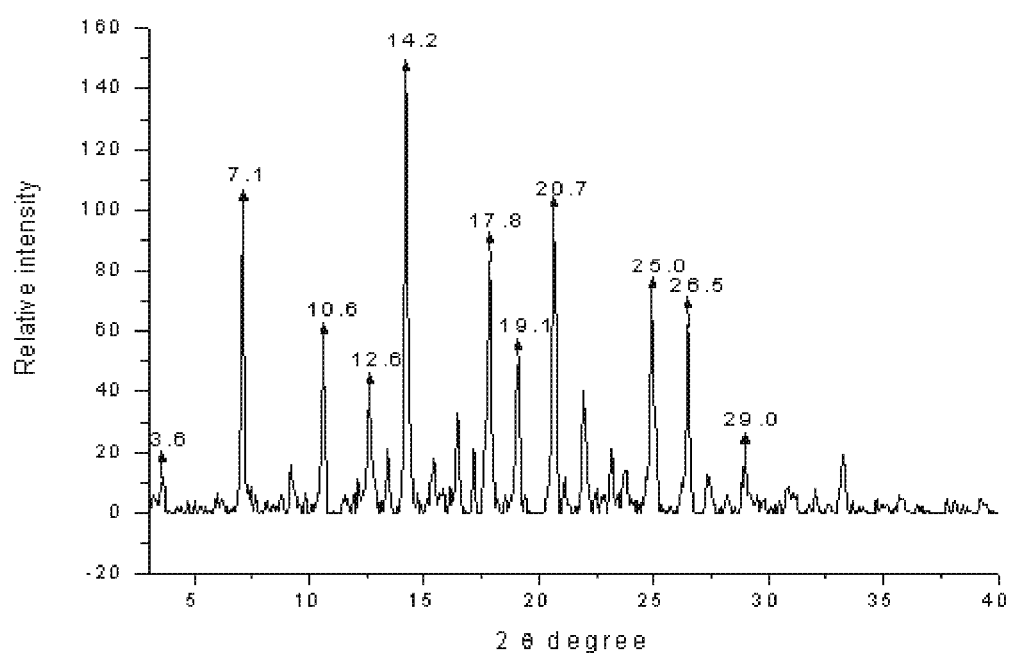
FIG. 19 shows an XRPD pattern of KP15, as described more fully in Example 3, exhibiting major peaks at about the following positions: 3.6, 7.1, 10.6, 12.6, 14.2, 17.8, 19.1, 20.7, 25.0, 26.5, and 29.0.

KP15 can be characterized using XRPD, and exhibited major peaks at about the following positions: 3.6, 7.1, 10.6, 12.6, 14.2, 17.8, 19.1, 20.7, 25.0, 26.5, and 29.0 degrees. The XRPD graph for KP15 is shown in FIG. 19 of the accompanying drawings.

Figure 20:
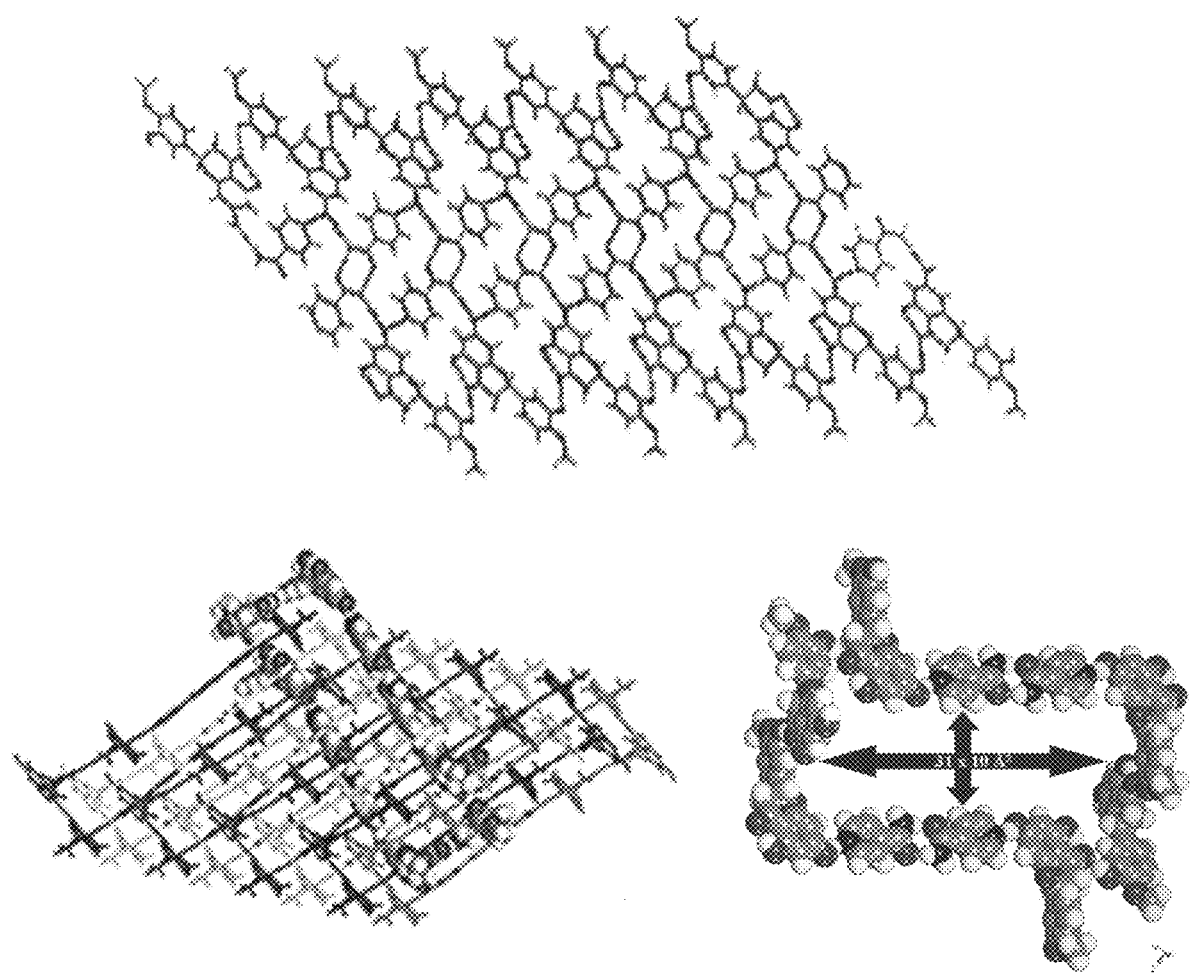
FIG. 20 shows the intermolecular interactions in KP15, as described more fully in Example 3, including the eight-fold interpenetrated network and the 31 Å×10 Å cavity formed in KP15.

Hydrogen bonding occurs between two of the phenolic —OH moieties of hesperetin molecules and the following: other hesperetin molecules and the pyridyl moieties of iso-nicotinamide dimmers (OH . . . O-2.720 (2) Å, OH . . . N=2.623 (1) Å). The three-dimensional networks thereby generated contain 31.0 Å×10.0 Å cavities which facilitate 8-fold interpenetration. The intermolecular interactions in KP15 are shown in FIG. 20 of the accompanying drawings. In addition, one of the three phenolic —OH moieties engages in an intramolecular hydrogen bond with the carbonyl moiety.

Single crystal x-ray diffraction analysis was also performed on KP15 to determine the crystal structure and physical properties thereof. The crystallographic details are shown in the following table:

| KP15 Crystallographic Data | |
| --- | --- |
| Molecular formula | $C_{22}H_{20}N_2O_7$ |
| Formula weight | 424.40 |
| Crystal system | Monoclinic |
| Space group | P2$_1$/c |
| Unit cell dimensions | a = 25.653(10) Å |
| | b = 5.129(2) Å |
| | c = 14.880(6) Å |
| | $\alpha$ = 90° |
| | $\beta$ = 103.384(7)° |
| | $\gamma$ = 90° |
| Volume | 1904.7(13) Å$^3$ |
| Z | 4 |
| Temperature | 100(2) K |
| Density (calculated) | 1.480 mg/m$^3$ |
| (Mo—K) | 0.71073 Å |
| Reflections measured | 10754 |
| Independent reflections | 4364 [R(int) = 0.0382] |
| Final R indices[I > 2sigma(I)] | R1 = 0.0584, wR2 = 0.1443 |
| R indices (all data) | R1 = 0.0835, wR2 = 0.1585 |

Figure 21:
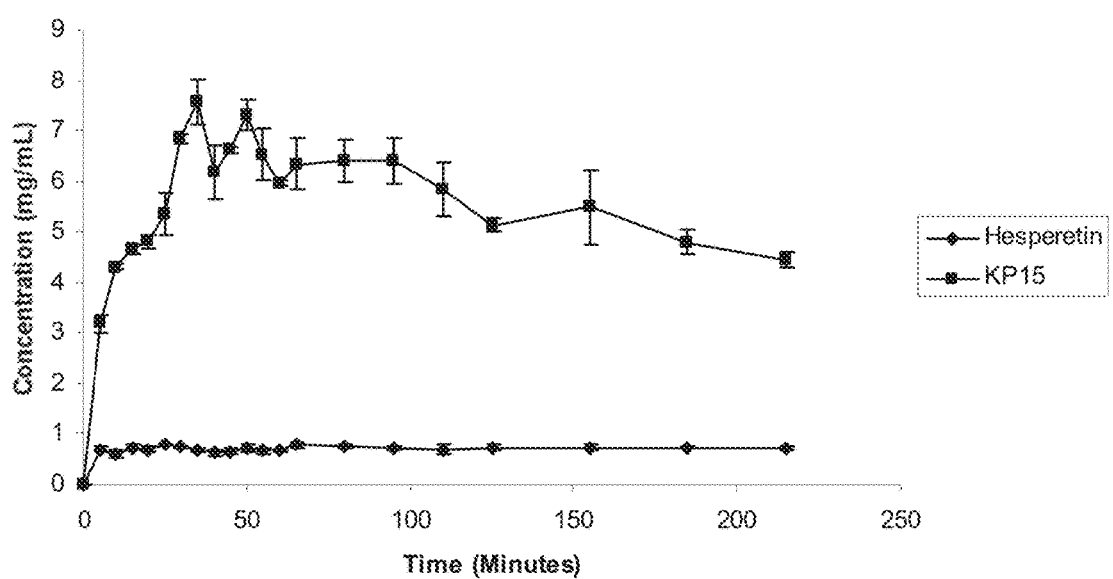
FIG. 21 shows a comparison of dissolution profiles of hesperetin and KP15, as described more fully in Example 3, in 1:1 ethanol/water (V/V %)

The solubility of KP15 in 1:1 ethanol/water (V/V %) was determined by UV-vis spectroscopy, with a wavelength of 300 nm. The dissolution study indicates that there is an approximately 12-fold increase in the solubility of hesperetin in KP15 when compared to pure hesperetin. A comparison of dissolution profiles of hesperetin and KP155 is shown in FIG. 21 of the accompanying drawings.

Example 4

Co-Crystal of Hesperetin and Nicotinic Acid—KP22

Hesperetin (95% pure, Sigma Aldrich) 30.2 mg (0.0100 mmol) and nicotinic acid (99% pure, Sigma Aldrich) 12.3 mg (0.0100 mmol) were dissolved in 8 mL of methanol by heating. The resulting solution was cooled in a refrigerator and allowed to stand for three days. This slow evaporation yielded colorless crystals of 1:1 hesperetin:nicotinic acid co-crystal (hereinafter "KP22"). DSC analysis showed a phase change at about 206° C.

Figure 22:
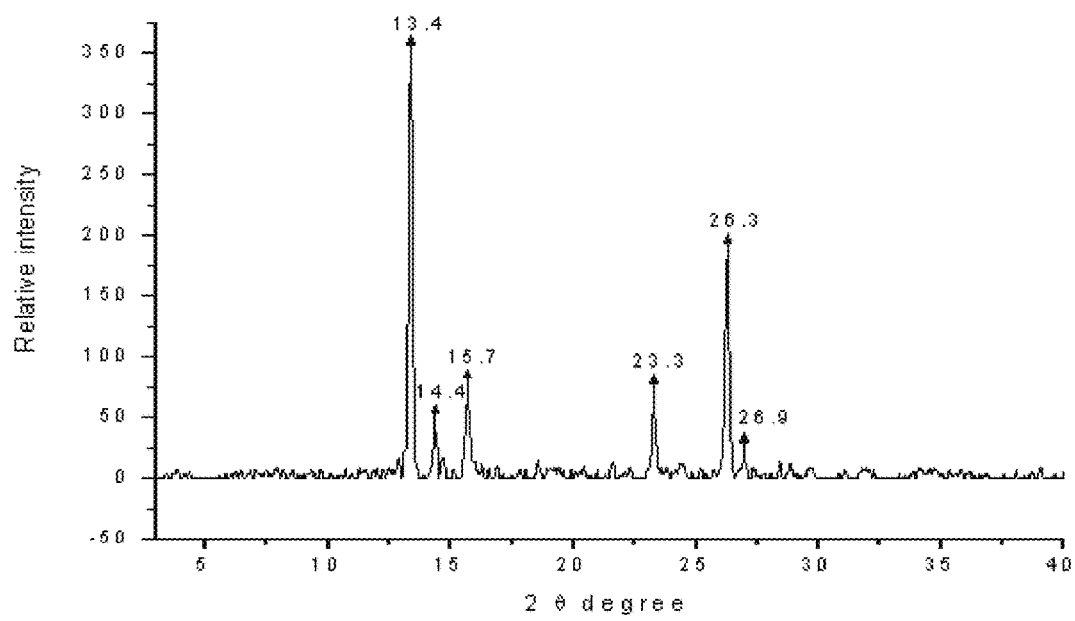
FIG. 22 shows an XRPD pattern of KP22, as described more fully in Example 4, exhibiting major peaks at about the following positions: 13.4, 14.4, 15.7, 23.3, 26.3, and 26.9.

KP22 can be characterized using XRPD, and exhibited major peaks at about the following positions: 13.4, 14.4, 15.7, 23.3, 26.3, and 26.9 degrees. The XRPD graph for KP22 is shown in FIG. 22 of the accompanying drawings.

Single crystal x-ray diffraction analysis was also performed on KP15 to determine the crystal structure and physical properties thereof. The crystallographic details are shown in the following table:

| KP22 Crystallographic Data | |
| --- | --- |
| Molecular formula | $C_{22}H_{19}NO_8$ |
| Formula weight | 425.38 |
| Crystal system | Triclinic |
| Space group | P-1 |
| Unit cell dimensions | a = 6.7055(15) Å |
| | b = 11.494(3) Å |
| | c = 12.402(3) Å |
| | $\alpha$ = 89.635(4)° |
| | $\beta$ = 85.483(4)° |
| | $\gamma$ = 86.623(4)° |

-continued

| KP22 Crystallographic Data | |
| --- | --- |
| Volume | 951.3(4) Å$^3$ |
| Z | 2 |
| Temperature | 100(2) K |
| Density (calculated) | 1.485 mg/m$^3$ |
| (Mo—K) | 0.71073 Å |
| Reflections measured | 7253 |
| Independent reflections | 5851 [R(int) = 0.0270] |
| Final R indices[I > 2sigma(I)] | R1 = 0.0688, wR2 = 0.1692 |
| R indices (all data) | R1 = 0.0911, wR2 = 0.1845 |

Figure 23:
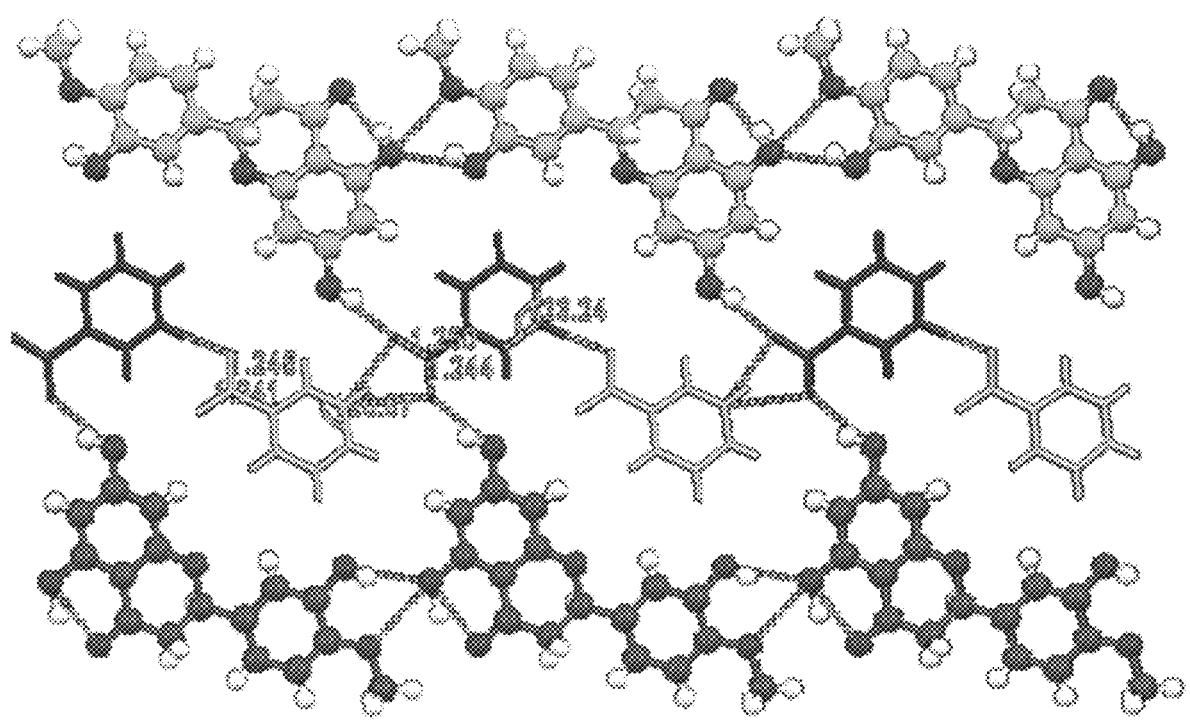
FIG. 23 shows the intermolecular interactions in KP22, as described more fully in Example 4.

The crystal structure reveals that nicotinic acid exists and a zwitterion in KP22. There are two types of nicotinic acid zwitterions that hydrogen bond with each other in a head-to-tail fashion and thereby form chains that are sandwiched between the chains of hesperetin molecules. Both the enantiomers of hesperetin are present in the crystals, however the crystal is polar as the head-to-tail chains of nicotinic acid zwitterions are parallel throughout the crystal structure. The three chains are linked by lateral hydrogen bonds and therefore form a network that could be described as a supramolecular tape. The molecular structure of hesperetin as it exists in KP22 reveals that one of the three phenolic —OH moieties engages in an intramolecular hydrogen bond with the carbonyl moiety. The intermolecular interactions in KP22 are shown in FIG. 23 of the accompanying drawings.

Figure 24:
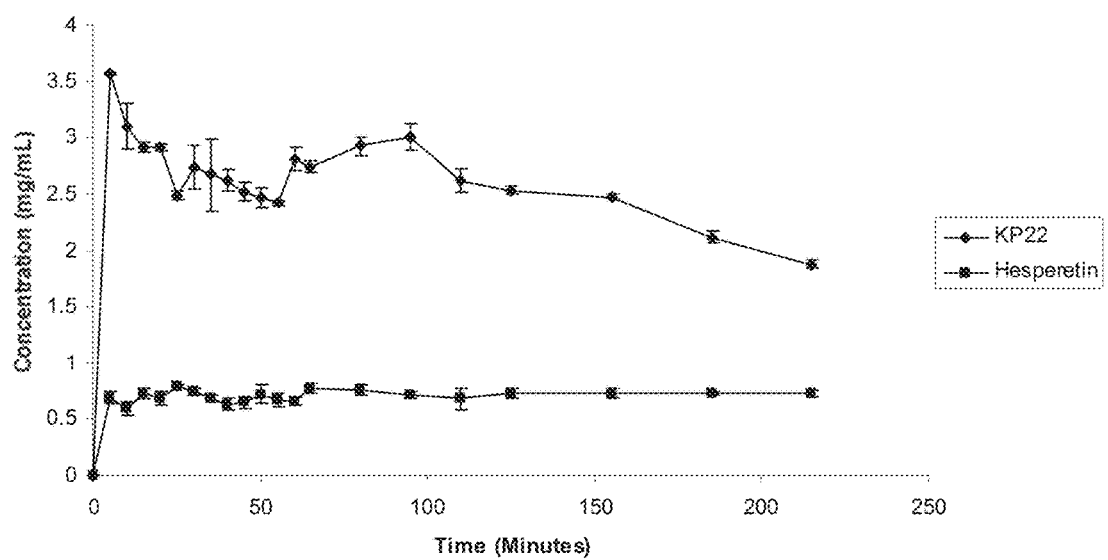
FIG. 24 shows a comparison of dissolution profiles of hesperetin and KP22, as described more fully in Example 4, in 1:1 ethanol/water (V/V %)

The solubility of KP22 in 1:1 ethanol/water (V/V %) was determined by UV-vis spectroscopy, with a wavelength of 300 nm. The dissolution study indicates that there is an approximately 5-fold increase in the solubility of hesperetin in KP22 when compared to pure hesperetin. A comparison of dissolution profiles of hesperetin and KP22 is shown in FIG. 24 of the accompanying drawings.

Example 5

Co-Crystal of Sarcosine and L-Ascorbic Acid—LM560

Sarcosine (99% pure, Sigma Aldrich), 53.4 mg (0.599 mmol) and L-ascorbic acid (99% pure, Sigma Aldrich), 106 mg (0.602 mmol) were dissolved in 6 mL of methanol and heated until a clear solution was obtained. The solution was allowed to evaporate at room temperature and colorless crystals were harvested after four days. This slow evaporation yielded 1:1 co-crystals of sarcosine and L-ascorbic acid (hereinafter, "LM560"). The reaction scheme is illustrated below:

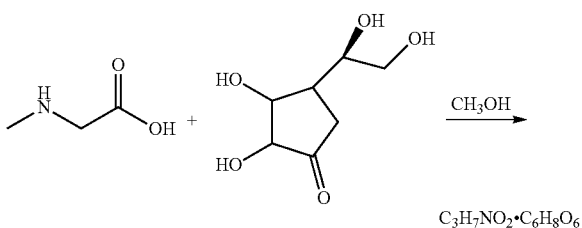

Figure 25:
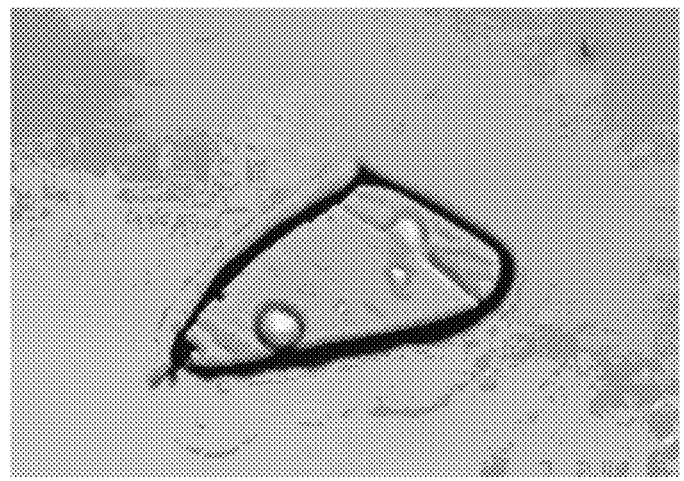
FIG. 25 is a digital microscopic image of LM560 as described more fully in Example 5.
Figure 26:
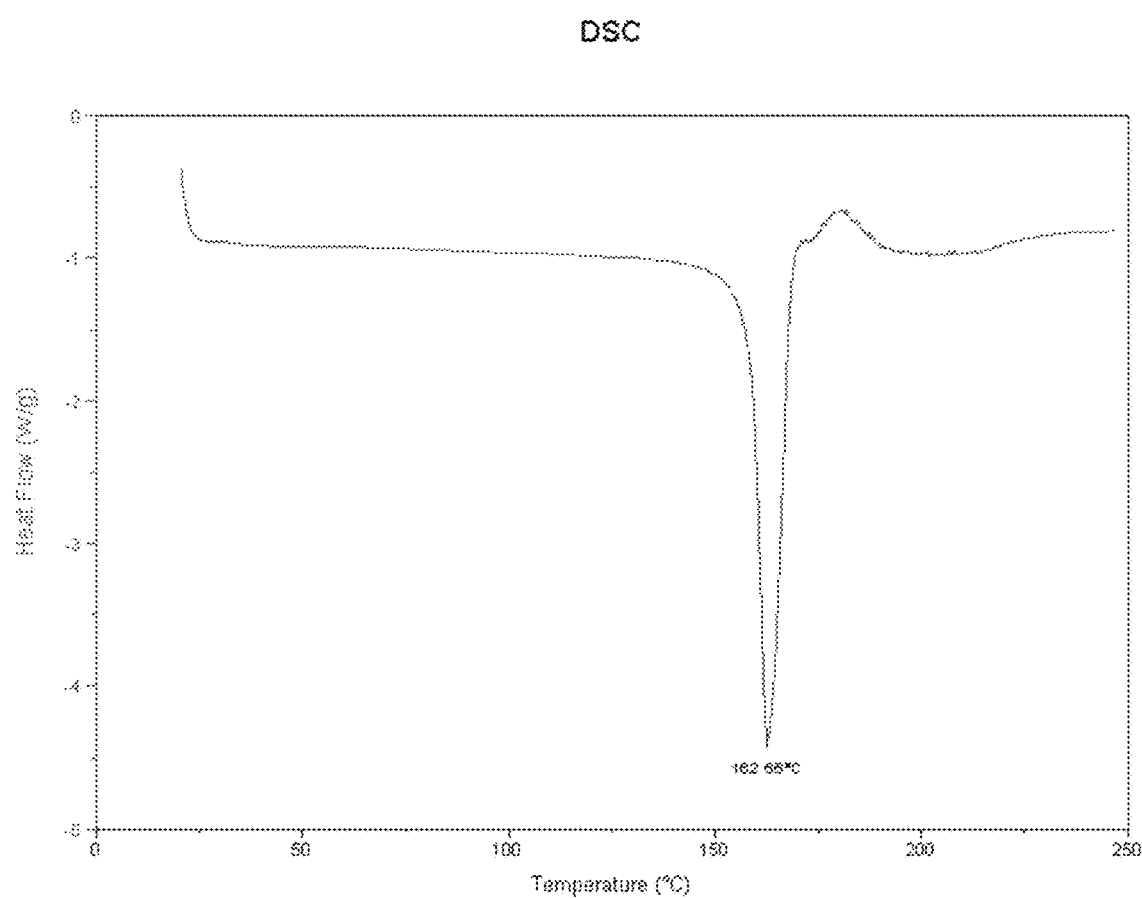
FIG. 26 shows a DSC graph for LM560 as described more fully in Example 5.

LM560 was also produced by solvent drop grinding with the following solvents: DMF, water, formic acid, acetic acid, and methanol, as well as by slurrying with methanol. FIG. 25 of the accompanying drawings is a digital microscopic image of LM560. DSC analysis showed a phase change at about 163° C. FIG. 26 of the accompanying drawings shows the DSC graph.

Figure 27:
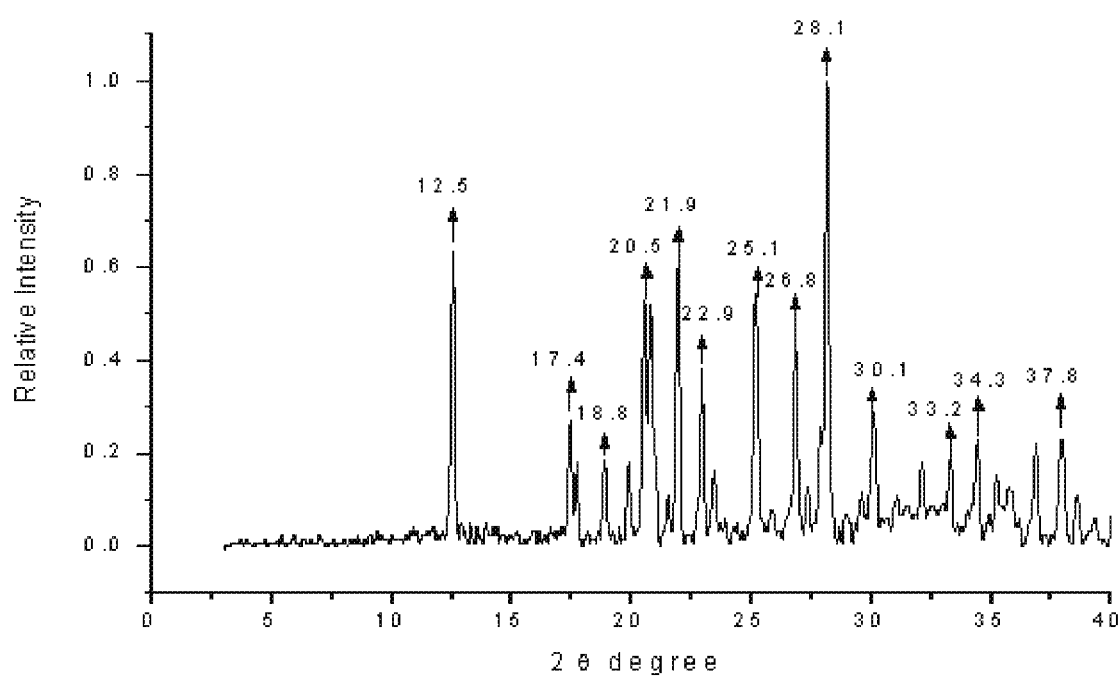
FIG. 27 shows an experimental XRPD pattern of LM560, as described more fully in Example 5, exhibiting major peaks at about the following positions: 12.5, 17.4, 18.8, 20.5, 21.9, 22.9, 25.1, 26.8, 28.1, and 30.1.
Figure 28:
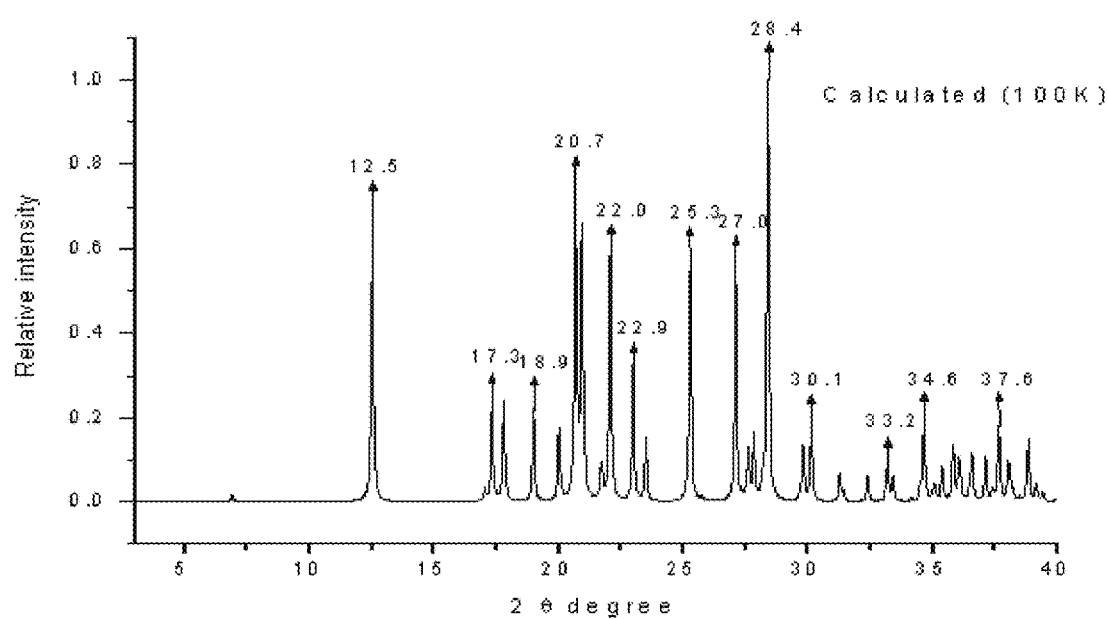
FIG. 28 shows a calculated XRPD pattern for LM560, as described more fully in Example 5.
Figure 29:
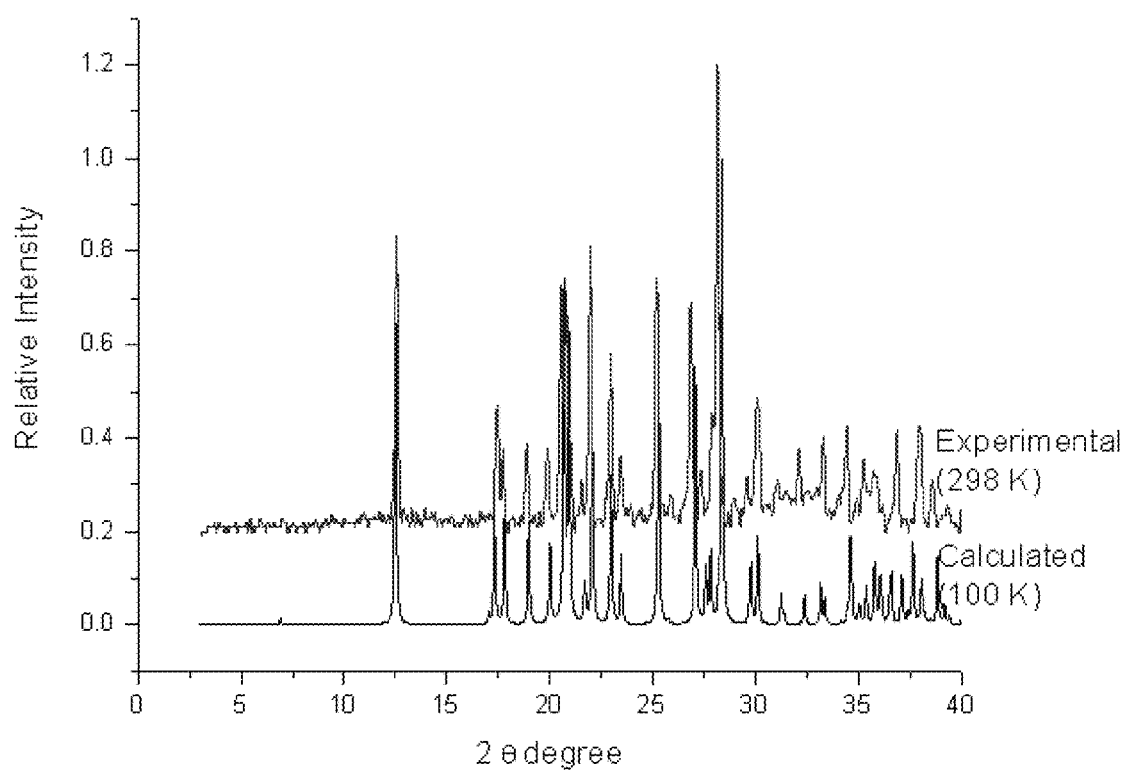
FIG. 29 shows a comparison of the experimental and calculated XRPD graphs for LM560, as described more fully in Example 5.

LM560 can be characterized using XRPD, and exhibited major peaks at about the following positions: 12.5, 17.4, 18.8, 20.5, 21.9, 22.9, 25.1, 26.8, 28.1, and 30.1 degrees. The experimental XRPD graph for LM560 is shown in FIG. 27 of the accompanying drawings. FIG. 28 of the accompanying drawings shows the calculated XRPD values for LM560. FIG. 29 of the accompanying drawings shows a comparison between the experimental and calculated values for LM560.

Single crystal x-ray diffraction analysis was also performed on LM560 to determine the crystal structure and physical properties thereof. The crystallographic details are shown in the following table:

| LM560 Crystallographic Data | |
| --- | --- |
| Empirical formula | C$_9$H$_{15}$NO$_8$ |
| Formula weight | 265.22 |
| Temperature | 100(2) K |
| Wavelength | 0.71073 Å |
| Crystal system | Monoclinic |
| Space group | P2$_1$ |
| Unit cell dimensions | a = 5.223(17) Å |
| | b = 8.486(3) Å |
| | c = 12.871(4) Å |
| | α = 90° |
| | β = 95.22(6)° |
| | γ = 90° |
| Volume | 568.1(3) Å$^3$ |
| Z | 2 |
| Density (calculated) | 1.551 mg/m$^3$ |
| Reflections collected | 6567 |
| Independent reflections | 2619 [R (int) = 0.0362] |
| Final R indices [I > 2sigma(I)] | R1 = 0.0421, wR2 = 0.0973 |
| R indices (all data) | R1 = 0.0479, wR2 = 0.1020 |

Figure 30:
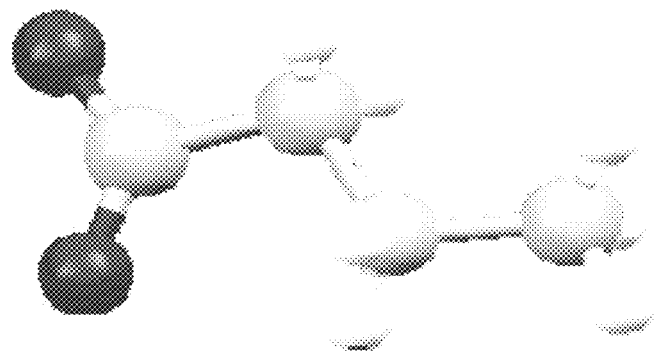
FIG. 30 is an illustration of sarcosine zwitterions as they exist in LM560, as described more fully in Example 5.
Figure 31:
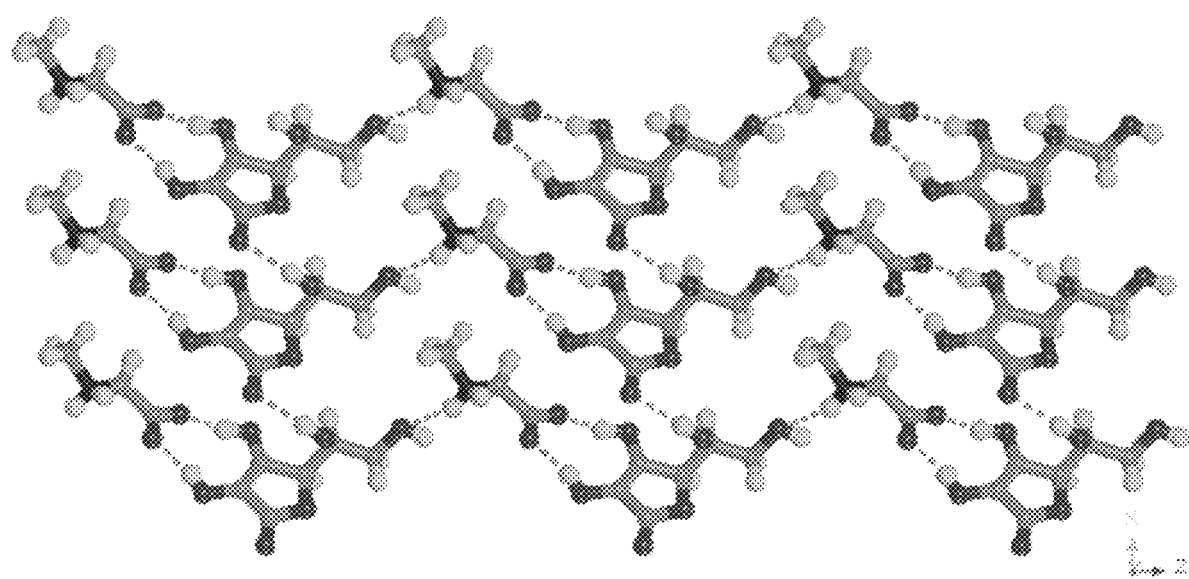
FIG. 31 shows the intermolecular interactions in LM560, as described more fully in Example 5.

Hydrogen bonding occurs between the alcohol moieties on the 5-membered ring of L-ascorbic acid molecules and the carboxylate moieties of the sarcosine zwitterions. An illustration of sarcosine zwitterions as they exist in LM560 is shown in the FIG. 30 of the accompanying drawings. One of the hydrogen atoms of the amino moiety in the sarcosine molecules hydrogen bonds with one of the hydroxyl moieties present on the aliphatic chain of L-ascorbic acid molecules resulting in the formation of hydrogen bonded chains. L-ascorbic acid molecules in one chain hydrogen bond with other L-ascorbic acid molecules present in adjacent chains resulting in the formation of two-dimensional sheets. These two-dimensional sheets are shown in FIG. 31 of the accompanying drawings.

Figure 32:
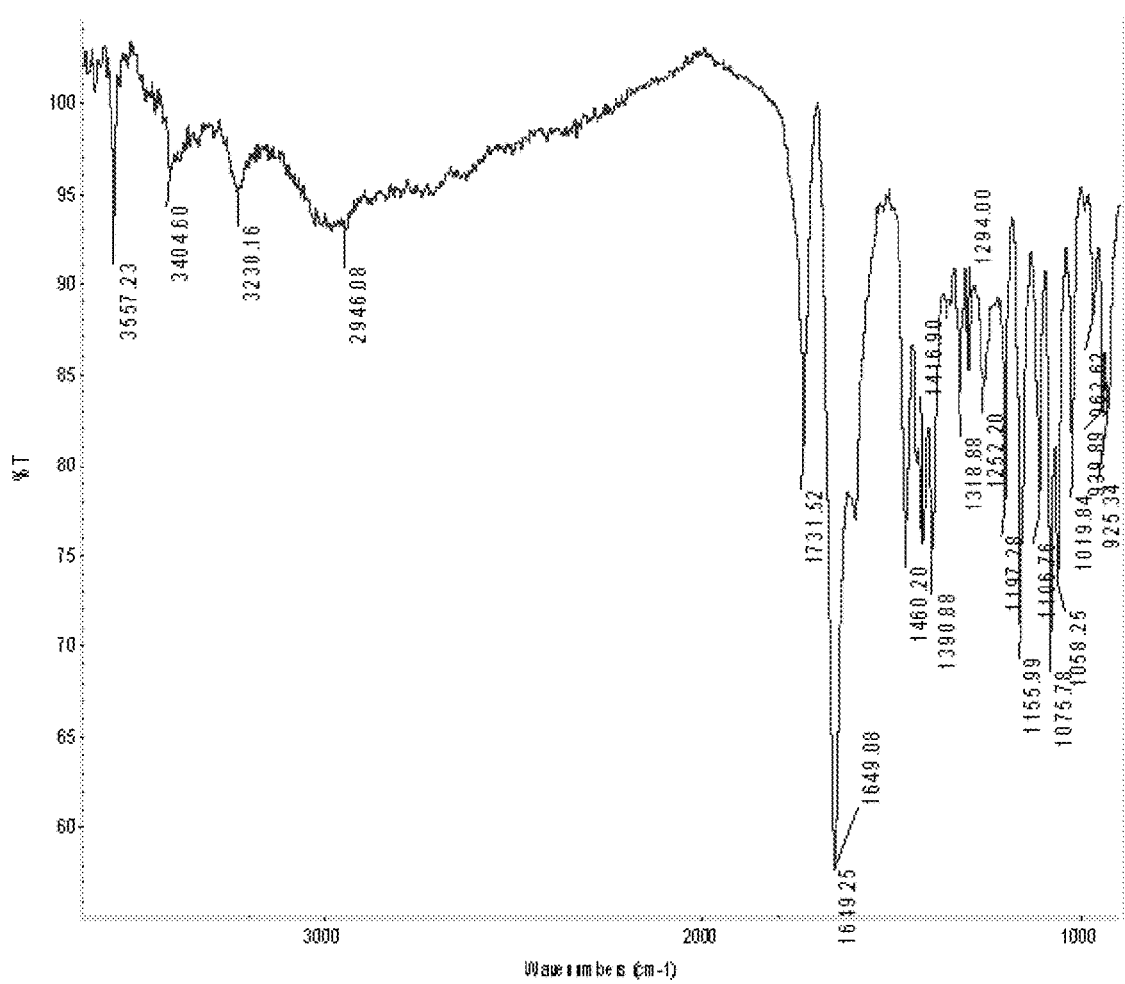
FIG. 32 shows an FT-IR spectroscopy image of LM560, as described more fully in Example 5.

LM560 was also characterized by FT-IR spectroscopy. The FT-IR spectra for LM560 is shown in FIG. 32 of the accompanying drawings.

Example 6

Co-Crystal of L-Ascorbic Acid and Nicotinic Acid—LM651

Figure 33:
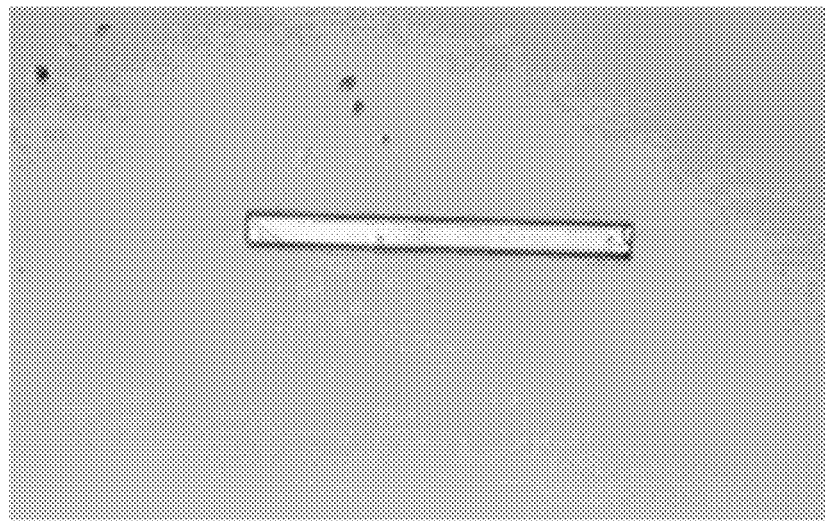
FIG. 33 is a digital microscopic image of LM651, as described more fully in Example 6.

L-ascorbic acid (99% pure, Sigma Aldrich) 88.06 mg (0.5000 mmol) and nicotinic acid (98% pure, Sigma Aldrich) 61.55 mg (0.5000 mmol) were dissolved in 6 mL of methanol and heated until a clear solution was obtained. The solution was slowly evaporated at room temperature and colorless crystals of 1:1 co-crystal of L-ascorbic acid and nicotinic acid (hereinafter "LM651") were harvested after two days. LM651 was also produced by solvent drop grinding with the following solvents: DMF, water, formic acid, acetic acid, and methanol, as well as by slurrying with methanol. FIG. 33 of the accompanying drawings shows a digital microscopic image of LM651. An illustration of the reaction scheme is below:

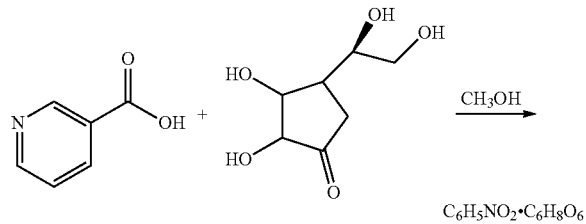

Figure 34:
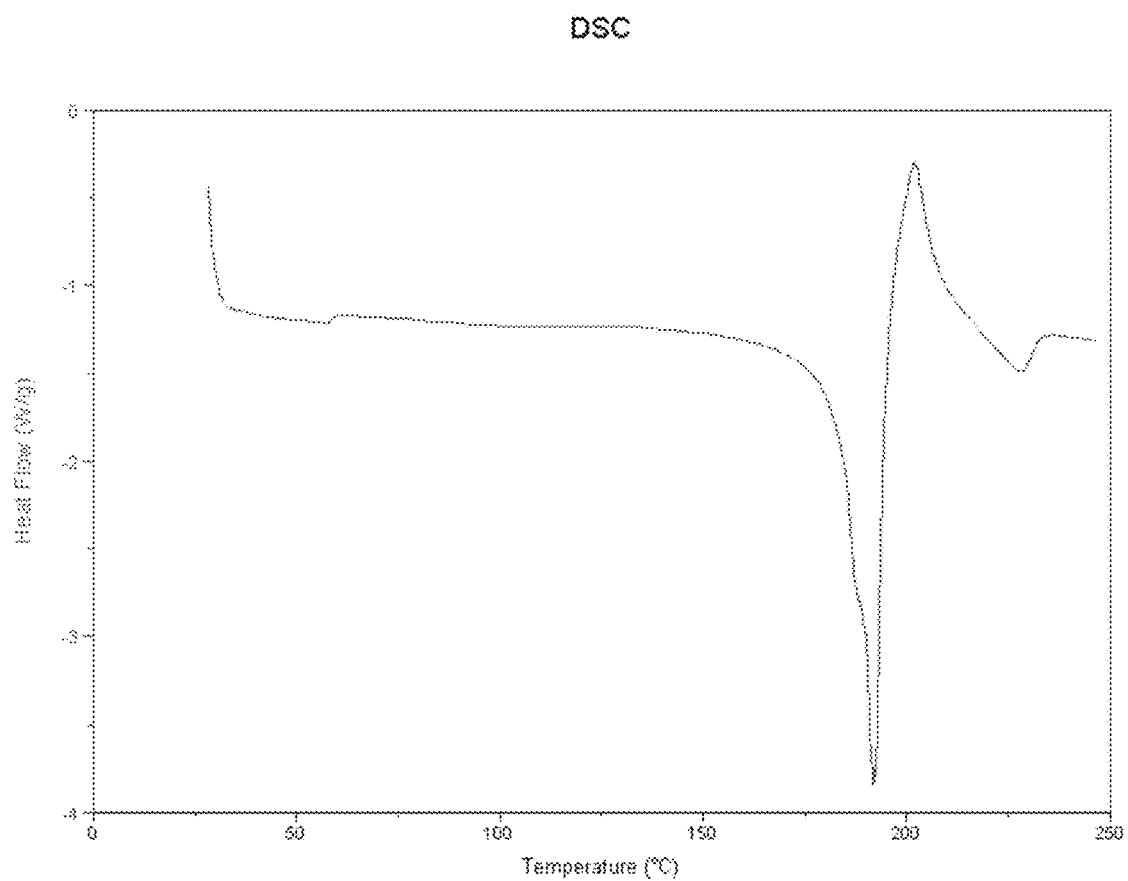
FIG. 34 is a DSC graph for LM651 as described more fully in Example 6.

The melting point of LM651 was determined by DSC analysis to be approximately 182° C. The DSC image of LM651 is shown in FIG. 34 of the accompanying drawings.

Figure 35:
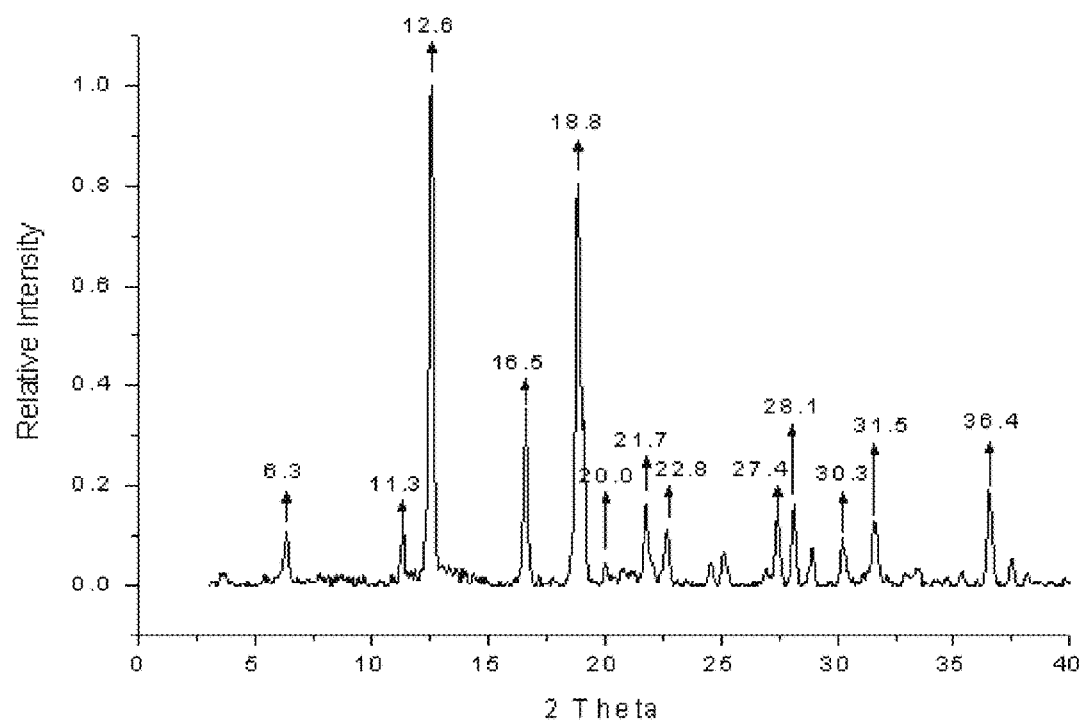
FIG. 35 shows an experimental XRPD pattern of LM651, as described more fully in Example 6, exhibiting major peaks at about the following positions: 6.2, 11.5, 12.5, 16.5, 18.7, 20.0, 21.7, 22.8, 23.0, 27.5, 28.3, 30.3, 31.5 and 36.4.
Figure 36:
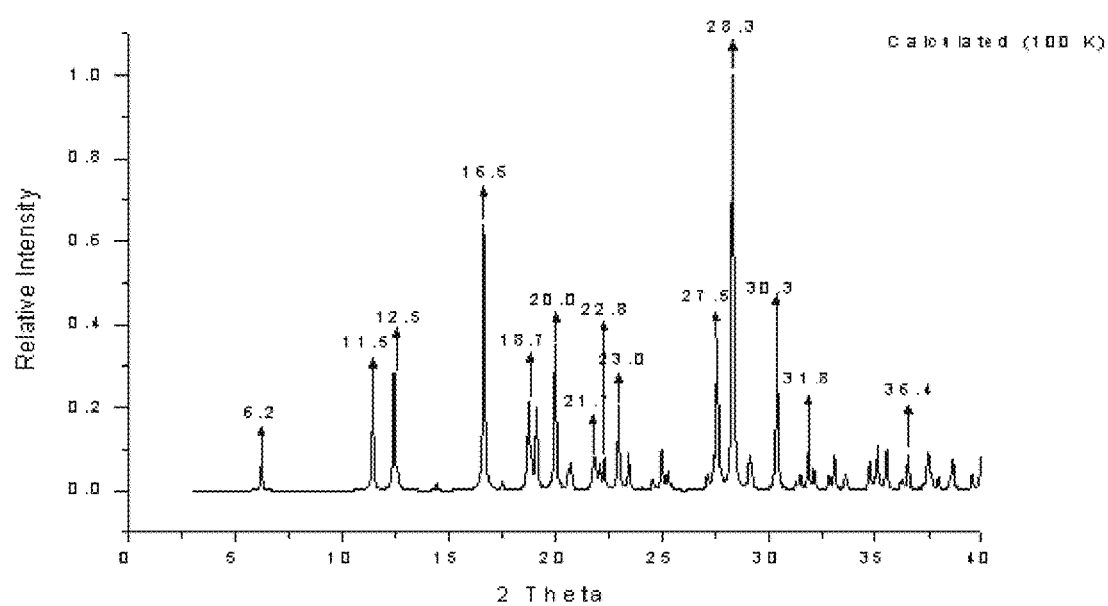
FIG. 36 shows a calculated XRPD pattern for LM651, as described more fully in Example 6.
Figure 37:
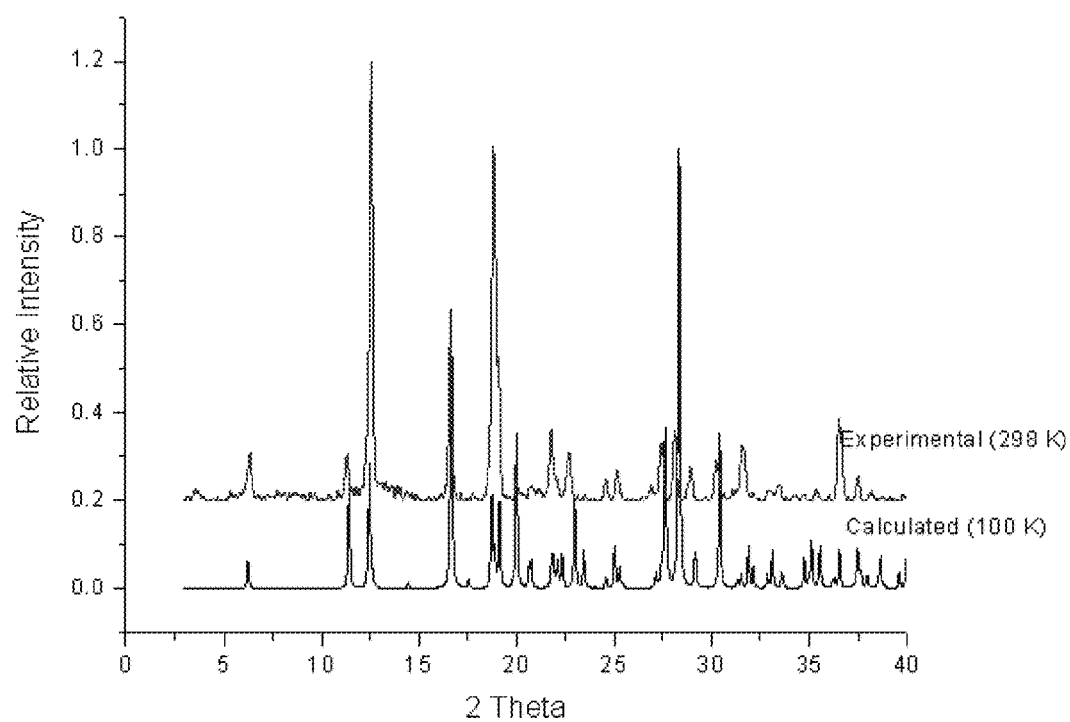
FIG. 37 shows a comparison of the experimental and calculated XRPD graphs for LM651, as described more fully in Example 6.

LM651 can be characterized using XRPD, and exhibited major peaks at about the following positions: 6.2, 11.5, 12.5, 16.5, 18.7, 20.0, 21.7, 22.8, 23.0, 27.5, 28.3, 30.3, 31.5 and 36.4 degrees. The XRPD graph for LM561 is shown in FIG. 35 of the accompanying drawings. FIG. 36 of the accompanying drawings shows the calculated XRPD values for LM651. FIG. 37 of the accompanying drawings shows a comparison between the experimental and calculated values for LM651.

Single crystal x-ray diffraction analysis was also performed on LM651 to determine the crystal structure and physical properties thereof. The crystallographic details are shown in the following table:

| LM651 Crystallographic Data | |
| --- | --- |
| Empirical formula | $C_{12}H_{13}NO_8$ |
| Formula weight | 299.23 |
| Temperature | 100(2) K |
| Wavelength | 0.71073 Å |
| Crystal system | Orthorhombic |
| Space group | $P2_12_12_1$ |
| Unit cell dimensions | a = 5.408(2) Å |
| | b = 8.040(3) Å |
| | c = 28.370(12) Å |
| | $\alpha = 90°$ |
| | $\beta = 90°$ |
| | $\gamma = 90°$ |
| Volume | 1233.7(9) Å$^3$ |
| Z | 4 |
| Density (calculated) | 1.611 mg/m$^3$ |
| Reflections collected | 7375 |
| Independent reflections | 2849 [R (int) = 0.0519] |
| Final R indices [I > 2sigma(I)] | R1 = 0.0687, wR2 = 0.1252 |
| R indices (all data) | R1 = 0.0479, wR2 = 0.1361 |

2-point charge assisted hydrogen bonding occurs between the two alcohol groups present on the five-membered ring of L-ascorbic acid molecule and the carboxylate moiety of the NA zwitterion (O—H . . . O: 2.478, 2.596 Å). The hydrogen atom on the aromatic nitrogen of the NA ring forms bifurcated hydrogen bonds with the carbonyl oxygen of the L-ascorbic acid molecule (N—H . . . O: 2.976 Å) and the carboxylate on the NA zwitterion (N—H . . . O: 2.963 Å).

Figure 38:
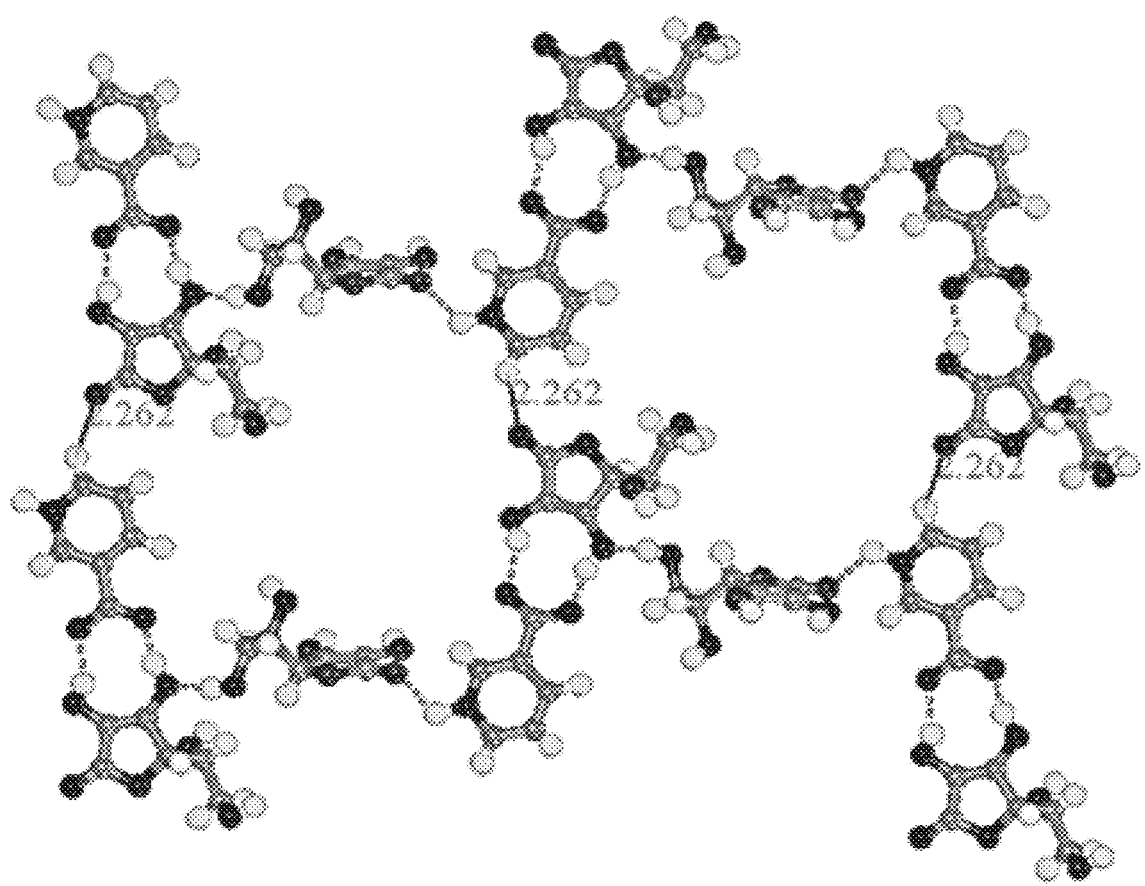
FIG. 38 shows the intermolecular interactions in LM651, as described more fully in Example 6.
Figure 39:
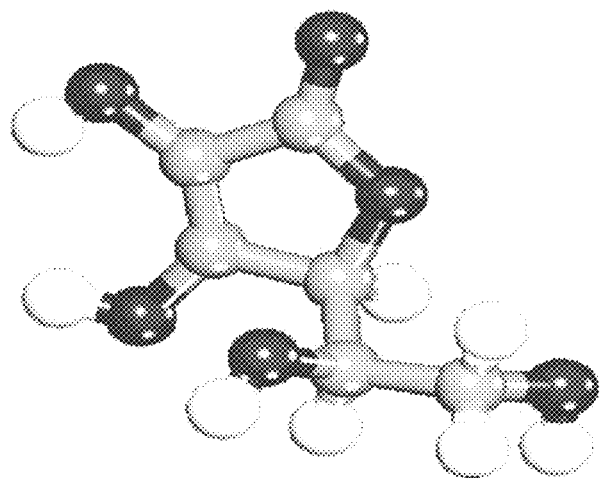
FIG. 39 is an illustration of an L-ascorbic acid molecule as it exists in LM651, as more fully described in Example 6.

The L-ascorbic acid molecules hydrogen bond with each other through multiple O—H . . . O hydrogen bonds forming a one dimensional rod-like chain which is in turn hydrogen bonded to the NA zwitterions. The intermolecular interactions in LM651 are shown in FIG. 38 of the accompanying drawings. An illustration of an L-ascorbic acid molecule as it exists in LM651 is shown in FIG. 39 of the accompanying drawings.

Figure 40:
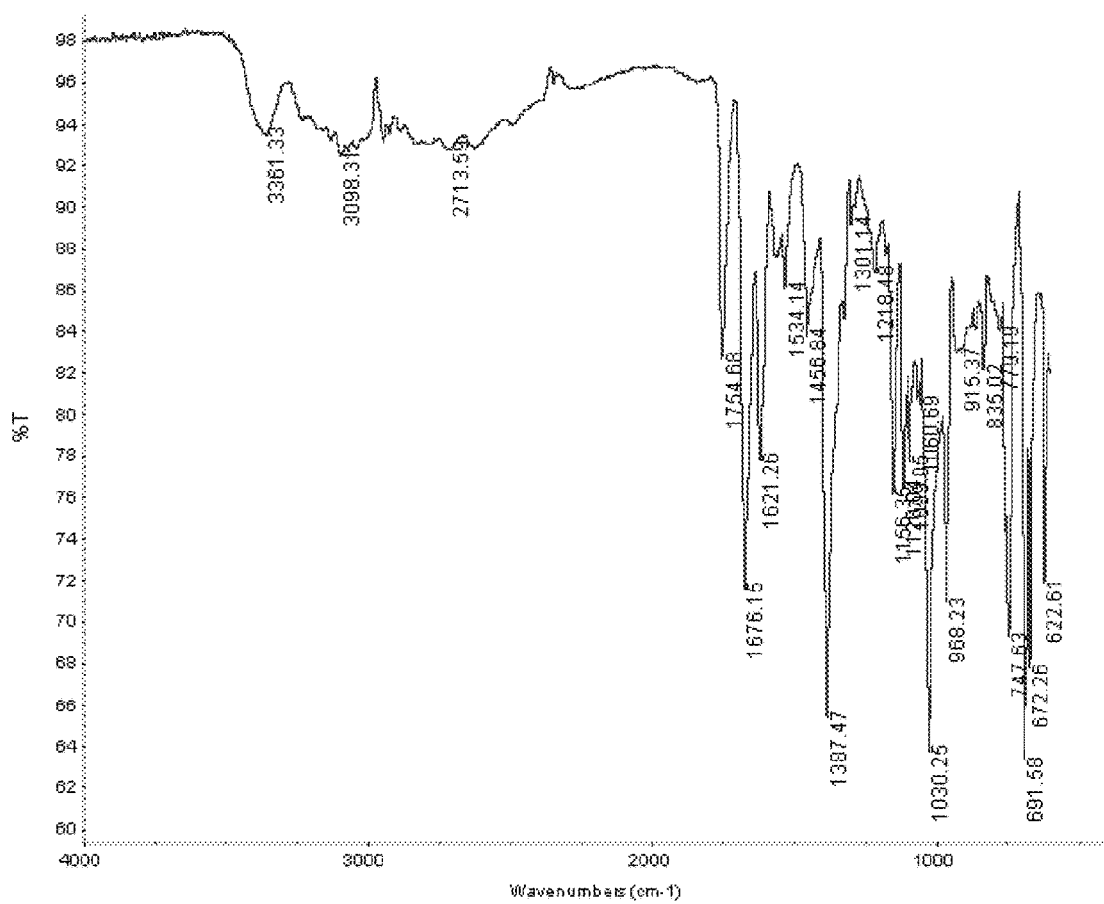
FIG. 40 shows the FT-IR spectra for LM651, as described more fully in Example 6.

LM651 was also characterized by FT-IR spectroscopy. The FT-IR spectra for LM651 is shown in FIG. 40 of the accompanying drawings.

Example 7

Hemihydrate of Co-Crystal of Ferulic Acid and (±) Baclofen—FABAC

Ferulic acid (99% pure, Acros Organics) 48.8 mg (0.250 mmol) and (±) baclofen (A.G. Scientific) 53.7 mg (0.250 mmol) were dissolved in 6 ml of 50/50 ethanol/water and heated until a clear solution was obtained. The solution was left to slowly evaporate at room temperature and fine needle-like crystals of the 1:1 co-crystal of ferulic acid and (±) baclofen (hereinafter, "FABAC") were obtained after 2 days. The x-ray single crystal structure revealed that FABAC is the hemihydrate of the 1:1 co-crystal of ferulic acid and (±) baclofen. The cocrystal can also be prepared by slurrying in 3 mL of 50/50 ethanol/water overnight with the above mentioned ratio. DSC analysis showed a phase change at about 157° C.

Figure 41:
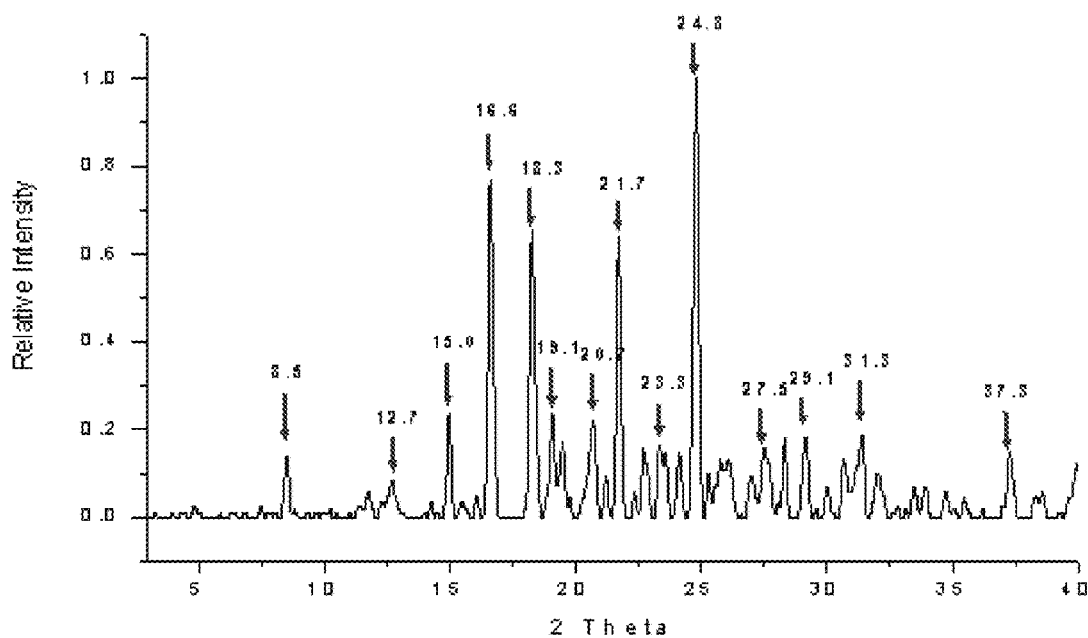
FIG. 41 shows an XRPD pattern of FABAC, as described more fully in Example 7, exhibiting major peaks at about the following positions: 8.6, 12.7, 15.0, 16.6, 18.3, 19.1, 20.7, 21.7, 23.3, 24.8, 27.6, 29.1, 31.3, 32.0, 37.3.

FABAC can be characterized using XRPD, and exhibited major peaks at about the following positions: 8.6, 12.7, 15.0, 16.6, 18.3, 19.1, 20.7, 21.7, 23.3, 24.8, 27.6, 29.1, 31.3, 32.0, 37.3°. The XRPD graph for FABAC is shown in FIG. 41 of the accompanying drawings.

Single crystal x-ray diffraction analysis was also performed on FABAC to determine the crystal structure and physical properties thereof. The crystallographic details are shown in the following table:

| FABAC Crystallographic Details | |
| --- | --- |
| Empirical formula | $C_{20}H_{23}ClNO_{6.5}$ |
| Formula weight | 416.84 |
| Temperature | 298(2) K |
| Wavelength | 0.71073 Å |
| Crystal system | Monoclinic |
| Space group | $P2_1/c$ |
| Unit cell dimensions | a = 18.491(7) Å |
| | b = 7.765(3) Å |
| | c = 28.207(10) Å |
| | $\alpha = 90°$ |
| | $\beta = 98.628(9)°$ |
| | $\gamma = 90°$ |
| Volume | 4004(2) Å$^3$ |
| Z | 8 |
| Density (calculated) | 1.383 Mg/m$^3$ |
| Reflections collected | 19371 |
| Independent reflections | 7062 [R(int) = 0.1037] |
| Final R indices [I > 2sigma(I)] | R1 = 0.0895, wR2 = 0.1485 |
| R indices (all data) | R1 = 0.1691, wR2 = 0.1778 |

Figure 42:
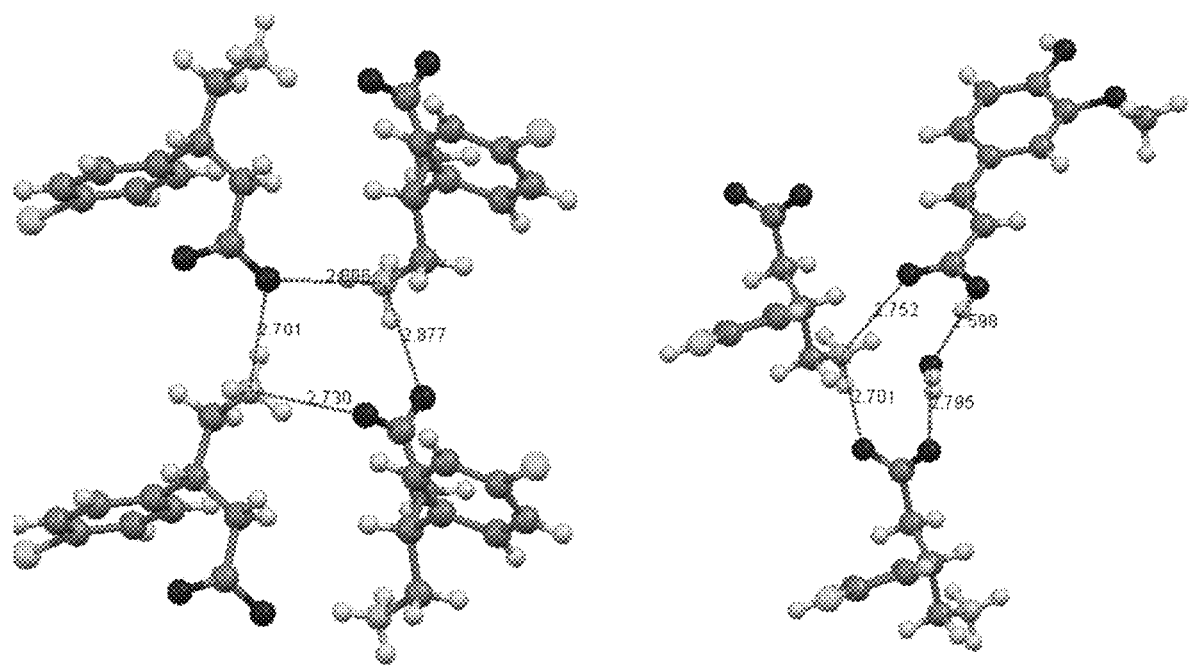
FIG. 42 shows the intermolecular interactions in FABAC, as described more fully in Example 7.

The crystal structure reveals that there are two independent baclofen zwitterions, two independent ferulic acid molecules and one independent water molecule in the asymmetric unit. Baclofen zwitterions interact through NH . . . O hydrogen bonds to form tetrameric clusters via an Etter $R^3_4(10)$ (NH . . . O: 2.701-2.877 Å) graph set. A series of charge assisted N—H . . . O and OH . . . O hydrogen bonds result in a hydrogen bonded complex between a water molecule, two baclofen zwitterions and the carboxylic acid moiety of a ferulic acid molecule (NH . . . O: 2.701, 2.752 Å, OH . . . O: 2.598, 2.795 Å). The other crystallographically independent ferulic acid molecule forms a hydrogen bond directly to the carboxylate moiety of the second baclofen molecule. Overall, the crystal packing consists of a three-dimensional hydrogen-bonded network. These intermolecular interactions in FABAC are shown in FIG. 42 of the accompanying drawings.

Example 8

Hemihydrate and Anhydrate Co-Crystal of Gallic Acid and Caffeine—GACAF

Gallic acid (98% pure, Acros Organics) 50.3 mg (0.296 mmol) and caffeine anhydrous (99% pure, Sigma Aldrich) 57.4 mg (0.296 mmol) were dissolved in 5 ml of methanol until a clear solution was obtained. The solution was left for slow evaporation at room temperature for 14 days. This slow evaporation yielded colorless crystals of the hemihydrate of the 1:1 co-crystal of gallic acid and caffeine (hereinafter, "GACAF"). DSC analysis showed phase changes at about 136° C. and about 243° C.

Single crystal x-ray diffraction analysis was performed on GACAF to determine the crystal structure and physical properties thereof. The crystallographic details are shown in the following table:

| GACAF Crystallographic Data | |
| --- | --- |
| Empirical formula | $C_{15}H_{17}N_4O_{7.5}$ |
| Formula weight | 373.33 |
| Temperature | 100(2) K |
| Wavelength | 0.71073 Å |
| Crystal system | Monoclinic |
| Space group | C2/c |
| Unit cell dimensions | a = 19.966(4) Å |
| | b = 15.800(3) Å |
| | c = 13.111(3) Å |
| | α = 90°. |
| | β = 130.780(3)°. |
| | γ = 90°. |
| Volume | 3131.8(11) Å$^3$ |
| Z | 8 |
| Density (calculated) | 1.584 Mg/m$^3$ |
| Reflections collected | 9278 |
| Independent reflections | 3553 [R(int) = 0.0325] |
| Final R indices [I > 2sigma(I)] | R1 = 0.0439, wR2 = 0.1115 |
| R indices (all data) | R1 = 0.0529, wR2 = 0.1172 |

Figure 43:
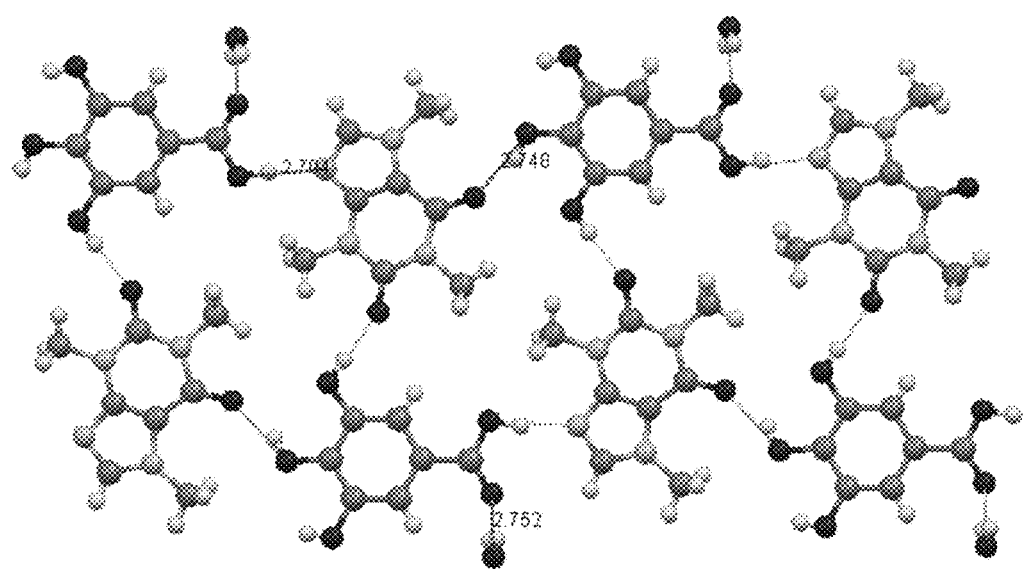
FIG. 43 shows the intermolecular interactions in GACAF, as described more fully in Example 8.

The crystal structure reveals a one point hydrogen bond between the hydroxyl moiety from the gallic acid molecule and the carbonyl moiety from a caffeine molecule (O—H . . . O: 2.703-2.748 Å). The carbonyl moiety from the gallic acid molecule accepts a hydrogen bond from a water molecule (O—H . . . O: 2.752-2.855 Å). The overall result is that hydrogen bonding occurs between a gallic acid molecule, a caffeine molecule and a water molecule to form a sheet. The intermolecular interactions in GACAF are shown in FIG. 43 of the accompanying drawings.

Figure 64:
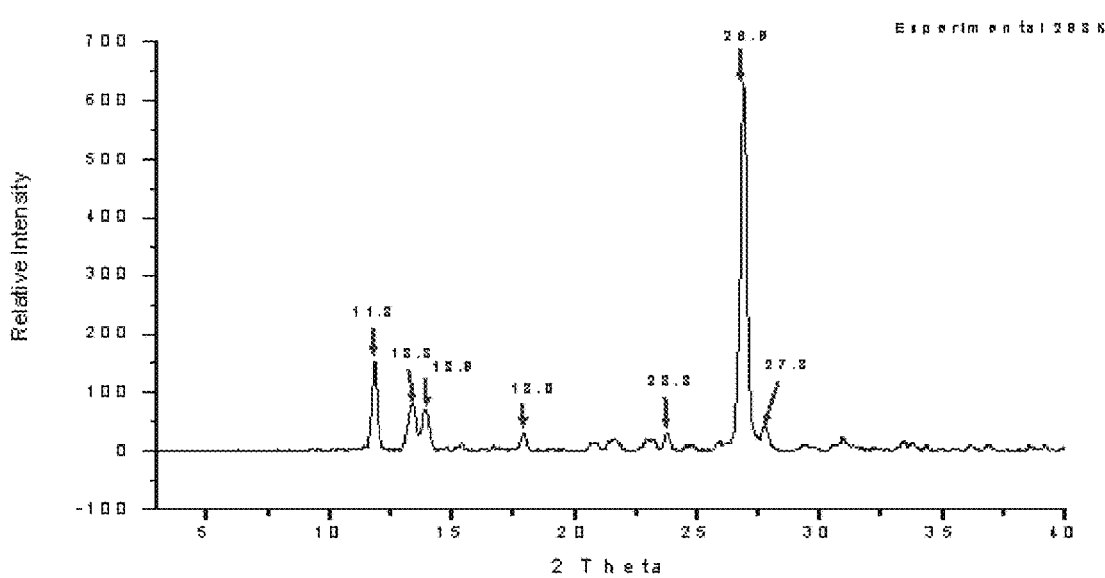
FIG. 64 shows the XRPD spectra for GACAF-D, as described more fully in Example 8, exhibiting major peaks at about the following positions: 11.8, 13.3, 13.9, 18.0, 23.8, 26.9, and 27.8 degrees.

GACAF can be slowly converted to an anhydrate form (hereinafter, "GACAF-D"). The co-crystal of GACAF-D was obtained through solvent drop grinding of gallic acid (98% pure, Acros Organics) 50.0 mg (0.293 mmol) and caffeine anhydrous (99% pure, Sigma Aldrich) 57.0 mg (0.294 mmol) and methanol (10 μl) for 20 minutes using the instrument Spex Sampler Prep 8000M Mixer/Mill. The solid was heated at 135° C. to evaporate the water and the result was analyzed. The powder x-ray diffraction pattern reveals the anhydrate co-crystal of GACAF-D. The XRPD for GACAF-D is shown in FIG. 64 of the accompanying drawings, exhibiting major peaks at about the following positions: 11.8, 13.3, 13.9, 18.0, 23.8, 26.9, and 27.8 degrees.

Example 9

Trihydrate of Co-Crystal of Gallic Acid and Nicotinic Acid—GANAC

Gallic acid (98% pure, Acros Organics) 59.5 mg (0.348 mmol) and nicotinic acid (98% pure, Sigma Aldrich) 49.9 mg (0.405 mmol) were dissolved in 5 ml of methanol until a clear solution was obtained. The solvent was allowed to slowly evaporate under ambient conditions and large irregularly shaped colorless crystals were obtained after three days. The X-ray single crystal analysis reveals that the crystal is the trihydrate of the 1:1 co-crystal of gallic acid and nicotinic acid (hereinafter, "GANAC"). DSC analysis revealed phase changes at about 119° C. and about 211° C.

Figure 44:
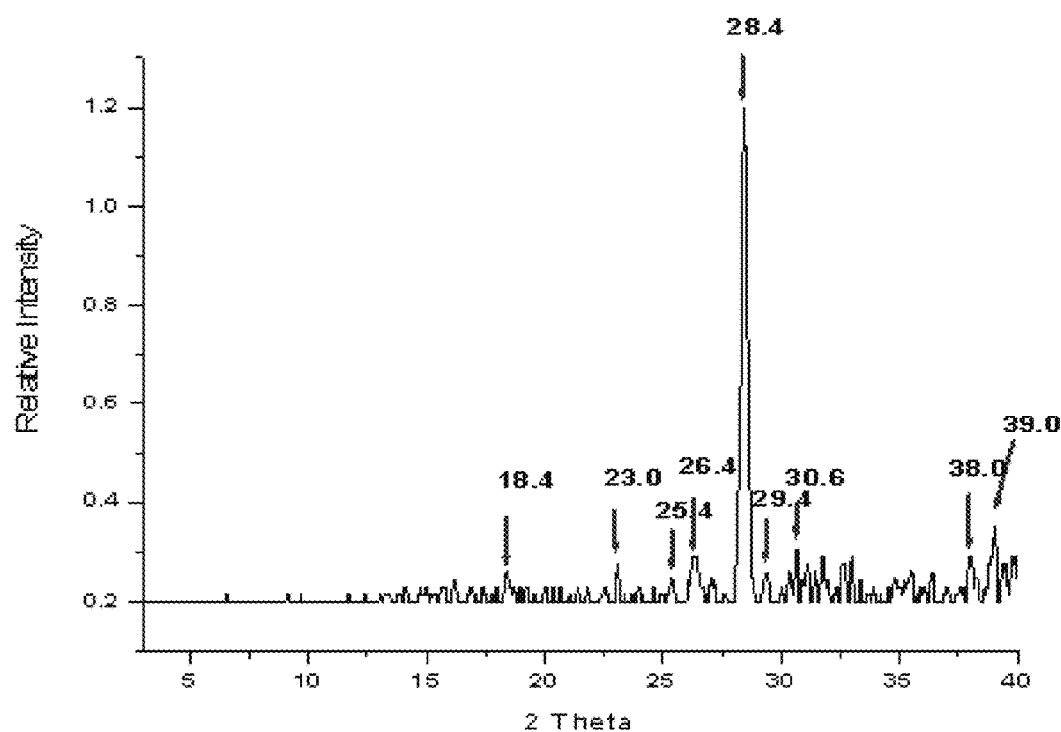
FIG. 44 shows an XRPD pattern of GANAC, as described more fully in Example 9, exhibiting major peaks at about the following positions: 18.4, 23.0, 25.4, 26.4, 28.4, 29.4, 30.6, 38.0 and 39.0.

GANAC can be characterized using XRPD, and exhibited major peaks at about the following positions: 18.4, 23.0, 25.4, 26.4, 28.4, 29.4, 30.6, 38.0 and 39.0°. The XRPD graph for GANAC is shown in FIG. 44 of the accompanying drawings.

Single crystal x-ray diffraction analysis was also performed on GANAC to determine the crystal structure and physical properties thereof. The crystallographic details are shown in the following table:

| GANAC Crystallographic Data | |
| --- | --- |
| Empirical formula | $C_{26}H_{28}N_2O_{17}$ |
| Formula weight | 640.50 |
| Temperature | 100(2) K |
| Wavelength | 0.71073 Å |
| Crystal system | Triclinic |
| Space group | P 1 |
| Unit cell dimensions | a = 11.742(5) Å |
| | b = 11.756(5) Å |
| | c = 12.399(5) Å |
| | α = 92.628(9)°. |
| | β = 115.898(8)°. |
| | γ = 115.570(9)°. |
| Volume | 1329.7(9) Å$^3$ |
| Z | 4 |
| Density (calculated) | 1.600 Mg/m$^3$ |
| Reflections collected | 8110 |
| Independent reflections | 5847 [R(int) = 0.0473] |
| Final R indices [I > 2sigma(I)] | R1 = 0.0808, wR2 = 0.2040 |
| R indices (all data) | R1 = 0.1153, wR2 = 0.2270 |

Figure 45:
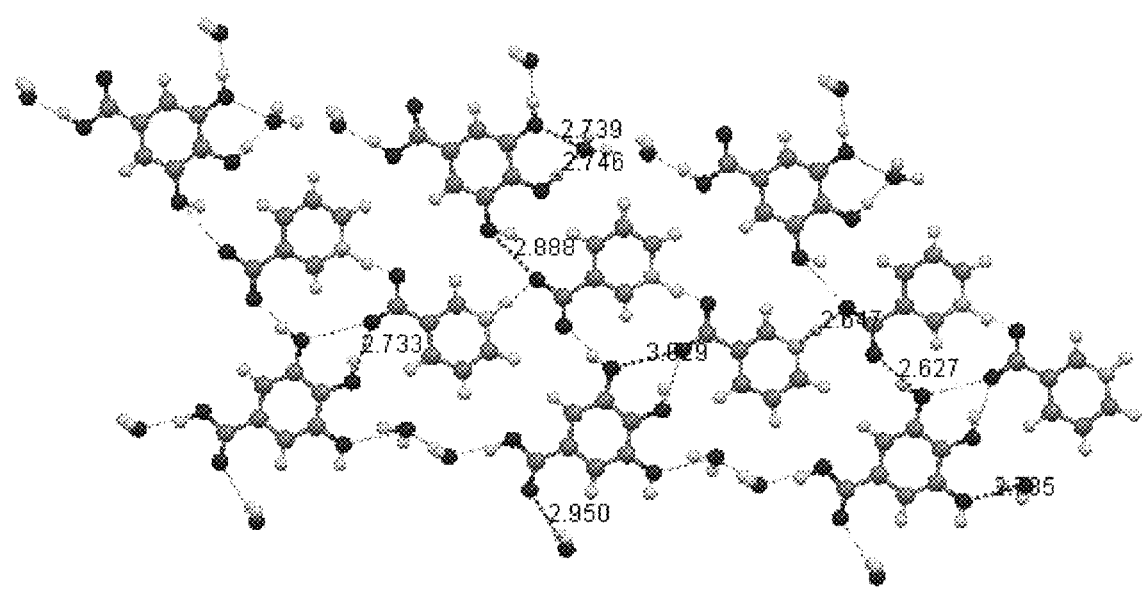
FIG. 45 shows the intermolecular interactions in GANAC, as described more fully in Example 9.

The crystal structure reveals that the nicotinic acid molecule exists as a zwitterion. Two hydroxyl moieties of a gallic acid molecule donate a bifurcated hydrogen bond to the carbonyl moiety of the nicotinic acid zwitterion (O—H . . . O: 2.733-3.029 Å). The nicotinic acid zwitterions hydrogen bonds with each other through amine to carbonyl hydrogen bond interaction (N—H . . . O: 2.647 Å). Two water molecules are incorporated within the sheet joining two molecules of gallic acid and the third water molecule joins each layer. Overall a tape-like structure is formed between gallic acid molecules and nicotinic acid zwitterions. The intermolecular interactions in GANAC are shown in FIG. 45 of the accompanying drawings.

Example 10

Hydrate of Co-Crystal of Gallic Acid and Theobromine—GATBR

Gallic acid (98% pure, Acros Organics) 50.5 mg (0.297 mmol) and theobromine (TCI America) 53.3 mg (0.296 mmol) were dissolved in 6 ml of water/ethanol and heated until a clear solution was obtained. The solution was allowed to slowly evaporate at room temperature. Colorless rodshaped crystals were obtained after 6 days. The X-ray single crystal structure revealed the crystals to be the hydrate of the 1:1 co-crystal of gallic acid and theobromine (hereinafter, "GATBR). The cocrystal can also be prepared by solvent drop grinding. DSC analysis revealed phase changes at about 116° C. and about 270° C.

Figure 46:
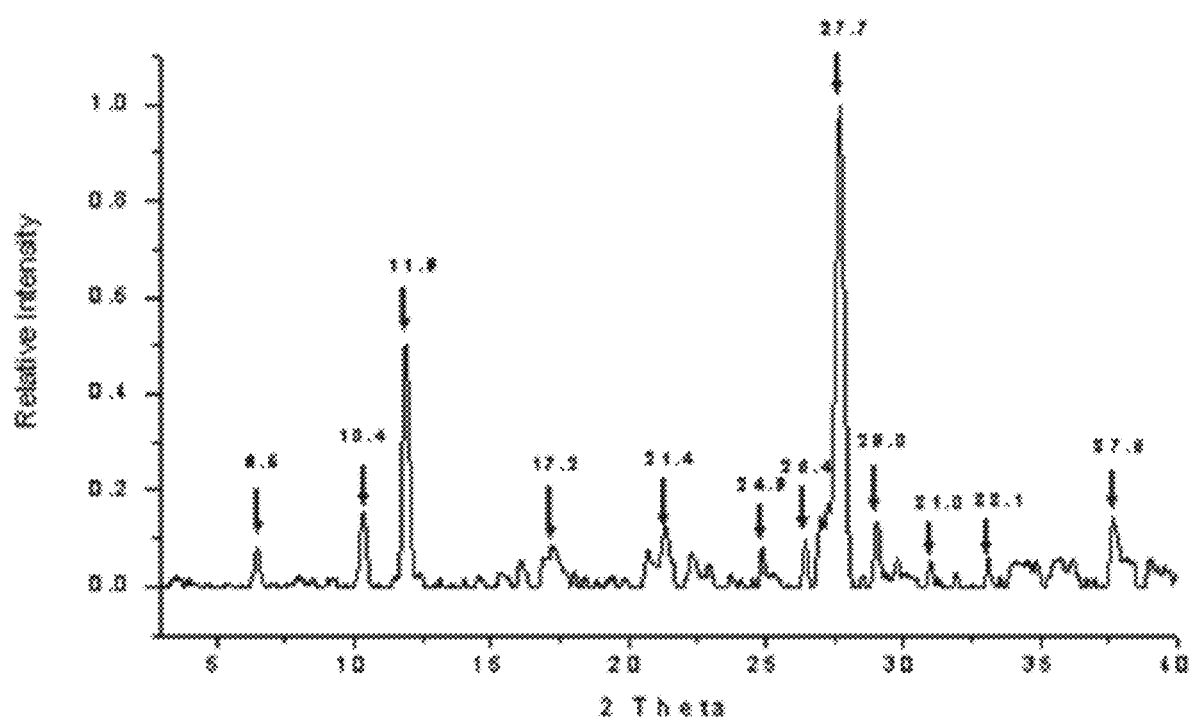
FIG. 46 shows an XRPD pattern of GATBR, as described more fully in Example 10, exhibiting major peaks at about the following positions: 6.5, 10.4, 11.9, 17.2, 21.4, 24.9, 26.4, 27.7, 29.0, 31.0, 33.1, and 37.6.

GATBR can be characterized using XRPD, and exhibited major peaks at about the following positions: 6.5, 10.4, 11.9, 17.2, 21.4, 24.9, 26.4, 27.7, 29.0, 31.0, 33.1, 37.6°. The XRPD graph for GATBR is shown in FIG. 46 of the accompanying drawings.

Single crystal x-ray diffraction analysis was also performed on GATBR to determine the crystal structure and physical properties thereof. The crystallographic details are shown in the following table:

| GATBR Crystallographic Data | |
|---|---|
| Empirical formula | $C_{14}H_{16}N_4O_9$ |
| Formula weight | 384.31 |
| Temperature | 173(2) K |
| Wavelength | 0.71073 Å |
| Crystal system | Monoclinic |
| Space group | C2/c |
| Unit cell dimensions | a = 27.737(13) Å |
| | b = 6.664(3) Å |
| | c = 17.345(8) Å |
| | α = 90°. |
| | β = 92.962(9)°. |
| | γ = 90°. |
| Volume | 3201(3) Å$^3$ |
| F(000) | 1600 |
| Z | 8 |
| Density (calculated) | 1.595 Mg/m$^3$ |
| Reflections collected | 7565 |
| Independent reflections | 2814 [R(int) = 0.0693] |
| Final R indices [I > 2sigma(I)] | R1 = 0.0573, wR2 = 0.1450 |
| R indices (all data) | R1 = 0.0716, wR2 = 0.1535 |

Figure 47:
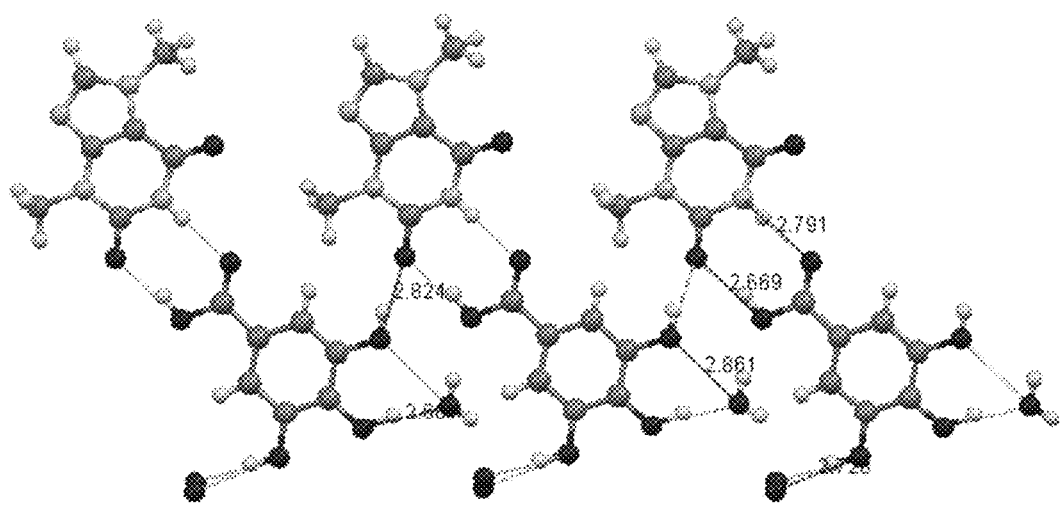
FIG. 47 shows the intermolecular interactions in GATBR, as described more fully in Example 10.

The crystal structure reveals that molecules of gallic acid and theobromine form carboxylic acid-amide dimer supramolecular heterosynthon (NH . . . O: 2.791 Å, OH . . . O: 2.669 Å). A phenolic moiety from the gallic acid molecule donates a hydrogen bond to the carbonyl group of the theobromine molecule of an adjacent dimer and therefore generates an undulating tape of dimers (OH . . . O: 2.824 Å). These tapes of dimers are further connected through water molecules to tapes that lie above and below (OH . . . O: 2.811 Å) so that the overall crystal packing can be described as a three dimensional network. The intermolecular interactions in GATBR are shown in FIG. 47 of the accompanying drawings.

Example 11

Co-Crystal of L-Ascorbic Acid and Nicotinamide—KA1013

L-ascorbic acid (99% pure, purchased from Sigma Aldrich, used as received, 88.06 mg, 0.5000 mmol) and nicotinamide (99% pure, purchased from Sigma Aldrich, used as received, 61.06 mg, 0.5000 mmol) were dissolved in 5 mL of MeOH and heated until a clear solution was obtained. The solution was slowly evaporated at room temperature and colorless crystals were harvested after about four days. This slow evaporation yielded the 1:1 co-crystal of L-ascorbic acid and nicotinamide (hereinafter, "KA1013"). DSC analysis revealed a phase change at about 151° C.

Figure 48:
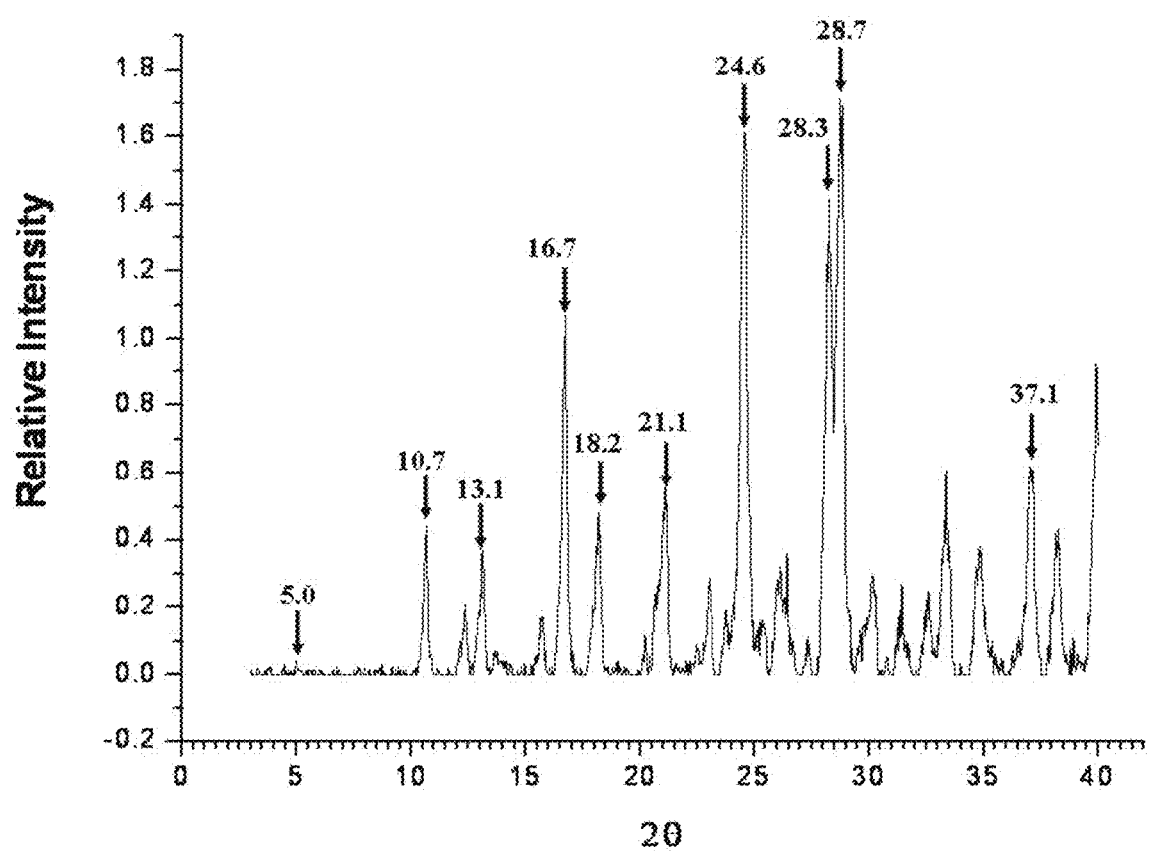
FIG. 48 shows an XRPD pattern of KA1013, as described more fully in Example 11, exhibiting major peaks at about the following positions: 5.0, 10.7, 13.1, 16.7, 18.2, 21.1, 24.6, 28.3, 28.7 and 37.1.

KA1013 can be characterized using XRPD, and exhibited major peaks at about the following positions: 5.0, 10.7, 13.1, 16.7, 18.2, 21.1, 24.6, 28.3, 28.7 and 37.1 degrees. The XRPD graph for KA013 is shown in FIG. 48 of the accompanying drawings.

Single crystal x-ray diffraction analysis was also performed on KA1013 to determine the crystal structure and physical properties thereof. The crystallographic details are shown in the following table:

| KA1013 Crystallographic Data | |
|---|---|
| Empirical formula | $C_{24}H_{28}N_4O_{14}$ |
| Formula weight | 596.50 |
| Temperature | 298(2) K |
| Wavelength | 0.71073 Å |
| Crystal system | Triclinic |
| Space group | P1 |
| Unit cell dimensions | a = 5.094(3) Å |
| | b = 7.399(4) Å |
| | c = 17.119(8) Å |
| | α = 93.108(8)°. |
| | β = 93.930(8)°. |
| | γ = 97.696(8)°. |
| Volume | 636.5(5) Å$^3$ |
| Z | 2 |
| Density (calculated) | 1.556 Mg/m$^3$ |
| Reflections collected | 5832 |
| Independent reflections | 2226 [R(int) = 0.0701] |
| Final R indices [I > 2sigma(I)] | R1 = 0.0666, wR2 = 0.1412 |
| R indices (all data) | R1 = 0.0853, wR2 = 0.1506 |

Figure 49:
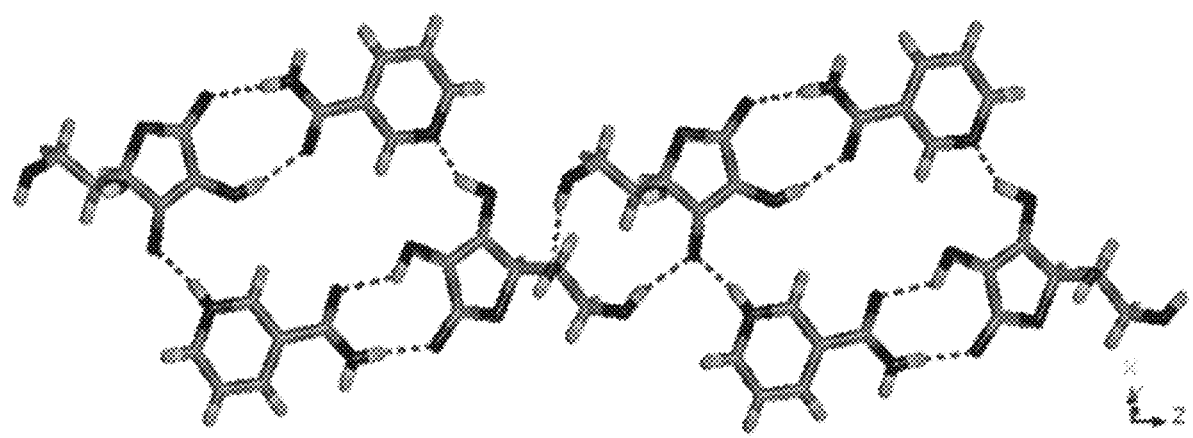
FIG. 49 shows the intermolecular interactions in KA1013, as described more fully in Example 11.

The single crystal x-ray structure analysis reveals that the asymmetric unit contains two independent molecules of both L-ascorbic acid and nicotinamide. The complex forms a quaternary unit with pseudoinversion centre. These quaternary units are further connected to form tapes. The intermolecular hydrogen bondings in KA013 are shown in FIG. 49 of the accompanying drawings.

Example 12

Co-Crystal of L-Ascorbic Acid and Iso-Nicotinamide—KA1014

L-ascorbic acid (99% pure, (Sigma Aldrich) 88.06 mg (0.5000 mmol) and iso-nicotinamide (99% pure, Sigma Aldrich) 61.06 mg (0.5000 mmol) were dissolved in 5 mL of methanol and heated until a clear solution was obtained. The solution was allowed to slowly evaporate at room temperature and colorless crystals were harvested after about five days. This slow evaporation yielded a 1:1 co-crystal of L-ascorbic acid and iso-nicotinamide (hereinafter, "KA1014"). DSC analysis showed a phase change at about 152° C.

Figure 50:
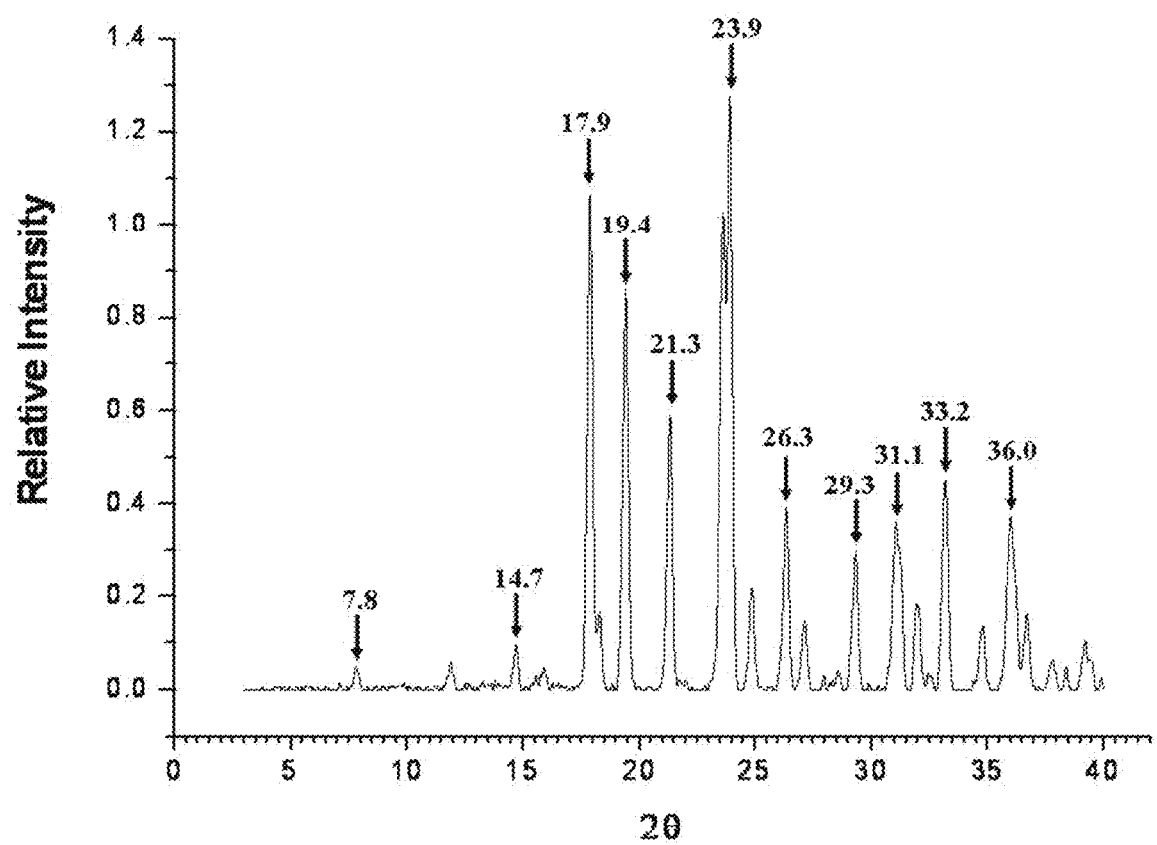
FIG. 50 shows an XRPD pattern of KA1014, as described more fully in Example 12, exhibiting major peaks at about the following positions: 7.8, 14.7, 17.9, 19.4, 21.3, 23.9, 26.3, 29.3, 31.1, 33.2 and 36.0.

KA1014 can be characterized using XRPD, and exhibited major peaks at about the following positions: 7.8, 14.7, 17.9, 19.4, 21.3, 23.9, 26.3, 29.3, 31.1, 33.2 and 36.0 degrees. The XRPD graph for KA1014 is shown in FIG. 50 of the accompanying drawings.

Single crystal x-ray diffraction analysis was also performed on KA1014 to determine the crystal structure and physical properties thereof. The crystallographic details are shown in the following table:

| KA1014 Crystallographic Data | |
|---|---|
| Empirical formula | $C_{12}H_{14}N_2O_7$ |
| Formula weight | 298.25 |
| Temperature | 100(2) K |
| Wavelength | 0.71073 Å |
| Crystal system | Orthorhombic |

| KA1014 Crystallographic Data | |
| --- | --- |
| Space group | P2₁2₁2₁ |
| Unit cell dimensions | a = 5.7932(12) Å |
| | b = 9.807(2) Å |
| | c = 23.018(5) Å |
| | α = 90°. |
| | β = 90°. |
| | γ = 90°. |
| Volume | 1307.7(5) Å$^3$ |
| Z | 4 |
| Density (calculated) | 1.515 Mg/m$^3$ |
| Reflections collected | 11313 |
| Independent reflections | 3055 [R(int) = 0.0374] |
| Final R indices [I > 2sigma(I)] | R1 = 0.0424, wR2 = 0.0929 |
| R indices (all data) | R1 = 0.0464, wR2 = 0.0950 |

Figure 51:
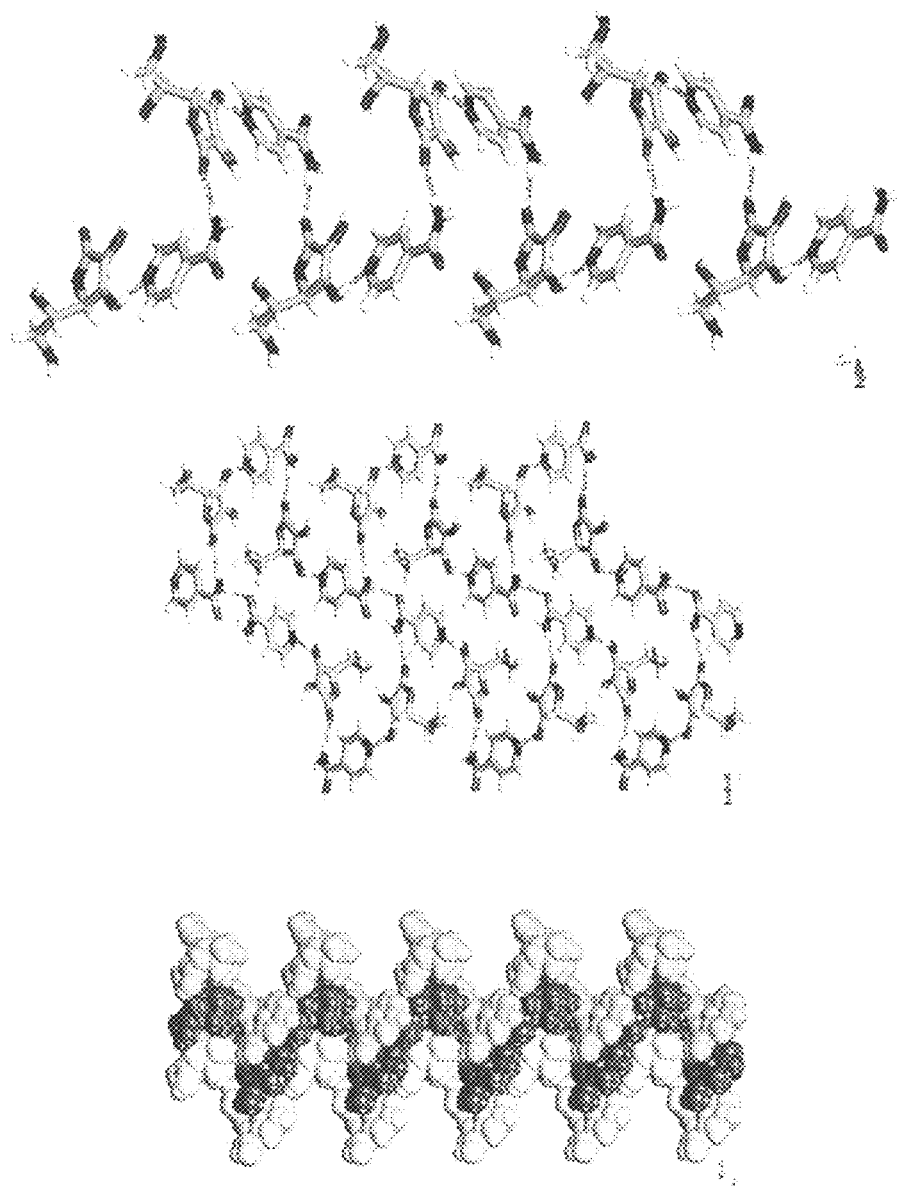
FIG. 51 shows the intermolecular interactions in KA1014, as described more fully in Example 12.

The single crystal x-ray structure analysis reveals that KA1014 is a 1:1 cocrystal of L-ascorbic acid and iso-nicotinamide. L-ascorbic acid molecules and iso-nicotinamide molecules interact through one point hydrogen bonds (O—H . . . N, O . . . N: 2.692 Å) between the hydroxyl group present at C-3 of L-ascorbic acid molecule and the aromatic nitrogen of iso-nicotinamide molecules. These dimeric units are further connected by N—H . . . O (N . . . O: 2.882 Å) hydrogen bonds formed between carbonyl moieties of L-ascorbic acid and amide moieties of iso-nicotinamide molecules and thereby form helical chains. The intermolecular interactions in KA1014 are shown in FIG. 51 of the accompanying drawings.

Example 13

Ethanol Solvate of Co-Crystal of L-Ascorbic Acid and Nicotinamide—KA1015

L-Ascorbic acid (99% pure, Sigma Aldrich) 88.06 mg (0.5000 mmol) and nicotinamide (99% pure, Sigma Aldrich) 61.06 mg (0.5000 mmol) were dissolved in 5 mL of EtOH and heated until a clear solution was obtained. The solution was slowly evaporated at room temperature and colorless crystals were harvested after ca. 4 days. This slow evaporation yielded the ethanol solvate of the 1:1 co-crystal of L-ascorbic acid and nicotinamide (hereinafter, "KA1015"). DSC analysis showed phase changes at about 86° C. and about 155° C.

Crystals of KA1015 lose ethanol solvent molecules and convert to the unsolvated cocrystal KA1013.

KA1015 can also be made by slurrying L-Ascorbic acid and nicotinamide in ethanol for about 18 hours.

Single crystal x-ray diffraction analysis was also performed on KA015 to determine the crystal structure and physical properties thereof. The crystallographic details are shown in the following table:

| KA1015 Crystallographic Data | |
| --- | --- |
| Empirical formula | C₂₆H₃₄N₄O₁₅ |
| Formula weight | 642.57 |
| Temperature | 100(2) K |
| Wavelength | 0.71073 Å |
| Crystal system | Triclinic |
| Space group | P1 |
| Unit cell dimensions | a = 5.048(3) Å |
| | b = 7.368(5) Å |
| | c = 19.873(13) Å |
| | α = 97.394(12)°. |
| | β = 96.086(13)°. |
| | γ = 97.227(12)°. |

| KA1015 Crystallographic Data | |
| --- | --- |
| Volume | 721.5(8) Å$^3$ |
| Z | 2 |
| Density (calculated) | 1.479 Mg/m$^3$ |
| Reflections collected | 6924 |
| Independent reflections | 2524 [R(int) = 0.0842] |
| Final R indices [I > 2sigma(I)] | R1 = 0.0633, wR2 = 0.1429 |
| R indices (all data) | R1 = 0.0865, wR2 = 0.1674 |

Figure 52:
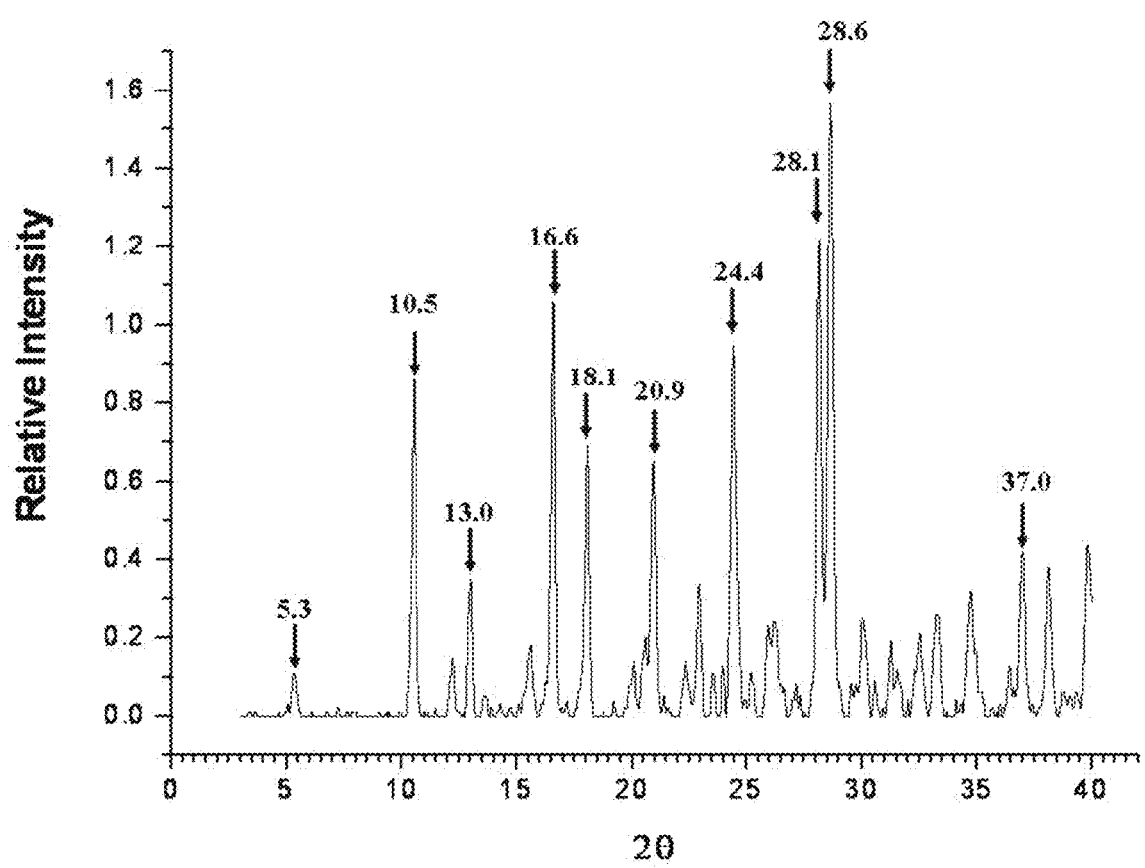
FIG. 52 shows an XRPD pattern of KA1015, as described more fully in Example 13, exhibiting major peaks at about the following positions: 5.3, 10.5, 13.0, 16.6, 18.1, 20.9, 24.4, 28.1, 28.6, and 37.0.

KA1015 can be characterized using XRPD, and exhibited major peas at about the following positions: 5.3, 10.5, 13.0, 16.6, 18.1, 20.9, 24.4, 28.1, 28.6, and 37.0 degrees. The XRPD graph for KA1015 is shown in FIG. 52 of the accompanying drawings.

Figure 53:
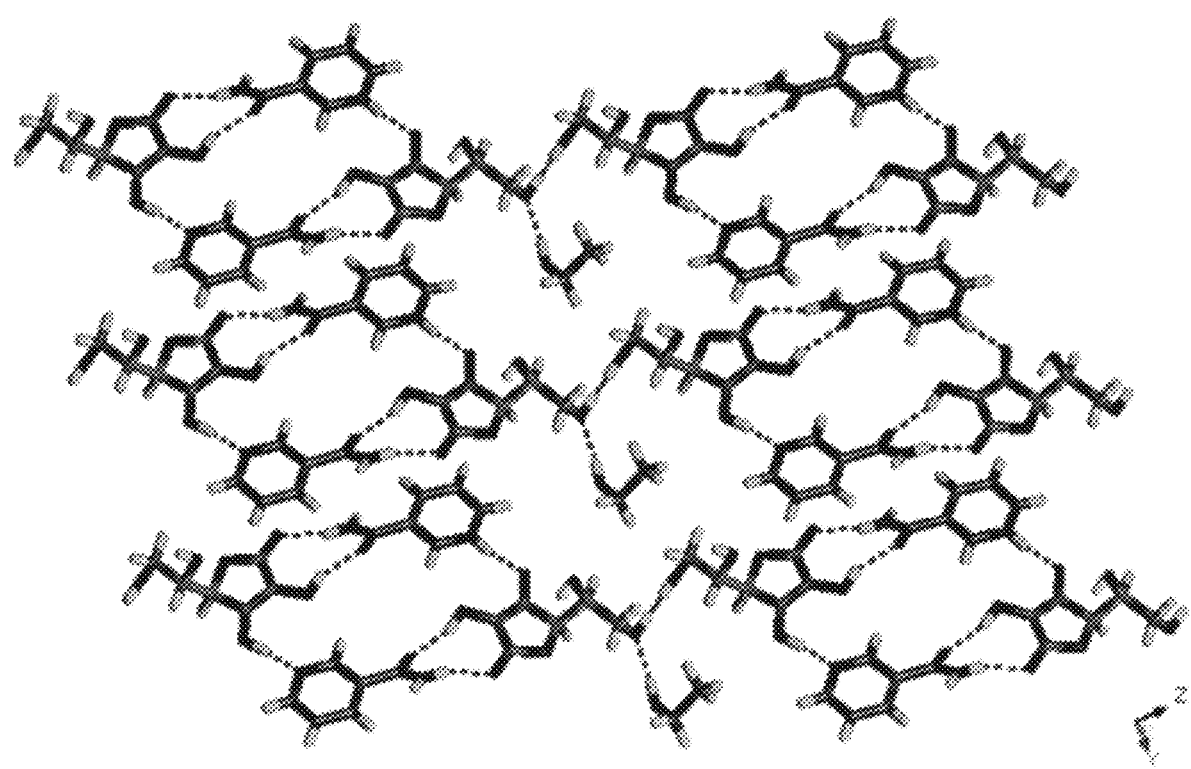
FIG. 53 shows the intermolecular interactions in KA1015, as described more fully in Example 13.

The single crystal x-ray structure reveals that the asymmetric unit contains two independent molecules of both L-ascorbic acid and nicotinamide along with an ethanol molecule. The complex forms a quaternary unit with pseudoinversion centre. These quaternary units are further connected to form tapes. The ethanol molecules are pendant to the quaternary units. The intermolecular hydrogen bonding in KA1015 is shown in FIG. 53 of the accompanying drawings.

Example 14

Hydrate of Co-Crystal of Epigallocatechin Gallate (EGCG) and Iso-Nicotinamid—KA10153

EGCG (90% pure) 45.83 mg (0.1000 mmol) and iso-nicotinamide (99% pure, Sigma Aldrich) 12.21 mg (0.1000 mmol) were dissolved in 6 mL of water. Colorless crystals were harvested after about 5 minutes. These colorless crystals were determined to be the hydrate of the 1:1 co-crystal of EGCG and iso-nicotinamide (hereinafter, KA10153). DSC analysis revealed phase changes at about 124° C., at about 133° C., and about 150° C.

Figure 54:
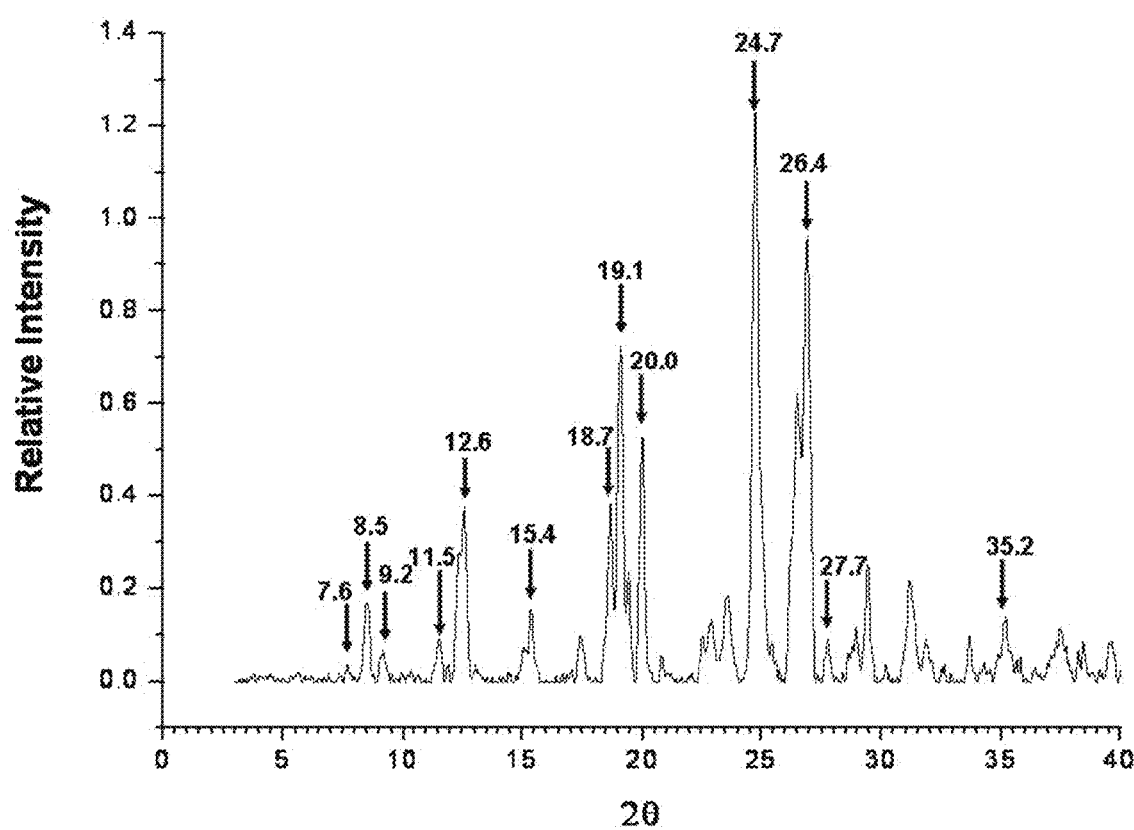
FIG. 54 shows an XRPD pattern of KA10153, as described more fully in Example 14, exhibiting major peaks at about the following positions: 7.6, 8.5, 9.2, 11.5, 12.6, 15.4, 18.7, 19.1, 20.0, 24.7, 26.4, 27.7 and 35.2.

KA10153 can be characterized using XRPD, and exhibited major peaks at about the following positions: 7.6, 8.5, 9.2, 11.5, 12.6, 15.4, 18.7, 19.1, 20.0, 24.7, 26.4, 27.7 and 35.2 degrees. The XRPD graph for KA10153 is shown in FIG. 54 of the accompanying drawings.

Single crystal x-ray diffraction analysis was also performed on KA10153 to determine the crystal structure and physical properties thereof. The crystallographic details are shown in the following table:

| KA10153 Crystallographic Data | |
| --- | --- |
| Empirical formula | C₂₈H₂₄N₂O₁₇ |
| Formula weight | 660.49 |
| Temperature | 298(2) K |
| Wavelength | 0.71073 Å |
| Crystal system | Monoclinic |
| Space group | C 2 |
| Unit cell dimensions | a = 19.603(8) Å |
| | b = 14.491(6) Å |
| | c = 10.585(4) Å |
| | α = 90°. |
| | β = 92.089(7)°. |
| | γ = 90°. |
| Volume | 3005(2) Å$^3$ |
| Z | 4 |
| Density (calculated) | 1.460 Mg/m$^3$ |
| Absorption coefficient | 0.124 mm$^{-1}$ |

| KA10153 Crystallographic Data | |
| --- | --- |
| Independent reflections | 4761 [R(int) = 0.0238] |
| Final R indices [I > 2sigma(I)] | R1 = 0.0671, wR2 = 0.1782 |
| R indices (all data) | R1 = 0.0964, wR2 = 0.2235 |

Figure 55:
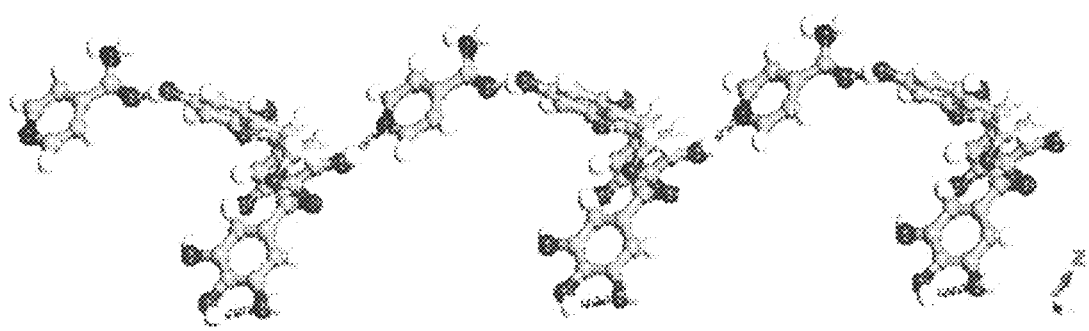
FIG. 55 shows the intermolecular interactions in KA10153, as described more fully in Example 14.

The single crystal x-ray structure analysis reveals that KA10153 is a hydrate of 1:1 cocrystal of EGCG and iso-nicotinamide. EGCG molecules and iso-nicotinamide molecules interact through one point hydrogen bonds (O—H . . . N, O . . . N: 2.756 Å) between the hydroxyl group of EgCG molecule and the aromatic nitrogen of iso-nicotinamide molecules. These dimeric units are further connected by O—H . . . O (O . . . O: 2.662 Å) hydrogen bonds formed between hydroxyl moieties of EgCG and carbonyl moieties of iso-nicotinamide molecules and thereby form zig-zag chains. The intermolecular hydrogen bonding in KA10153 is shown in FIG. 55 of the accompanying drawings.

Example 15

Hydrate of Co-Crystal of Ellagic Acid and Theophylline—TE1365

Ellagic acid dihydrate (96.0% pure, Fluka) 10.0 mg (0.0296 mmol) and anhydrous theophylline (99% pure, Sigma Aldrich) 27.0 mg (0.149 mmol) were added to 5.00 mL of ethanol and heated on a hotplate until boiling. The contents were cooled to room temperature using a water bath and filtered to obtain an orange solution. The solution was allowed to slowly evaporate at room temperature. Yellow plate-like crystals were harvested the next day. These crystals were determined to be the hydrate of 1:2 co-crystal of ellagic acid and theophylline (hereinafter, "TE1365"). DSC analysis showed a phase change at about 326° C.

Figure 56:
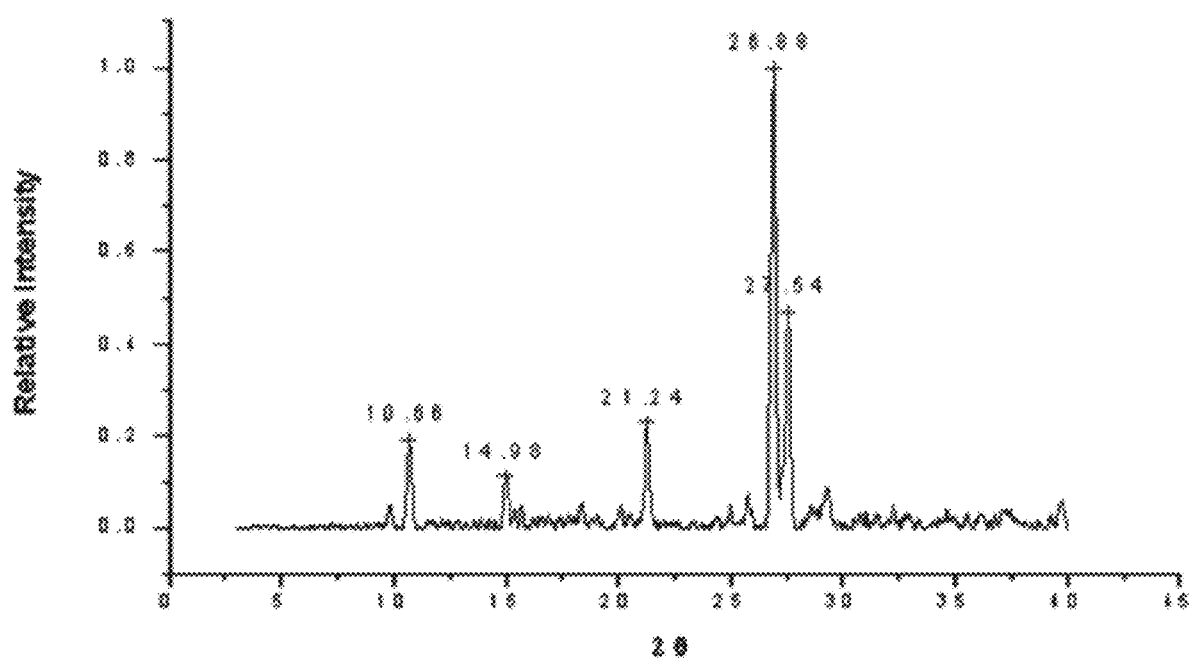
FIG. 56 shows an XRPD pattern of TE1365, as described more fully in Example 15, exhibiting major peaks at about the following positions: 10.66, 14.98, 21.24, 26.88 and 27.54.

TE1365 can be characterized using XRPD, and exhibited major peaks at about the following positions: 10.66, 14.98, 21.24, 26.88 and 27.54°. The XRPD graph for TE1365 is shown in FIG. 56 of the accompanying drawings.

Single crystal x-ray diffraction analysis was also performed on TE1365 to determine the crystal structure and physical properties thereof. The crystallographic details are shown in the following table:

| TE1365 Crystallographic Data | |
| --- | --- |
| Empirical formula | $C_{28}H_{22}N_8O_{12.13}$ |
| Formula weight | 664.62 |
| Temperature | 100(2) K |
| Wavelength | 0.71073 Å |
| Crystal system | Monoclinic |
| Space group | $P2_1/n$ |
| Unit cell dimensions | a = 11.636(3) Å |
| | b = 6.8183(19) Å |
| | c = 16.868(5) Å |
| | α = 90° |
| | β = 95.607(6)° |
| | γ = 90° |
| Volume | 1331.9(6) Å$^3$ |
| Z | 2 |
| Density (calculated) | 1.657 mg/m$^3$ |
| Reflections collected | 6429 |
| Independent reflections | 2339 [R (int) = 0.0318] |
| Final R indices [I > 2sigma(I)] | R1 = 0.0474, wR2 = 0.1108 |
| R indices (all data) | R1 = 0.0570, wR2 = 0.1155 |

Figure 57:
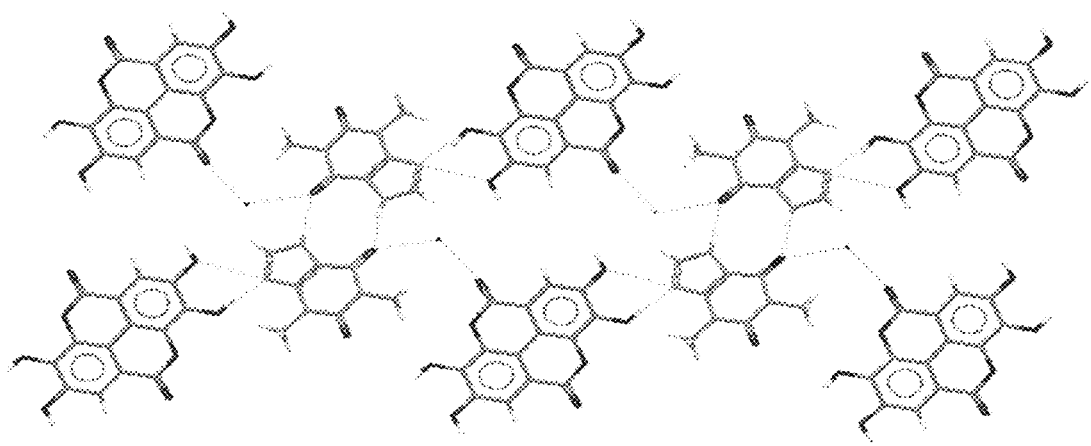
FIG. 57 shows the intermolecular interactions in TE1365 as described more fully in Example 15.

The single crystal structure shows that ellagic acid molecules form hydrogen bonds with theophylline molecules in a 1:2 ratio. In the crystal structure, there are non-stoichiometric water molecules that interact with the carbonyl oxygen of ellagic acid and the oxygen atom of theophylline. The intermolecular hydrogen bonding in TE1365 is shown in FIG. 57 of the accompanying drawings.

Example 16

Co-Crystal of Citric Acid Iso-Nicotinamide—DA005

Citric acid (anhydrous, EMD Chemicals) 76.8 mg (0.400 mmol) and iso-nicotinamide (99% pure, Sigma Aldrich) 146.4 mg (1.200 mmol)) were dissolved in 5 mL of methanol by heating on a hotplate until a clear solution was obtained. The solution was allowed to slowly evaporate at room temperature and colorless crystals were harvested after one day. These colorless crystals were determined to be the 1:2 co-crystal of citric acid and iso-nicotinamide (hereinafter, "DA005"). DSC analysis revealed phase changes at about 148° C. and at about 184° C.

Figure 58:
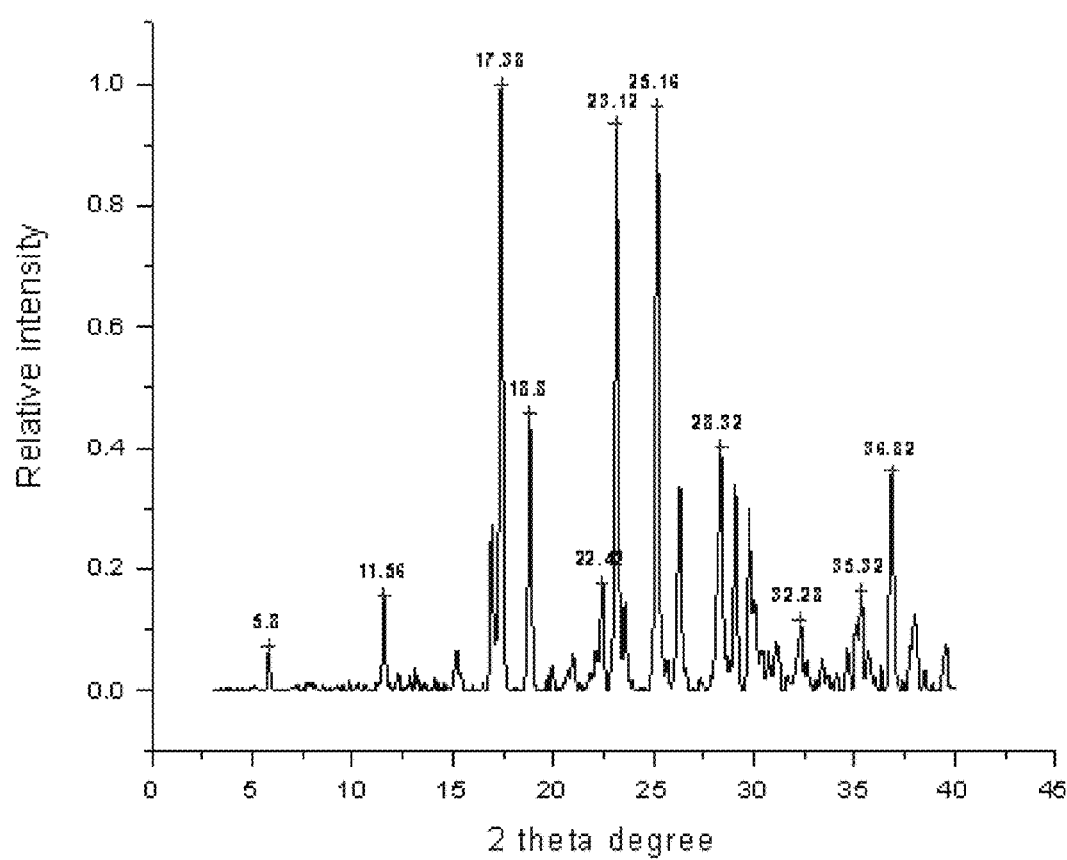
FIG. 58 shows an XRPD pattern of DA005, as described more fully in Example 16, exhibiting major peaks at about the following positions: 5.8, 11.6, 17.4, 18.8, 23.1, 25.2, 28.3, 32.3, 35.3, 36.8.

DA005 can be characterized using XRPD, and exhibited major peaks at about the following positions: 5.8, 11.6, 17.4, 18.8, 23.1, 25.2, 28.3, 32.3, 35.3, 36.8 degrees. The XRPD graph for DA005 is shown in FIG. 58 of the accompanying drawings.

Single crystal x-ray diffraction analysis was also performed on DA005 to determine the crystal structure and physical properties thereof. The crystallographic details are shown in the following table:

| DA005 Crystallographic Data | |
| --- | --- |
| Empirical formula | $C_{18}H_9N_4O_9$ |
| Formula weight | 416.22 |
| Temperature | 178(2) K |
| Wavelength | 0.71073 Å |
| Crystal system | Monoclinic |
| Space group | Cc |
| Unit cell dimensions | a = 31.39(2) Å |
| | b = 5.319(4) Å |
| | c = 11.762(8) Å |
| | α = 90°. |
| | β = 101.243(14)°. |
| | γ = 90°. |
| Volume | 1926(2) Å$^3$ |
| Z | 4 |
| Density (calculated) | 1.435 Mg/m$^3$ |
| Reflections collected | 4526 |
| Independent reflections | 1687 [R(int) = 0.0582] |
| Final R indices [I > 2sigma(I)] | R1 = 0.0830, wR2 = 0.1931 |
| R indices (all data) | R1 = 0.1040, wR2 = 0.2030 |

Figure 59:
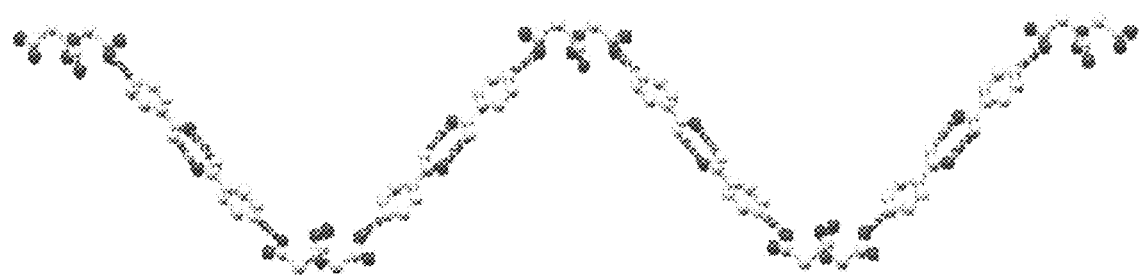
FIG. 59 shows the intermolecular interactions in DA005 as described more fully in Example 16.

The single crystal x-ray crystal structure of DA005 indicates that molecules of iso-nicotinamide form hydrogen bonds with molecules of citric acid with a stoichiometry of 2:1. The asymmetric unit of DA005 contains two crystallographically independent iso-nicotinamide molecules and a citric acid molecule. Two iso-nicotinamide molecules form a hydrogen-bonded dimer through the amide homosynthon (N—H . . . O, N . . . O, 2.907, 2.878 Å). Each of the aromatic nitrogen atoms of iso-nicotinamide are further included in a hydrogen-bond interaction with terminal carboxylic acid group of a citric acid molecule (O—H . . . N, O . . . N 2.536, 2.615 Å) to form zig-zag tapes. These tapes are connected through the middle carboxylic acid moieties of citric acid molecules. The intermolecular hydrogen bonding in DA005 is shown in FIG. 59 of the accompanying drawings.

Example 17

Co-Crystal of Protocatechuic Acid and ε-Caprolactam—TP1516

Protocatechuic acid (3,4-dihydroxy benzoic acid) (97% pure, Fisher Scientific) 15.40 mg (0.099 mmol) and ε-caprolactam (99% pure, Sigma Aldrich) 11.30 mg (0.0998 mmol) were dissolved in 1 mL of methanol and 3 mL of water by heating. The resulting solution was allowed to stand at room temperature and slowly evaporate. Colorless crystals of the co-crystal of protocatechuic acid and -caprolactam (hereinafter, "TP1516") were harvested after 13 days. DSC analysis showed a phase change at about 131° C.

Figure 60:
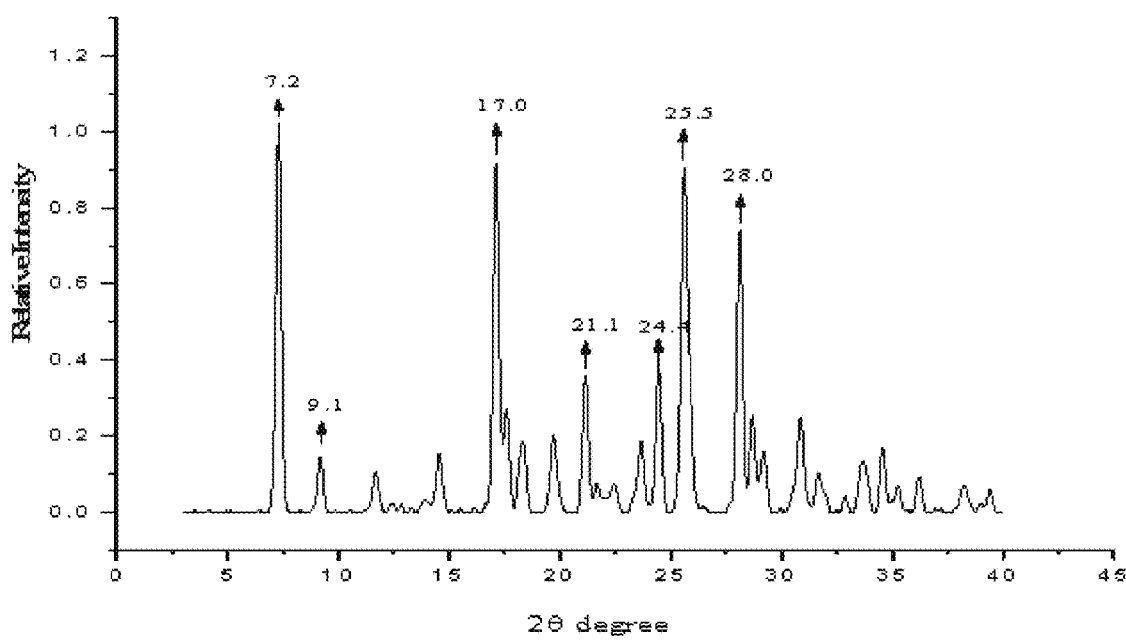
FIG. 60 shows an XRPD pattern of TP1516, as described more fully in Example 17, exhibiting major peaks at about the following positions: 7.2, 9.1, 17.0, 21.1, 24.4, 25.5 and 28.0.

TP1516 can be characterized using XRPD, and exhibited major peaks at about the following positions: 7.2, 9.1, 17.0, 21.1, 24.4, 25.5 and 28.0 degrees. The XRPD graph for TP1516 is shown in FIG. 60 of the accompanying drawings.

Single crystal x-ray diffraction analysis was also performed on TP1516 to determine the crystal structure and physical properties thereof. The crystallographic details are shown in the following table:

| TP1516 Crystallographic Data | |
|---|---|
| Empirical formula | $C_{13}H_{17}NO_5$ |
| Formula weight | 267.28 |
| Temperature | 293(2) K |
| Wavelength | 1.54178 Å |
| Crystal system | Monoclinic |
| Space group | P2(1)/c |
| Unit cell dimensions | a = 12.2531(12) Å |
| | b = 5.5475(8) Å |
| | c = 19.412(2) Å |
| | α = 90° |
| | β = 90.875(6)° |
| | γ = 90° |
| Volume | 1319.4(3) Å$^3$ |
| Z | 4 |
| Density (calculated) | 1.346 mg/m$^3$ |
| Reflections collected | 9655 |
| Independent reflections | 2217 [R (int) = 0.0546] |
| Final R indices [I > 2sigma(I)] | R1 = 0.0473, wR2 = 0.1276 |
| R indices (all data) | R1 = 0.0819, wR2 = 0.1394 |

Figure 61:
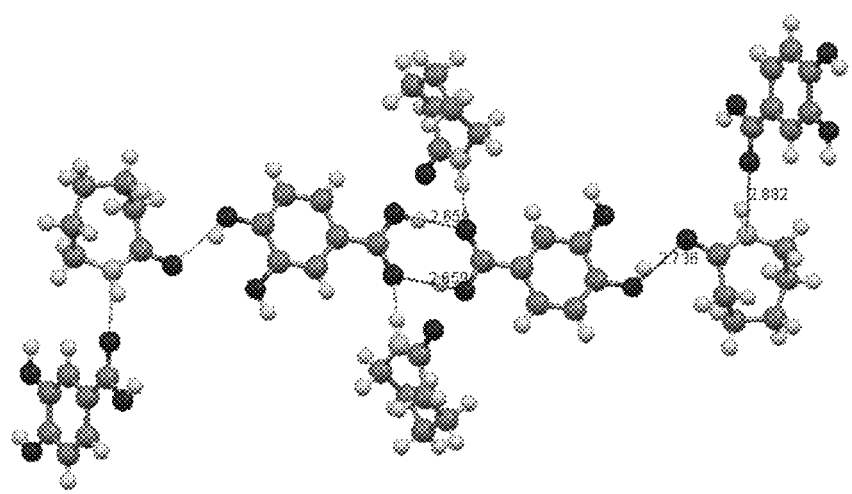
FIG. 61 shows the intermolecular interactions in TP1516 as described more fully in Example 17.

The crystal structure indicates carboxylic acid dimers of protocatechuic acid (OH—O: 2.659 Å) These dimers are connected to ε-caprolactam molecules through hydrogen bonding of the carbonyl moiety of protocatechuic acid and N—H moiety of ε-caprolactam (NH—O: 2.882 Å). Additional hydrogen bonding affords a three dimensional network. The intermolecular interactions in TP1516 are shown in FIG. 61 of the accompanying drawings.

Example 18

Co-Crystal of Protocatechuic Acid and Iso-Nicotinamide—TP147111

Protocatechuic acid (3,4-dihydroxybenzoic acid, 97% pure, Fisher Scientific) 15.4 mg (0.0999 mmol) and isonicotinamide (99% pure, Sigma Aldrich) 12.2 mg (0.0998 mmol) were dissolved in a mixture of 1 mL of methanol and 3 mL of water by heating. The resulting solution was allowed to slowly evaporate at room temperature. Colorless crystals of the co-crystal of protocatechuic acid and iso-nicotinamide (hereinafter, "TP14711") were harvested after 8 days. TP14711 can also be obtained through solvent drop grinding of protocatechuic acid (30.8 mg, 0.199 mmol), iso-nicotinamide (24.4 mg, 0.199 mmol) and water (30 µl) for 20 minutes in an agate pestle and mortar. DSC analysis showed a phase change at about 195° C.

Figure 62:
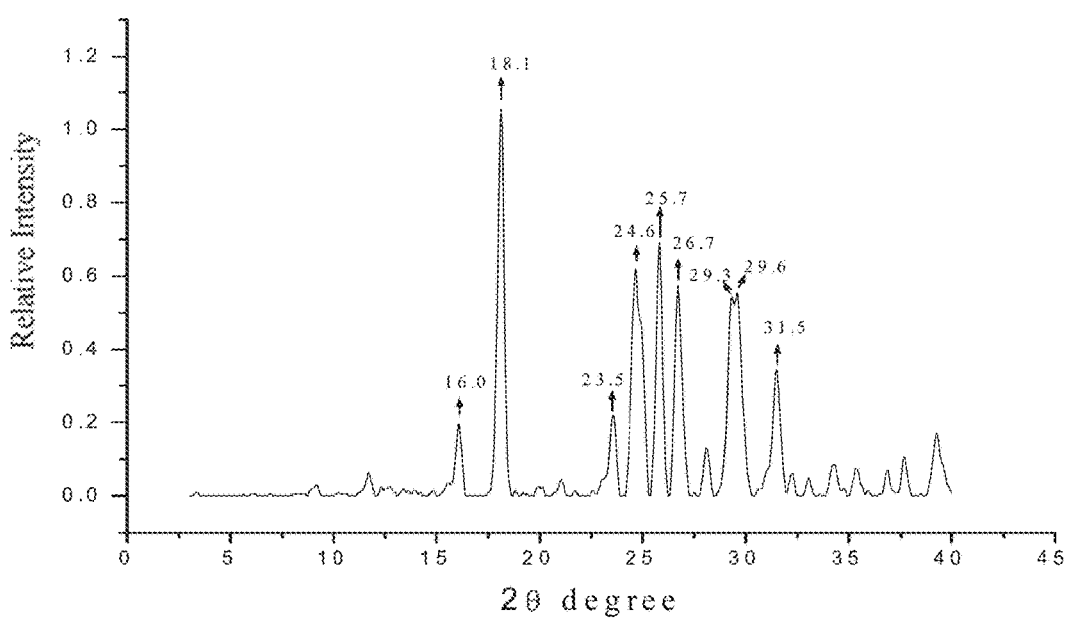
FIG. 62 shows an XRPD pattern of TP14711, as described more fully in Example 18, exhibiting major peaks at about the following positions: 16.0, 18.1, 24.6, 25.7, 26.7, 29.3, 29.6 and 31.5.

TP14711 can be characterized using XRPD, and exhibited major peaks at about the following positions: 16.0, 18.1, 24.6, 25.7, 26.7, 29.3, 29.6 and 31.5°. The XRPD graph for TP14711 is shown in FIG. 62 of the accompanying drawings.

Single crystal x-ray diffraction analysis was also performed on TP14711 to determine the crystal structure and physical properties thereof. The crystallographic details are shown in the following table:

| TP14711 Crystallographic Data | |
|---|---|
| Empirical formula | $C_{13}H_{12}N_2O_5$ |
| Formula weight | 276.25 |
| Temperature | 298(2) K |
| Wavelength | 1.54178 Å |
| Crystal system | Triclinic |
| Space group | P-1 |
| Unit cell dimensions | a = 3.9219(8) Å |
| | b = 10.020(2) Å |
| | c = 15.595(3) Å |
| | α = 99.845(11)° |
| | β = 95.978(13)° |
| | γ = 90.956(12)° |
| Volume | 600.2(2)Å$^3$ |
| Z | 2 |
| Density (calculated) | 1.529 mg/m$^3$ |
| Reflections collected | 1966 |
| Independent reflections | 1966 [R (int) = 0.0000] |
| Final R indices [I > 2sigma(I)] | R1 = 0.0728, wR2 = 0.2093 |
| R indices (all data) | R1 = 0.0833, wR2 = 0.2215 |

Figure 63:
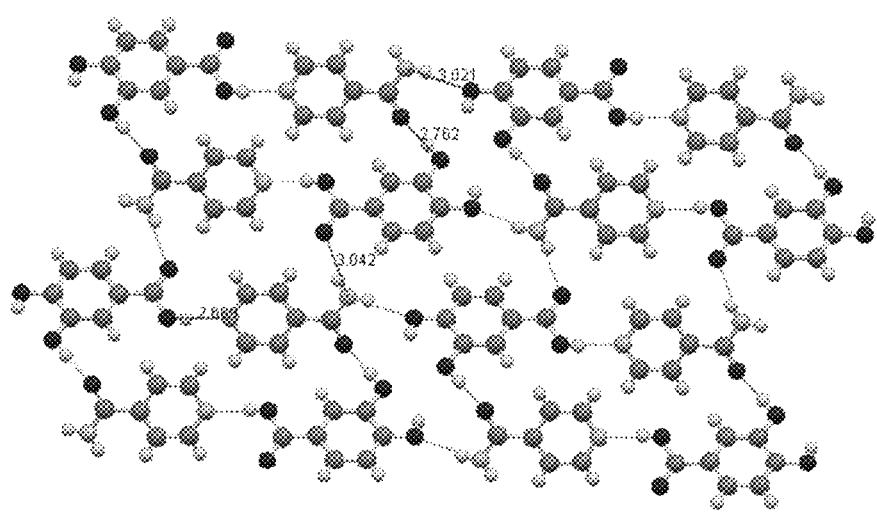
FIG. 63 shows the intermolecular interactions in TP14711 as described more fully in Example 18.

The single crystal X-ray crystallographic study analysis reveals that protocatechuic acid and isonicotinamide molecules form tapes through COOH—$N_{arom}$ (O—N: 2.669 Å) and N—H—O (N—O: 3.042 Å) supramolecular heterosynthons. These tapes are further connected through N—H—O (N—O: 3.021 Å) and O—H—O (O—O: 2.762 Å) hydrogen bonds to form sheets. The intermolecular interactions in TP14711 are shown in FIG. 63 of the accompanying drawings.

What is claimed is:

1. A process for improving health or nutrition of an animal or human having or predisposed to having a condition resulting from oxidative stress, the process comprising administering to the animal or human a composition comprising a nutraceutical co-crystal wherein
    (i) the nutraceutical co-crystal comprises a nutraceutical and a co-crystal former hydrogen bonded to each other, the nutraceutical co-crystal with or without impurities
    (ii) the nutraceutical is selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hesperitin, and protocatechuic acid, and (iii) the co-crystal former selected from the group consisting of pharmaceutically acceptable carbohydrates, amines, amides, sulfonamides, carboxylic acids, sulfonic acids, phenols, polyphenols, aromatic heterocycles, xanthines and alcohols.

2. The process of claim 1 wherein the nutraceutical is selected from the group consisting of resveratrol, EGCG, quercetin, ferulic acid, ellagic acid, hesperitin, and protocatechuic acid.

3. The process of claim 1 wherein the co-crystal former is selected from the group consisting of 1,5-napthalene-disulfonic acid, 1-hydroxy-2-naphthoic acid, 4-aminobenzoic acid, 4-aminopyridine, 4-chlorobenzene-sulfonic acid, 4-ethoxyphenyl urea, 7-oxo-DHEA, acesulfame, acetohydroxamic acid, adenine, adipic acid, alanine, allopurinaol, arginine, ascorbic acid, asparagine, aspartic acid, benzenesulfonic acid, benzoic acid, caffeine, camphoric acid, capric acid, chrysin, cinnamic acid, citric acid, clemizole, cyclamic acid, cysteine, dimethylglycine, D-ribose, fumaric acid, galactaric acid, genistein, gentisic acid, glucamine N-methyl, gluconic acid, glucosamine, glucuronic acid, glutamic acid, glutamine, glutaric acid, glycine, glycolic acid, hippuric acid, histidine, hydroquinone, imidazole, iprflavone, isoleucine, lactobionic acid, lauric acid, leucine, lysine, maleic acid, malic acid, malonic acid, mandelic acid, methionine, nicotinamide, nicotinic acid, orotic acid, oxalic acid, palmitic acid, pamoic acid, phenylalanine, piperazine, procaine, proline, p-toluenesulfonic acid, pyridoxamine, pyridoxine (4-pyridoxic acid), pyroglutamic acid, quercetin, resveratrol, saccharin, salicylic acid, salicylic acid 4-amino, sebacic acid, serine, stearic acid, succinic acid, tartaric acid, threonine, TRIS, tryptophan, tyrosine, urea, valine, Vitamin K5, xylitol, caffeine, paraxanthine, theobromine, theophylline, caprolactam, lactose, glucose and sucrose.

4. The process of claim 1 wherein the co-crystal former is selected from the group consisting of 1,5-napthalene-disulfonic acid, 1-hydroxy-2-naphthoic acid, 4-aminobenzoic acid, 4-aminopyridine, 4-chlorobenzene-sulfonic acid, 4-ethoxyphenyl urea, 7-oxo-DHEA, acesulfame, acetohydroxamic acid, adenine, adipic acid, alanine, allopurinaol, arginine, ascorbic acid, asparagine, aspartic acid, benzenesulfonic acid, benzoic acid, caffeine, camphoric acid, capric acid, chrysin, cinnamic acid, citric acid, clemizole, cyclamic acid, cysteine, dimethylglycine, D-ribose, fumaric acid, galactaric acid, genistein, gentisic acid, glucamine N-methyl, gluconic acid, glucosamine, glucuronic acid, glutamic acid, glutamine, glutaric acid, glycine, glycolic acid, hippuric acid, histidine, hydroquinone, imidazole, iprflavone, isoleucine, lactobionic acid, lauric acid, leucine, lysine, maleic acid, malic acid, malonic acid, mandelic acid, methionine, nicotinamide, nicotinic acid, orotic acid, oxalic acid, palmitic acid, pamoic acid, phenylalanine, piperazine, procaine, proline, p-toluenesulfonic acid, pyridoxamine, pyridoxine (4-pyridoxic acid), pyroglutamic acid, quercetin, resveratrol, saccharin, salicylic acid, salicylic acid 4-amino, sebacic acid, serine, stearic acid, succinic acid, tartaric acid, threonine, TRIS, tryptophan, tyrosine, urea, valine, Vitamin K5, xylitol, caffeine, paraxanthine, theobromine, theophylline, caprolactam, lactose, glucose and sucrose.

5. The process of claim 1 wherein the co-crystal former is selected from the group consisting of L-ascorbic acid (vitamin C), salicylic acid, citric acid, gallic acid, maleic acid, malic acid, tartaric acid, nicotinamide, iso-nicotinamide, nicotinic acid, iso-nicotinic acid, caffeine, paraxanthine, theobromine, theophylline, caprolactam, lactose, glucose and sucrose.

6. The process of claim 2 wherein the co-crystal former is selected from the group consisting of L-ascorbic acid (vitamin C), salicylic acid, citric acid, gallic acid, maleic acid, malic acid, tartaric acid, nicotinamide, iso-nicotinamide, nicotinic acid, iso-nicotinic acid, caffeine, paraxanthine, theobromine, theophylline, caprolactam, lactose, glucose and sucrose.

7. The process of claim 5 wherein the nutraceutical is selected from the group consisting of EGCG, ferulic acid, ellagic acid, hesperitin, and protocatechuic acid.

8. A process for improving health or nutrition of an animal or human having or predisposed to having a condition resulting from oxidative stress, the process comprising administering to the animal or human a composition comprising a nutraceutical co-crystal comprising epigallocatechin-3-gallate (EGCG) and a co-crystal former, wherein EGCG and the co-crystal former are hydrogen bonded to each other, the co-crystal with or without impurities.

9. The process of claim 8 wherein the co-crystal former selected from the group consisting of pharmaceutically acceptable carbohydrates, amines, amides, sulfonamides, carboxylic acids, sulfonic acids, phenols, polyphenols, aromatic heterocycles, xanthines and alcohols.

10. The process of claim 8 wherein the co-crystal former is selected from the group consisting of 1,5-napthalene-disulfonic acid, 1-hydroxy-2-naphthoic acid, 4-aminobenzoic acid, 4-aminopyridine, 4-chlorobenzene-sulfonic acid, 4-ethoxyphenyl urea, 7-oxo-DHEA, acesulfame, acetohydroxamic acid, adenine, adipic acid, alanine, allopurinaol, arginine, ascorbic acid, asparagine, aspartic acid, benzenesulfonic acid, benzoic acid, caffeine, camphoric acid, capric acid, chrysin, cinnamic acid, citric acid, clemizole, cyclamic acid, cysteine, dimethylglycine, D-ribose, fumaric acid, galactaric acid, genistein, gentisic acid, glucamine N-methyl, gluconic acid, glucosamine, glucuronic acid, glutamic acid, glutamine, glutaric acid, glycine, glycolic acid, hippuric acid, histidine, hydroquinone, imidazole, iprflavone, isoleucine, lactobionic acid, lauric acid, leucine, lysine, maleic acid, malic acid, malonic acid, mandelic acid, methionine, nicotinamide, nicotinic acid, orotic acid, oxalic acid, palmitic acid, pamoic acid, phenylalanine, piperazine, procaine, proline, p-toluenesulfonic acid, pyridoxamine, pyridoxine (4-pyridoxic acid), pyroglutamic acid, quercetin, resveratrol, saccharin, salicylic acid, salicylic acid 4-amino, sebacic acid, serine, stearic acid, succinic acid, tartaric acid, threonine, TRIS, tryptophan, tyrosine, urea, valine, Vitamin K5, xylitol, caffeine, paraxanthine, theobromine, theophylline, caprolactam, lactose, glucose and sucrose.

11. The process of claim 8 wherein the co-crystal former is selected from the group consisting of L-ascorbic acid (vitamin C), salicylic acid, citric acid, gallic acid, maleic acid, malic acid, tartaric acid, nicotinamide, iso-nicotinamide, nicotinic acid, iso-nicotinic acid, caffeine, paraxanthine, theobromine, theophylline, caprolactam, lactose, glucose and sucrose.

12. A process for improving health or nutrition of an animal or human having or predisposed to having a condition resulting from oxidative stress, the process comprising administering to the animal a composition comprising a nutraceutical co-crystal comprising at least one nutraceutical compound and L-ascorbic acid, wherein the nutraceutical compound and L-ascorbic acid are hydrogen bonded.

13. The process of claim 12 wherein the nutraceutical is selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hesperitin, and protocatechuic acid.

14. The process of claim 12 wherein the nutraceutical is selected from the group consisting of resveratrol, EGCG, quercetin, ferulic acid, ellagic acid, hesperitin, and protocatechuic acid.

15. The process of claim 12 wherein the nutraceutical is selected from the group consisting of EGCG, ferulic acid, ellagic acid, hesperitin, and protocatechuic acid.

16. A process for improving health or nutrition of an animal or human having or predisposed to having a condition resulting from oxidative stress, the process comprising administering to the animal or human a composition comprising a nutraceutical co-crystal comprising a flavonoid and a xanthine, wherein the nutraceutical is a flavonoid and the co-crystal former is a xanthine.

17. The process of claim 16 wherein the flavonoid is epigallocatechin-3-gallate (EGCG), quercetin, or hesperitin.

18. The process of claim 16 wherein the flavonoid is epigallocatechin-3-gallate (EGCG), quercetin, or hesperitin, and the xanthine is caffeine, theobromine, or theophylline.

\* \* \* \* \*